United States Patent
Ramaen et al.

(10) Patent No.: US 10,519,472 B2
(45) Date of Patent: Dec. 31, 2019

(54) RECOMBINANT HOST CELL FOR BIOSYNTHETIC PRODUCTION

(71) Applicant: Rhodia Operations, Paris (FR)

(72) Inventors: Odile Ramaen, Ablis (FR); Vincent Sauveplane, Elancourt (FR); Rudy Pandjaitan, Maisons Alfort (FR)

(73) Assignee: RHODIA OPERATIONS, Paris (FR)

( * ) Notice: Subject to any disclaimer, the term of this patent is extended or adjusted under 35 U.S.C. 154(b) by 195 days.

(21) Appl. No.: 14/655,610

(22) PCT Filed: Dec. 30, 2013

(86) PCT No.: PCT/EP2013/078117
§ 371 (c)(1),
(2) Date: Jun. 25, 2015

(87) PCT Pub. No.: WO2014/102368
PCT Pub. Date: Jul. 3, 2014

(65) Prior Publication Data
US 2015/0322465 A1 Nov. 12, 2015

(30) Foreign Application Priority Data

Dec. 27, 2012 (EP) .................................. 12199502
Feb. 20, 2013 (EP) .................................. 13156021

(51) Int. Cl.
*C12N 1/16* (2006.01)
*C12P 7/24* (2006.01)
(Continued)

(52) U.S. Cl.
CPC ................. *C12P 7/24* (2013.01); *C12N 1/16* (2013.01); *C12N 9/0028* (2013.01); *C12N 9/0042* (2013.01); *C12N 9/0073* (2013.01); *C12N 9/1007* (2013.01); *C12N 9/88* (2013.01); *C12N 9/93* (2013.01); *C12N 15/52* (2013.01); *C12Y 105/01036* (2013.01);
(Continued)

(58) Field of Classification Search
None
See application file for complete search history.

(56) References Cited

U.S. PATENT DOCUMENTS

| 5,017,388 A | 5/1991 | Rabenhorst et al. |
| 5,721,125 A | 2/1998 | van Berkel et al. |

(Continued)

FOREIGN PATENT DOCUMENTS

| EP | 0405197 A1 | 1/1991 |
| EP | 2388333 A2 | 11/2011 |
| WO | 2011124693 A1 | 10/2011 |

OTHER PUBLICATIONS

U.S. Appl. No. 61/722,513, filed Nov. 5, 2012, Specification, Claims and Drawings.*

(Continued)

*Primary Examiner* — Richard C Ekstrom
(74) *Attorney, Agent, or Firm* — Osha Liang LLP

(57) ABSTRACT

A cell may include heterologous polynucleotides encoding a multienzyme complex involved in the metabolic pathway of phenylpropanoids and biosynthesis of a vanilloid or a hydroxybenzaldehyde precursor thereof, which multienzyme complex comprises enzymes for the biosynthesis of coumaric acid and a crotonase.

Figure 1:
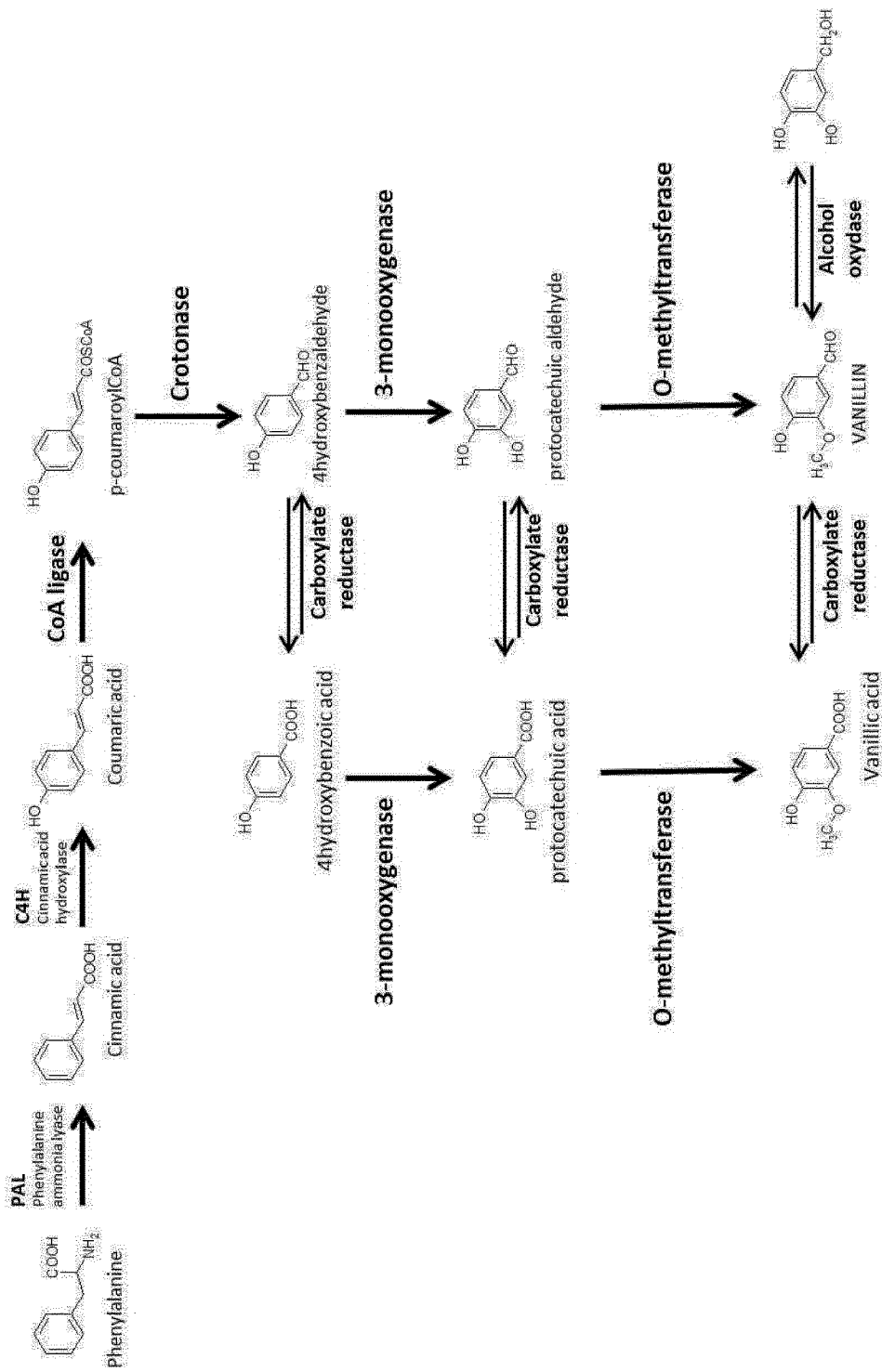

23 Claims, 17 Drawing Sheets
Specification includes a Sequence Listing.

(51) Int. Cl.
  C12N 9/88    (2006.01)
  C12N 9/02    (2006.01)
  C12N 9/00    (2006.01)
  C12N 9/10    (2006.01)
  C12N 9/06    (2006.01)
  C12N 15/52   (2006.01)

(52) U.S. Cl.
  CPC .......... C12Y 106/02004 (2013.01); C12Y 114/13002 (2013.01); C12Y 114/13007 (2013.01); C12Y 114/13011 (2013.01); C12Y 201/01068 (2013.01); C12Y 301/01073 (2013.01); C12Y 402/01 (2013.01); C12Y 402/01017 (2013.01); C12Y 403/01023 (2013.01); C12Y 403/01024 (2013.01); C12Y 403/01025 (2013.01); C12Y 602/01012 (2013.01)

(56) References Cited

U.S. PATENT DOCUMENTS

| | | | |
|---|---|---|---|
| 5,912,119 | A | 6/1999 | Radman et al. |
| 6,372,461 | B1 | 4/2002 | Frost |
| 2003/0070188 | A1 | 4/2003 | Havkin-Frenkel et al. |
| 2004/0209962 | A1* | 10/2004 | Crandall, Jr. ......... A01N 35/02 514/701 |
| 2015/0267227 | A1* | 9/2015 | Lindberg Moller ..... C12N 9/88 800/317.3 |

OTHER PUBLICATIONS

International Search Report and Written Opinion issued in corresponding International Application No. PCT/EP2013/078117, dated Feb. 3, 2014 (11 pages).
D. Di Gioia et al.; "Metabolic engineering of Pseudomonas fluorescens for the production of vanillin from ferulic acid"; Journal of Biotechnology, 156, pp. 309-316; Aug. 22, 2011 (8 pages).
A. R. Brochado et al.; "Improved vanillin production in baker's yeast through in silico design"; Microbial Cell Factories, 9:84, pp. 1-15; Nov. 8, 2010 (15 pages).
H. Priefert et al.; "Biotechnological production of vanillin"; Appl. Microbiol. Biotechnol., 56, pp. 296-314; Jun. 23, 2001.
B. Kaur et al.; "Biotechnological and Molecular Approches for Vanillin Production: a Review"; Appl. Biochem. Biotechnol., 169, pp. 1353-1372; Jun. 11, 2013 (20 pages).
P. S. J. Cheetham; "The use of biotransformations for the production of flavours and fragrances"; IBTECH, vol. 11, pp. 478-488; Nov. 1993 (11 pages).
S. Hagedorn et al.; "Microbial biocatalysis in the generation of flavor and fragrance chemicals"; Annu. Rev. Microbial., 48, pp. 773-800; 1994 (28 pages).
JPN. Rosazza et al.; "Biocatalytic transformations of ferulic acid: an abundant aromatic natural product"; Journal of Industrial Microbiology, 15, pp. 457-471; 1995 (15 pages).
A. Hausler et al.; "Microbial Production of Natural Flavors"; ASM News, vol. 63, No. 10, pp. 551-559; 1997 (9 pages).
U. Krings et al.; "Biotechnological production of flavours and fragrances"; Appl. Microbiol. Biotechnol., 49, pp. 1-8; 1998 (8 pages).
W.-R. Abraham et al.; "Microbial transformations of some terpenoids and natural compounds"; Bioflavour '87, Walter de Gruyter & Co., pp. 399-414; 1988 (16 pages).
T. Chatterjee et al.; "Microbial conversion of isoeugenol to vanillin by Rhodococcus rhodochrous"; Indian Journal of Chemistry, vol. 38B, pp. 538-541; May 1999 (4 pages).
E. Shimoni et al.; "Isolation of a *Bacillus* .sp. capable of transforming isoeugenol to vanillin"; Journal of Biotechnology, 78, pp. 1-9; 2000 (9 pages).
Li-Qing Zhao et al.; "Biotransformation of isoeugenol to vanillin by a novel strain of Bacillus fusiformis"; Biotechnology Letters, 27, pp. 1505-1509; 2005 (5 pages).
Y. Zhang et al.; "Metabolism of isoeugenol via isoeugenol-diol by a newly isolated strain of Bacillus subtilis HS8"; Appl. Microbial. Biotechnol., 73, pp. 771-779; 2006 (10 pages).
T. Unna et al.; "Metabolic Characterization of Newly Isolated Pseudomonas nitroreducens Jin1 Growing on Eugenol and Isoeugenol"; J. Agric. Food Chem., vol. 55, No. 21, pp. 8556-8561; Sep. 15, 2007 (6 pages).
M. Yamada et al.; "Biotransformation of isoeugenol to vanillin by Pseudomonas putida IE27 cells"; Appl. Microbiol. Biotechnol., 73, pp. 1025-1030; 2007 (7 pages).
R. C. Kasana et al.; "Isolation and Identification of a Novel Strain of Pseudomonas chlororaphis Capable of Transforming Isoeugenol to Vanillin"; Current Microbiology, vol. 54, pp. 457-461; 2007 (5 pages).
D. Hua et al.; "Biotransformation of isoeugenol to vanillin by a newly isolated Bacillus pumilus strain: Identification of major metabolites"; Journal of Biotechnology, 130, pp. 463-470; 2007 (8 pages).
R. Seshadri et al.; "Oxidation of isoeugenol by Nocardia iowensis"; Enzyme and Microbial Technology, 43, pp. 486-494; 2008 (9 pages).
E. H. Hansen et al.; "De Novo Biosynthesis of Vanillin in Fission Yeast (*Schizosaccharomyces pombe*) and Baker's Yeast (*Saccharomyces cerevisiae*)"; Applied and Environmental Microbiology, vol. 75, No. 9, pp. 2765-2774; May 2009 (10 pages).
A. Kondo et al.; "Development of microbial cell factories for bio-refinery through synthetic bioengineering"; Journal of Biotechnology, 163, pp. 204-216; 2013 (13 pages).
J. M. Cherry et al.; "*Saccharomyces* Genome Database: the genomics resource of budding yeast"; Nucleic Acids Research, vol. 40, pp. D700-D705; Nov. 21, 2011 (6 pages).
J. Nielsen et al.; "Impact of systems biology on metabolic engineering of *Saccharomyces cerevisiae*"; FEMS Yeast Res, 8, pp. 122-131; Aug. 29, 2007 (10 pages).
J. M. Otero et al.; "Whole genome sequencing of *Saccharomyces cerevisiae*: from genotype to phenotype for improved metabolic engineering applications"; BMC Genomics., 11:723, pp. 1-17; Dec. 22, 2010 (17 pages).
Fraser et al., "The Phenylpropanoid Pathway in Arabidopsis", The *Arabidopsis* Book, American Society of Plant Biologist, Dec. 8, 2011 (19 pages).
Choi et al., "Biosynthesis of plant-specific phenylpropanoids by construction of an artificial biosynthetic pathway in *Escherichia coli*", J Ind Microbiol Biotechnol, 2011, vol. 38, pp. 1657-1665 (9 pages).
Vogt, "Phenylpropanoid Biosynthesis", Molecular Plant, vol. 3, No. 1, pp. 2-20, Jan. 2010 (19 pages).
English translation of a Second Office Action dated Mar. 14, 2018, by the State Intellectual Property Office of the Peoples Republic of China in corresponding Chinese Patent Application No. 201380073404.7 (13 pages).
Zhen, Li; "Genetic Manipulation of Lignin Biosynthesis in Poplar"; Basic Science Volume of China Master's Theses, Full-text Database, No. 10, (2009). (3 pages).

* cited by examiner

Fig. 11

PAL pop_715AA (SEQ ID 1)

METVTKNGYQNGSLESLCVNQRDPLSWGVAAEAMKGSHLDEVKRMVADYRKPVVKLGGET
LTIAQVASIAGHDTGDVKVELSESARPGVKASSDWVMDSMDKGTDSYGVTTGFGATSHRR
TKQGGALQKELIRFLNAGIFGNGTETCHTLPHSATRAAMLVRINTLLQGYSGIRFEILEA
ITRLLNNNITPCLPLRGTITASGDLVPLSYIAGLLTGRPNSKATGPTGEVLDAAEAFKAA
GIESGFFELQPKEGLALVNGTAVGSGLASMVLFETNVLAVLSELLSAIFAEVMNGKPEFT
DHLTHKLKHHPGQIEAAAIMEHILDGSAYMKAAKKLHETDPLQKPKQDRYALRTSPQWLG
PQIEVIRFSTKSIEREINSVNDNPLIDVSRNKAIHGGNFQGTPIGVSMDNVRLAIASIGK
LLFAQFSELVNDFYNNGLPSNLTASRNPSLDYGFKGAEIAMASYCSELQYLANPVTTHVQ
SAEQHNQDVNSLGLISSRKTAEAVDILKLMSTTFLVALCQAIDLRHLEENLKSAVKNTVS
QVSKRVLTTGANGELHPSRFCEKELLKVVDREYVFAYVDDPCSATYPLMQKLRQVFVDHA
LENGENEKNFSTSVFQKIEAFEEELKALLPKEVESARAAYDSGNSAIDNKIKECRSYPLY
KFVREELGTVLLTGEKVQSPGEEFDKVFTAMCQGKIIDPMLECLGEWNGSPLPIC

PALpet_718AA (SEQ ID 2)

MAYVNGTTNCHANGNGLDLCMKKEDPLNWGVAAEALTGSHLDEVKRMVAEYRKPVVKLEG
ETLTISQVAAISARDDSGVKVELSEEARAGVKASSDWVMDSMNKGTDSYGVTTGFGATSH
RRTKQGGALQKELIRFLNAGIFGSGAEAGNNTLPHSATRAAMLVRINTLLQGYSGIRFEI
LEAITKFLNHNITPCLPLRGTITASGDLVPLSYIAGLLTGRPNSKAVGPTGVTLSPEEAF
KLAGVEGGFFELQPKEGLALVNGTAVGSGMASMVLFEANILAVLAEVMSAIFAEVMQGKP
EFTDHLTHKLKHHPGQIEAAAIMEHILDGSAYVKAAQKLHEMDPLQKPKQDRYALRTSPQ
WLGPQIEVIRSSTKMIEREINSVNDNPLIDVSRNKAIHGGNFQGSPIGVSMDNTRLAIAA
IGKLMFAQFSELVNDFYNNGLPSNLSGGRNPSLDYGFKGAEIAMASYCSELQFLANPVTN
HVQSAEQHNQDVNSLGLISSRKTSEAVEILKLMSTTFLVGLCQAIDLRHLEENLKSTVKN
TVSQVAKRVLTMGVNGELHPSRFCEKDLLRVVDREYIFAYIDDPCSATYPLMQKLRETLV
EHALNNGDKERNLSTSIFQKIAAFEDELKALLPKEVETARAALESGNPAIPNRIKECRSY
PLYKFVREELGTEYLTGEKVRSPGEEFEKVFTAMSKGEIIDPLLECLESWNGAPLPIC

C4Hgly_506AA (SEQ ID 3)

MDLLLLEKTLIGLFLAAVVAIAVSTLRGRKFKLPPGPLPVPIFGNWLQVGDDLNHRNLTD
LAKKFGDIFLLRMGQRNLVVVSSPELAKEVLHTQGVEFGSRTRNVVFDIFTGKGQDMVFT
VYGEHWRKMRRIMTVPFFTNKVVQQYRHGWESEAAAVVEDVKKNPDAAVSGTVIRRRLQL
MMYNNMYRIMFDRRFESEEDPIFQRLRALNGERSRLAQSFEYNYGDFIPILRPFLKGYLK
ICKEVKETRLKLFKDYFVDERKKLGSTKSTNNNNELKCAIDHILDAQRKGEINEDNVLYI
VENINVAAIETTLWSIEWGIAELVNHPEIQQKLRDEIDRVLGAGHQVTEPDIQKLPYLQA
VVKETLRLRMAIPLLVPHMNLHDAKLGGYDIPAESKILVNAWWLANNPAHWKKPEEFRPE
RFFEEESLVEANGNDFRYLPFCVGRRSCPGIILALPILGITLGRLVQNFELLPPPCQSQI
DTSEKGGQFSLHILKHSTIVAKPRSF

Fig. 11 (continued)

C4Hpet_506AA (SEQ ID 4)

MMDFVLLEKALLGLFIATIVAITISKLRGKKLKLPPGPIPVPVFGNWLQVGDDLNQRNLV
DYAKKFGDLFMLRMGQRNLVVVSSPELAKDVLHTQGVEFGSRTRNVVFDIFTGKGQDMVF
TVYSEHWRKMRRIMTVPFFTNKVVQQYRFGWEDEAARVVEDVKANPEAATNGIVLRNRLQ
LLMYNNMYRIMFDRRFESVDDPLFLKLKALNGERSRLAQSFEYHFGDFIPILRPFLRGYL
KLCQEIKDKRLKLFKDYFVDERKKLESIKSVDNNSLKCAIDHIIEAQQKGEINEDNVLYI
VENINVAAIETTLWSIEWGIAELVNNPEIQKKLRHELDTVLGAGVQICEPDVQKLPYLQA
VIKETLRYRMAIPLLVPHMNLHDAKLAGYDIPAESKILVNAWWLANNPAHWNKPDEFRPE
RFLEEESKVEANGNDFKYIPFGVGRRSCPGIILALPILGIVIGRLVQNFELLPPPGQSKI
DTAEKGGQFSLQILKHSTIVCKPRSL

4CLpop_570AA (SEQ ID 5)

MMSVATVEPPKPELSPPQNQNAPSSHETDHIFRSKLPDITISNDLPLHAYCFENLSDFSD
RPCLISGSTGKTYSFAETHLISRKVAAGLSNLGIKKGDVIMTLLQNCPEFVFSFIGASMI
GAVITTANPFYTQSEIFKQFSASRAKLIITQSQYVNKLGDSDCHENNQKPGEDFIVITID
DPPENCLHFNVLVEASESEMPTVSILPDDPVALPFSSGTTGLPKGVILTHKSLITSVAQQ
VDGEIPNLYLKQDDVVLCVLPLFHIFSLNSVLLCSLRAGSAVLLMQKFEIGSLLELIQKH
NVSVAAVVPPLVLALAKNPLEANFDLSSIRVVLSGAAPLGKELEDALRSRVPQAILGQGY
GMTEAGPVLSMCLAFSKQPFPTKSGSCGTVVRNAELKVIDPETGRSLGYNQPGEICIRGS
QIMKGYLNDAEATANTIDVEGWLHTGDIGYVDDDEIFIVDRVKEIIKFKGFQVPPAELE
ALLVNHPSIADAAVVPQKDEVAGEVPVAFVVRSDDLDLSEEAVKEYIAKQVVFYKKLHKV
FFVHSIPKSASGKILRKDLRAKLATATTMS

ECHpfl_276AA (SEQ ID 6)

MSNYEGRWTTVKVEIEDGIAWVILNRPEKRNAMSPTLNREMIDVLETLEQDPAAGVLVLT
GAGEAWTAGMDLKEYFREVDAGPEILQEKIRREASQWQWKLLRMYAKPTIAMVNGWCFGG
GFSPLVACDLAICADEATFGLSEINWGIPPGNLVSKAMADTVGHRQSLYYIMTGKTFGGQ
KAAEMGLVNDSVPLARLREVTIELARNLLEKNPVVLRAAKHGFKRCRELTWEQNEDYLYA
KLDQSRLLDTEGGREQGMKQFLDDKSIKPGLQAYKR

ECHavi_276AA (SEQ ID 7)

MNKYEGRWKTVIVEIEGGIAWVTLNRPDKRNAMSPTLNREMRDVLETLEQDPAARVLVLT
GAGSAWTAGMDLKEYFREVDAGPEILQEKIRREACEWQWKLLRMYAKPTVAMVNGWCFGG
GFSPLVACDLAICADEATFGLSEINWGIPPGNLVSKAMADTVGHRQALYYIMTGKTFDGR
QAAEMGLVNQSVPLAQLRETVATLCQDLLDKNPVVLRAAKNGFKRCRELTWEQNEDYLYA
KLDQSRLLDEEGGREEGMRQFLDEKSIKPGLQAYKR

Fig. 11 (continued)

HBHpae_394AA (SEQ ID 8)

MKTQVAIIGAGPSGLLLGQLLHKAGIDNVILERQTPDYVLGRIRAGVLEQGMVDLLREAG
VDRRMARDGLVHEGVEIAFAGQRRRIDLKRLSGGKTVTVYGQTEVTRDLMEAREACGATT
VYQAAEVRLHDLQGERPYVTFERDGERLRLDCDYIAGCDGFHGISRQSIPAERLKVFERV
YPFGWLGLLADTPPVSHELIYANHPRGFALCSQRSATRSRYYVQVPLTEKVEDWSDERFW
TELKARLPAEVAEKLVTGPSLEKSIAPLRSFVVEPMQHGRLFLAGDAAHIVPPTGAKGLN
LAASDVSTLYRLLLKAYREGRGELLERYSAICLRRIWKAERFSWWMTSVLHRFPDTDAFS
QRIQQTELEYYLGSEAGLATIAENYVGLPYEEIE

HBHavi_394AA (SEQ ID 9)

MKTQVAIIGAGPSGLLLGQLLHKAGIDNVILERHSPDYVLGRIRAGVLEQGVVDLLREAG
VAERMDREGLVHEGIELACSGRRIRLDLKALSGGKTVMVYGQTEVTRDLMDARRASGAPI
VYEAQNVRLSGLKDGMPHVTYEKDGQTHRLDCDYIAGCDGFHGVSRQSIPAEALSHYERV
YPFGWLGLLSDTPPVHEELIYAHTDLGFVLCSQRSPTRSRYYLQVPLSDRVEDWSDERFW
NELKRRLPGDVANRLVTGPSLEKSIAPLRSYVVEPMQYGRLFLVGDAAHIVPPTGAKGLN
LAGSDVCYLYRILLKVYREGRTELLEKYSELALRRVWKGERFSWFMTNLLHDFEGSDAFD
RRMQLADRDYYLDSEAGRVTIAENYVGLPYEEIA

COMTmsa_365AA (SEQ ID 10)

MGSTGETQITPTHISDEEANLFAMQLASASVLPMILKSALELDLLEIIAKAGPGAQISPI
EIASQLPTTNPDAPVMLDRMLRLLACYNILTCSVRTQQDGKVQRLYGLATVAKYLVKNED
GVSISALNLMNQDKVLMESWYHLKDAVLDGGIPFNKAYGMTAFEYHGTDPRFNKVFNKGM
SDHSTITMKKILETYTGFEGLKSLVDVGGGTGAVINTIVSKYPTIKGINFDLPHVIEDAP
SYPGVEHVGGDMFVSIPKADAVFMKWICHDWSDEHCLKFLKNCYEALPDNGKVIVAECIL
PVAPDSSLATKGVVHIDVIMLAHNPGGKERTQKEFEDLAKGAGFQGFKVHCNAFNTYIME
FLKKV

COMTvpl_365AA (SEQ ID 11)

MATWVEHQQQQNGSKDVDEEACMYAMQLSSMVVLPMTLRVAVELGILEQIQAGGPDSYLT
AEDLAARLGNSNPLAPVMIERILRLLTSYSILNFTDTVDGEGRTVRSYGAAHVCKYLTPN
QDGVSMAPLVLMNTDKVLMESWYHMKDAVTNGGIPFNLAYGMTAFEYHGKDLRFNKVFNE
GMKNNSIIITKKILERYKRFEDVNVLIDVGGGIGGTISMITAKYPHIHGINFDLPHVVSE
APPFQGVEHVGGNMFESVPIGDAIFIKWILHDWSDEHCLKLLRNCAKSLPDKGKVIVVEC
ILPDAPLVTPEAEGVFHLDMIMLAHNPGGKERTKKEFKELAMLSGFSNFKALFSYANVWV
MEFNK

Fig. 11 (continued)

pheA_524AA (SEQ ID 12)

MTVKQKNGVRPFTGEEYLESLRDGREVYVYGERVKDITTHPAYRNAARMFARWYDRLHQL
HAEDEQRGGPENWKWTVPTDTGNGGWTHPYFIGARCAEDLIKGRDTIAELQRVVYGWLGR
SPDYKAAFVGTLGANSNFYAPYQENAKRWYNETQERLLFWNHAIVNPPVDRNKPIEEVGD
VFMHVEKETDAGVVVSGAKVVATGSALTHMNFIGQYGPVPVKDKKFALIFTVPMNAPGVK
LISRASYEFVAAATGSPFDYPLSSRLDENDAILVFDKVLVPWENIFVYEDVEKVNTFFPR
SGFINRFTLHGLTRLAVKLDFIAGLVLKATEATGVKDFRGVQARVGEILAWRHLFWSLSE
AQVRNPEPWVDDYVLPNLSAGLAYRVFASEAYPKIKDLIEKDLASSLIYLPSNAADFLEP
EIRPYLEKYVRGSNGYDAESRVKLLKLLWDAVGSEFGGRHELYERNYAGNHENIRLEVLL
TALNTGDADRFKEFAEQCMDEYDLNGWKVPDLINPDDVNIIRKR flavin reductase_146AA (SEQ ID 13)

MGKFATGVTVVTTEFQGEAKGMTANAFMSVSLDPKLVVVSIGHKARMHDIVKQTGKFAVN
ILRRDQEELSRLFAGQLKEERHVSFDWVNGHPILPEALANILCNVHSTYVAGDHTLYFGE
VTDILMKDEPGDPLLFFEGKYRSIGQ

Carboxylic acid reductase_1174AA (SEQ ID 14)

MAVDSPDERLQRRIAQLFAEDEQVKAARPLEAVSAAVSAPGMRLAQIAATVMAGYADRPA
AGQRAFELNTDDATGRTSLRLLPRFETITYRELWQRVGEVAAAWHHDPENPLRAGDFVAL
LGFTSIDYATLDLADIHLGAVTVPLQASAAVSQLIAILTETSPRLLASTPEHLDAAVECL
LAGTTPERLVVFDYHPEDDDQRAAFESARRRLADAGSLVIVETLDAVRARGRDLPAAPLF
VPDTDDDPLALLIYTSGSTGTPKGAMYTNRLAATMWQGNSMLQGNSQRVGINLNYMPMSH
IAGRISLFGVLARGGTAYFAAKSDMSTLFEDIGLVRPTEIFFVPRVCDMVFQRYQSELDR
RSVAGADLDTLDREVKADLRQNYLGGRFLVAVVGSAPLAAEMKTFMESVLDLPLHDGYGS
TEAGASVLLDNQIQRPPVLDYKLVDVPELGYFRTDRPHPRGELLLKAETTIPGYYKRPEV
TAEIFDEDGFYKTGDIVAELEHDRLVYVDRRNNVLKLSQGEFVTAHLEAVFASSPLIRQ
IFIYGSSERSYLLAVIVPTDDALRGRDTATLKSALAESIQRIAKDANLQPYEIPRDFLIE
TEPFTIANGLLSGIAKLLRPNLKERYGAQLEQMYTDLATGQADELLALRREAADLPVLET
VSRAAKAMLGVASADMRPDAHFTDLGGDSLSALSFSNLLHEIFGVEVPVGVVVSPANELR
DLANYIEAERNSGAKRPTFTSVHGGGSEIRAADLTLDKFIDARTLAAADSIPHAPVPAQT
VLLTGANGYLGRFLCLEWLERLDKTGGTLICVVRGSDAAAARKRLDSAFDSGDPGLLEHY
QQLAARTLEVLAGDIGDPNLGLDDATWQRLAETVDLIVHPAALVNHVLPYTQLFGPNVVG
TAEIVRLAITARRKPVTYLSTVGVADQVDPAEYQEDSDVREMSAVRVVRESYANGYGNSK
WAGEVLLREAHDLCGLPVAVFRSDMILAHSRYAGQLNVQDVFTRLILSLVATGIAPYSFY
RTDADGNRQRAHYDGLPADFTAAAITALGIQATEGFRTYDVLNPYDDGISLDEFVDWLVE
SGHPIQRITDYSDWFHRFETAIRALPEKQRQASVLPLLDAYRNPCPAVRGAILPAKEFQA
AVQTAKIGPEQDIPHLSAPLIDKYVSDLELLQLL

Fig. 11 (continued)

PPTase_222AA (SEQ ID 15)

MIETILPAGVESAELLEYPEDLKAHPAEEHLIAKSVEKRRRDFIGARHCARLALAELGEPPVAIGKGERG
APIWPRGVVGSLTHCDGYRAAAVAHKMRFRSIGIDAEPHATLPEGVLDSVSLPPEREWLKTTDSALHLDR
LLFCAKEATYKAWWPLTARWLGFEEAHITFEIEDGSADSGNGTFHSELLVPGQTNDGGTPLLSFDGRWLI
ADGFILTAIAYA

VAO_560AA (SEQ ID 48)

MSKTQEFRPLTLPPKLSLSDFNEFIQDIIRIVGSENVEVISSKDQIVDGSYMKPTHTHDP
HHVMDQDYFLASAIVAPRNVADVQSIVGLANKFSFPLWPISIGRNSGYGGAAPRVSGSVV
LDMGKNMNRVLEVNVEGAYCVVEPGVTYHDLHNYLEANNLRDKLWLDVPDLGGGSVLGNA
VERGVGYTPYGDHWMMHSGMEVVLANGELLRTGMALPDPKRPETMGLKPEDQPWSKIAH
LFPYGFGPYIDGLFSQSNMGIVTKIGIWLMPNPRGYQSYLITLPKDGDLKQAVDIIRPLR
LGMALQNVPTIRHILLDAAVLGDKRSYSSRTEPLSDEELDKIAKQLNLGRWNFYGALYGP
EPIRRVLWETIKDAFSAIPGVKFYFPEDTPENSVLRVRDKTMQGIPTYDELKWIDWLPNG
AHLFFSPIAKVSGEDAMMQYAVTKKRCQEAGLDFIGTFTVGMREMHHIVCIVFNKKDLIQ
KRKVQWLMRTLIDDCAANGWGEYRTHLAFMDQIMETYNWNNSSFLRFNEVLKNAVDPNGI
IAPGKSGVWPSQYSHVTWKL

SEQUENCE LISTING

```
<160> NUMBER OF SEQ ID NOS: 48

<210> SEQ ID NO 1
<211> LENGTH: 715
<212> TYPE: PRT
<213> ORGANISM: Populus deltoids
```

<400> SEQUENCE: 1

```
Met Glu Thr Val Thr Lys Asn Gly Tyr Gln Asn Gly Ser Leu Glu Ser
1               5                   10                  15

Leu Cys Val Asn Gln Arg Asp Pro Leu Ser Trp Gly Val Ala Ala Glu
            20                  25                  30

Ala Met Lys Gly Ser His Leu Asp Glu Val Lys Arg Met Val Ala Asp
        35                  40                  45

Tyr Arg Lys Pro Val Val Lys Leu Gly Gly Glu Thr Leu Thr Ile Ala
    50                  55                  60

Gln Val Ala Ser Ile Ala Gly His Asp Thr Gly Asp Val Lys Val Glu
65                  70                  75                  80

Leu Ser Glu Ser Ala Arg Pro Gly Val Lys Ala Ser Ser Asp Trp Val
                85                  90                  95

Met Asp Ser Met Asp Lys Gly Thr Asp Ser Tyr Gly Val Thr Thr Gly
            100                 105                 110

Phe Gly Ala Thr Ser His Arg Arg Thr Lys Gln Gly Gly Ala Leu Gln
        115                 120                 125

Lys Glu Leu Ile Arg Phe Leu Asn Ala Gly Ile Phe Gly Asn Gly Thr
    130                 135                 140

Glu Thr Cys His Thr Leu Pro His Ser Ala Thr Arg Ala Ala Met Leu
145                 150                 155                 160

Val Arg Ile Asn Thr Leu Leu Gln Gly Tyr Ser Gly Ile Arg Phe Glu
                165                 170                 175

Ile Leu Glu Ala Ile Thr Arg Leu Leu Asn Asn Asn Ile Thr Pro Cys
            180                 185                 190

Leu Pro Leu Arg Gly Thr Ile Thr Ala Ser Gly Asp Leu Val Pro Leu
        195                 200                 205

Ser Tyr Ile Ala Gly Leu Leu Thr Gly Arg Pro Asn Ser Lys Ala Thr
    210                 215                 220

Gly Pro Thr Gly Glu Val Leu Asp Ala Ala Glu Ala Phe Lys Ala Ala
225                 230                 235                 240

Gly Ile Glu Ser Gly Phe Phe Glu Leu Gln Pro Lys Glu Gly Leu Ala
                245                 250                 255

Leu Val Asn Gly Thr Ala Val Gly Ser Gly Leu Ala Ser Met Val Leu
            260                 265                 270

Phe Glu Thr Asn Val Leu Ala Val Leu Ser Glu Leu Leu Ser Ala Ile
        275                 280                 285

Phe Ala Glu Val Met Asn Gly Lys Pro Glu Phe Thr Asp His Leu Thr
    290                 295                 300

His Lys Leu Lys His His Pro Gly Gln Ile Glu Ala Ala Ile Met
305                 310                 315                 320

Glu His Ile Leu Asp Gly Ser Ala Tyr Met Lys Ala Ala Lys Lys Leu
                325                 330                 335

His Glu Thr Asp Pro Leu Gln Lys Pro Lys Gln Asp Arg Tyr Ala Leu
            340                 345                 350

Arg Thr Ser Pro Gln Trp Leu Gly Pro Gln Ile Glu Val Ile Arg Phe
        355                 360                 365

Ser Thr Lys Ser Ile Glu Arg Glu Ile Asn Ser Val Asn Asp Asn Pro
    370                 375                 380

Leu Ile Asp Val Ser Arg Asn Lys Ala Ile His Gly Gly Asn Phe Gln
385                 390                 395                 400

Gly Thr Pro Ile Gly Val Ser Met Asp Asn Val Arg Leu Ala Ile Ala
                405                 410                 415
```

```
Ser Ile Gly Lys Leu Leu Phe Ala Gln Phe Ser Glu Leu Val Asn Asp
            420                 425                 430

Phe Tyr Asn Asn Gly Leu Pro Ser Asn Leu Thr Ala Ser Arg Asn Pro
            435                 440                 445

Ser Leu Asp Tyr Gly Phe Lys Gly Ala Glu Ile Ala Met Ala Ser Tyr
            450                 455                 460

Cys Ser Glu Leu Gln Tyr Leu Ala Asn Pro Val Thr Thr His Val Gln
465                 470                 475                 480

Ser Ala Glu Gln His Asn Gln Asp Val Asn Ser Leu Gly Leu Ile Ser
                485                 490                 495

Ser Arg Lys Thr Ala Glu Ala Val Asp Ile Leu Lys Leu Met Ser Thr
            500                 505                 510

Thr Phe Leu Val Ala Leu Cys Gln Ala Ile Asp Leu Arg His Leu Glu
            515                 520                 525

Glu Asn Leu Lys Ser Ala Val Lys Asn Thr Val Ser Gln Val Ser Lys
            530                 535                 540

Arg Val Leu Thr Thr Gly Ala Asn Gly Glu Leu His Pro Ser Arg Phe
545                 550                 555                 560

Cys Glu Lys Glu Leu Leu Lys Val Val Asp Arg Glu Tyr Val Phe Ala
                565                 570                 575

Tyr Val Asp Asp Pro Cys Ser Ala Thr Tyr Pro Leu Met Gln Lys Leu
            580                 585                 590

Arg Gln Val Phe Val Asp His Ala Leu Glu Asn Gly Glu Asn Glu Lys
            595                 600                 605

Asn Phe Ser Thr Ser Val Phe Gln Lys Ile Glu Ala Phe Glu Glu Glu
            610                 615                 620

Leu Lys Ala Leu Leu Pro Lys Glu Val Glu Ser Ala Arg Ala Ala Tyr
625                 630                 635                 640

Asp Ser Gly Asn Ser Ala Ile Asp Asn Lys Ile Lys Glu Cys Arg Ser
                645                 650                 655

Tyr Pro Leu Tyr Lys Phe Val Arg Glu Glu Leu Gly Thr Val Leu Leu
            660                 665                 670

Thr Gly Glu Lys Val Gln Ser Pro Gly Glu Glu Phe Asp Lys Val Phe
            675                 680                 685

Thr Ala Met Cys Gln Gly Lys Ile Ile Asp Pro Met Leu Glu Cys Leu
            690                 695                 700

Gly Glu Trp Asn Gly Ser Pro Leu Pro Ile Cys
705                 710                 715

<210> SEQ ID NO 2
<211> LENGTH: 718
<212> TYPE: PRT
<213> ORGANISM: Petroselinum crispum

<400> SEQUENCE: 2

Met Ala Tyr Val Asn Gly Thr Thr Asn Gly His Ala Asn Gly Asn Gly
1               5                   10                  15

Leu Asp Leu Cys Met Lys Lys Glu Asp Pro Leu Asn Trp Gly Val Ala
            20                  25                  30

Ala Glu Ala Leu Thr Gly Ser His Leu Asp Glu Val Lys Arg Met Val
            35                  40                  45

Ala Glu Tyr Arg Lys Pro Val Val Lys Leu Gly Gly Glu Thr Leu Thr
            50                  55                  60

Ile Ser Gln Val Ala Ala Ile Ser Ala Arg Asp Asp Ser Gly Val Lys
```

```
                65                  70                  75                  80
Val Glu Leu Ser Glu Glu Ala Arg Ala Gly Val Lys Ala Ser Ser Asp
                        85                  90                  95
Trp Val Met Asp Ser Met Asn Lys Gly Thr Asp Ser Tyr Gly Val Thr
                       100                 105                 110
Thr Gly Phe Gly Ala Thr Ser His Arg Thr Lys Gln Gly Gly Ala
                       115                 120                 125
Leu Gln Lys Glu Leu Ile Arg Phe Leu Asn Ala Gly Ile Phe Gly Ser
                130                 135                 140
Gly Ala Glu Ala Gly Asn Asn Thr Leu Pro His Ser Ala Thr Arg Ala
145                 150                 155                 160
Ala Met Leu Val Arg Ile Asn Thr Leu Leu Gln Gly Tyr Ser Gly Ile
                       165                 170                 175
Arg Phe Glu Ile Leu Glu Ala Ile Thr Lys Phe Leu Asn His Asn Ile
                       180                 185                 190
Thr Pro Cys Leu Pro Leu Arg Gly Thr Ile Thr Ala Ser Gly Asp Leu
                       195                 200                 205
Val Pro Leu Ser Tyr Ile Ala Gly Leu Leu Thr Gly Arg Pro Asn Ser
                210                 215                 220
Lys Ala Val Gly Pro Thr Gly Val Thr Leu Ser Pro Glu Glu Ala Phe
225                 230                 235                 240
Lys Leu Ala Gly Val Glu Gly Gly Phe Phe Glu Leu Gln Pro Lys Glu
                       245                 250                 255
Gly Leu Ala Leu Val Asn Gly Thr Ala Val Gly Ser Gly Met Ala Ser
                       260                 265                 270
Met Val Leu Phe Glu Ala Asn Ile Leu Ala Val Leu Ala Glu Val Met
                       275                 280                 285
Ser Ala Ile Phe Ala Glu Val Met Gln Gly Lys Pro Glu Phe Thr Asp
                290                 295                 300
His Leu Thr His Lys Leu Lys His His Pro Gly Gln Ile Glu Ala Ala
305                 310                 315                 320
Ala Ile Met Glu His Ile Leu Asp Gly Ser Ala Tyr Val Lys Ala Ala
                       325                 330                 335
Gln Lys Leu His Glu Met Asp Pro Leu Gln Lys Pro Lys Gln Asp Arg
                       340                 345                 350
Tyr Ala Leu Arg Thr Ser Pro Gln Trp Leu Gly Pro Gln Ile Glu Val
                       355                 360                 365
Ile Arg Ser Ser Thr Lys Met Ile Glu Arg Glu Ile Asn Ser Val Asn
                370                 375                 380
Asp Asn Pro Leu Ile Asp Val Ser Arg Asn Lys Ala Ile His Gly Gly
385                 390                 395                 400
Asn Phe Gln Gly Ser Pro Ile Gly Val Ser Met Asp Asn Thr Arg Leu
                       405                 410                 415
Ala Ile Ala Ala Ile Gly Lys Leu Met Phe Ala Gln Phe Ser Glu Leu
                       420                 425                 430
Val Asn Asp Phe Tyr Asn Asn Gly Leu Pro Ser Asn Leu Ser Gly Gly
                       435                 440                 445
Arg Asn Pro Ser Leu Asp Tyr Gly Phe Lys Gly Ala Glu Ile Ala Met
                450                 455                 460
Ala Ser Tyr Cys Ser Glu Leu Gln Phe Leu Ala Asn Pro Val Thr Asn
465                 470                 475                 480
His Val Gln Ser Ala Glu Gln His Asn Gln Asp Val Asn Ser Leu Gly
                       485                 490                 495
```

```
Leu Ile Ser Ser Arg Lys Thr Ser Glu Ala Val Glu Ile Leu Lys Leu
            500                 505                 510

Met Ser Thr Thr Phe Leu Val Gly Leu Cys Gln Ala Ile Asp Leu Arg
            515                 520                 525

His Leu Glu Glu Asn Leu Lys Ser Thr Val Lys Asn Thr Val Ser Gln
        530                 535                 540

Val Ala Lys Arg Val Leu Thr Met Gly Val Asn Gly Glu Leu His Pro
545                 550                 555                 560

Ser Arg Phe Cys Glu Lys Asp Leu Leu Arg Val Val Asp Arg Glu Tyr
                565                 570                 575

Ile Phe Ala Tyr Ile Asp Asp Pro Cys Ser Ala Thr Tyr Pro Leu Met
            580                 585                 590

Gln Lys Leu Arg Glu Thr Leu Val Glu His Ala Leu Asn Asn Gly Asp
        595                 600                 605

Lys Glu Arg Asn Leu Ser Thr Ser Ile Phe Gln Lys Ile Ala Ala Phe
    610                 615                 620

Glu Asp Glu Leu Lys Ala Leu Leu Pro Lys Glu Val Glu Thr Ala Arg
625                 630                 635                 640

Ala Ala Leu Glu Ser Gly Asn Pro Ala Ile Pro Asn Arg Ile Lys Glu
                645                 650                 655

Cys Arg Ser Tyr Pro Leu Tyr Lys Phe Val Arg Glu Glu Leu Gly Thr
            660                 665                 670

Glu Tyr Leu Thr Gly Glu Lys Val Arg Ser Pro Gly Glu Glu Phe Glu
        675                 680                 685

Lys Val Phe Thr Ala Met Ser Lys Gly Glu Ile Ile Asp Pro Leu Leu
    690                 695                 700

Glu Cys Leu Glu Ser Trp Asn Gly Ala Pro Leu Pro Ile Cys
705                 710                 715

<210> SEQ ID NO 3
<211> LENGTH: 506
<212> TYPE: PRT
<213> ORGANISM: Glycine max

<400> SEQUENCE: 3

Met Asp Leu Leu Leu Glu Lys Thr Leu Ile Gly Leu Phe Leu Ala
1               5                   10                  15

Ala Val Val Ala Ile Ala Val Ser Thr Leu Arg Gly Arg Lys Phe Lys
                20                  25                  30

Leu Pro Pro Gly Pro Leu Pro Val Pro Ile Phe Gly Asn Trp Leu Gln
            35                  40                  45

Val Gly Asp Asp Leu Asn His Arg Asn Leu Thr Asp Leu Ala Lys Lys
        50                  55                  60

Phe Gly Asp Ile Phe Leu Leu Arg Met Gly Gln Arg Asn Leu Val Val
65                  70                  75                  80

Val Ser Ser Pro Glu Leu Ala Lys Glu Val Leu His Thr Gln Gly Val
                85                  90                  95

Glu Phe Gly Ser Arg Thr Arg Asn Val Val Phe Asp Ile Phe Thr Gly
            100                 105                 110

Lys Gly Gln Asp Met Val Phe Thr Val Tyr Gly Glu His Trp Arg Lys
        115                 120                 125

Met Arg Arg Ile Met Thr Val Pro Phe Phe Thr Asn Lys Val Val Gln
    130                 135                 140

Gln Tyr Arg His Gly Trp Glu Ser Glu Ala Ala Ala Val Val Glu Asp
```

```
                145                 150                 155                 160
Val Lys Lys Asn Pro Asp Ala Ala Val Ser Gly Thr Val Ile Arg Arg
                    165                 170                 175
Arg Leu Gln Leu Met Met Tyr Asn Asn Met Tyr Arg Ile Met Phe Asp
                    180                 185                 190
Arg Arg Phe Glu Ser Glu Glu Asp Pro Ile Phe Gln Arg Leu Arg Ala
                    195                 200                 205
Leu Asn Gly Glu Arg Ser Arg Leu Ala Gln Ser Phe Glu Tyr Asn Tyr
                    210                 215                 220
Gly Asp Phe Ile Pro Ile Leu Arg Pro Phe Leu Lys Gly Tyr Leu Lys
225                 230                 235                 240
Ile Cys Lys Glu Val Lys Glu Thr Arg Leu Lys Leu Phe Lys Asp Tyr
                    245                 250                 255
Phe Val Asp Glu Arg Lys Lys Leu Gly Ser Thr Lys Ser Thr Asn Asn
                    260                 265                 270
Asn Asn Glu Leu Lys Cys Ala Ile Asp His Ile Leu Asp Ala Gln Arg
                    275                 280                 285
Lys Gly Glu Ile Asn Glu Asp Asn Val Leu Tyr Ile Val Glu Asn Ile
                    290                 295                 300
Asn Val Ala Ala Ile Glu Thr Thr Leu Trp Ser Ile Glu Trp Gly Ile
305                 310                 315                 320
Ala Glu Leu Val Asn His Pro Glu Ile Gln Gln Lys Leu Arg Asp Glu
                    325                 330                 335
Ile Asp Arg Val Leu Gly Ala Gly His Gln Val Thr Glu Pro Asp Ile
                    340                 345                 350
Gln Lys Leu Pro Tyr Leu Gln Ala Val Val Lys Glu Thr Leu Arg Leu
                    355                 360                 365
Arg Met Ala Ile Pro Leu Leu Val Pro His Met Asn Leu His Asp Ala
                    370                 375                 380
Lys Leu Gly Gly Tyr Asp Ile Pro Ala Glu Ser Lys Ile Leu Val Asn
385                 390                 395                 400
Ala Trp Trp Leu Ala Asn Asn Pro Ala His Trp Lys Lys Pro Glu Glu
                    405                 410                 415
Phe Arg Pro Glu Arg Phe Phe Glu Glu Ser Leu Val Glu Ala Asn
                    420                 425                 430
Gly Asn Asp Phe Arg Tyr Leu Pro Phe Gly Val Gly Arg Arg Ser Cys
                    435                 440                 445
Pro Gly Ile Ile Leu Ala Leu Pro Ile Leu Gly Ile Thr Leu Gly Arg
450                 455                 460
Leu Val Gln Asn Phe Glu Leu Leu Pro Pro Pro Gly Gln Ser Gln Ile
465                 470                 475                 480
Asp Thr Ser Glu Lys Gly Gly Gln Phe Ser Leu His Ile Leu Lys His
                    485                 490                 495
Ser Thr Ile Val Ala Lys Pro Arg Ser Phe
                    500                 505

<210> SEQ ID NO 4
<211> LENGTH: 506
<212> TYPE: PRT
<213> ORGANISM: Petroselinum crispum

<400> SEQUENCE: 4

Met Met Asp Phe Val Leu Leu Glu Lys Ala Leu Leu Gly Leu Phe Ile
1               5                   10                  15
```

-continued

```
Ala Thr Ile Val Ala Ile Thr Ile Ser Lys Leu Arg Gly Lys Lys Leu
                 20                  25                  30
Lys Leu Pro Pro Gly Pro Ile Pro Val Pro Val Phe Gly Asn Trp Leu
             35                  40                  45
Gln Val Gly Asp Asp Leu Asn Gln Arg Asn Leu Val Asp Tyr Ala Lys
         50                  55                  60
Lys Phe Gly Asp Leu Phe Met Leu Arg Met Gly Gln Arg Asn Leu Val
65                  70                  75                  80
Val Val Ser Ser Pro Glu Leu Ala Lys Asp Val Leu His Thr Gln Gly
                 85                  90                  95
Val Glu Phe Gly Ser Arg Thr Arg Asn Val Val Phe Asp Ile Phe Thr
            100                 105                 110
Gly Lys Gly Gln Asp Met Val Phe Thr Val Tyr Ser Glu His Trp Arg
        115                 120                 125
Lys Met Arg Arg Ile Met Thr Val Pro Phe Phe Thr Asn Lys Val Val
130                 135                 140
Gln Gln Tyr Arg Phe Gly Trp Glu Asp Glu Ala Ala Arg Val Val Glu
145                 150                 155                 160
Asp Val Lys Ala Asn Pro Glu Ala Ala Thr Asn Gly Ile Val Leu Arg
                165                 170                 175
Asn Arg Leu Gln Leu Leu Met Tyr Asn Asn Met Tyr Arg Ile Met Phe
            180                 185                 190
Asp Arg Arg Phe Glu Ser Val Asp Asp Pro Leu Phe Leu Lys Leu Lys
        195                 200                 205
Ala Leu Asn Gly Glu Arg Ser Arg Leu Ala Gln Ser Phe Glu Tyr His
210                 215                 220
Phe Gly Asp Phe Ile Pro Ile Leu Arg Pro Phe Leu Arg Gly Tyr Leu
225                 230                 235                 240
Lys Leu Cys Gln Glu Ile Lys Asp Lys Arg Leu Lys Leu Phe Lys Asp
                245                 250                 255
Tyr Phe Val Asp Glu Arg Lys Lys Leu Glu Ser Ile Lys Ser Val Asp
            260                 265                 270
Asn Asn Ser Leu Lys Cys Ala Ile Asp His Ile Ile Glu Ala Gln Gln
        275                 280                 285
Lys Gly Glu Ile Asn Glu Asp Asn Val Leu Tyr Ile Val Glu Asn Ile
290                 295                 300
Asn Val Ala Ala Ile Glu Thr Thr Leu Trp Ser Ile Glu Trp Gly Ile
305                 310                 315                 320
Ala Glu Leu Val Asn Asn Pro Glu Ile Gln Lys Lys Leu Arg His Glu
                325                 330                 335
Leu Asp Thr Val Leu Gly Ala Gly Val Gln Ile Cys Glu Pro Asp Val
            340                 345                 350
Gln Lys Leu Pro Tyr Leu Gln Ala Val Ile Lys Glu Thr Leu Arg Tyr
        355                 360                 365
Arg Met Ala Ile Pro Leu Leu Val Pro His Met Asn Leu His Asp Ala
370                 375                 380
Lys Leu Ala Gly Tyr Asp Ile Pro Ala Glu Ser Lys Ile Leu Val Asn
385                 390                 395                 400
Ala Trp Trp Leu Ala Asn Asn Pro Ala His Trp Asn Lys Pro Asp Glu
                405                 410                 415
Phe Arg Pro Glu Arg Phe Leu Glu Glu Ser Lys Val Glu Ala Asn
            420                 425                 430
Gly Asn Asp Phe Lys Tyr Ile Pro Phe Gly Val Gly Arg Arg Ser Cys
```

```
                435                 440                 445
Pro Gly Ile Ile Leu Ala Leu Pro Ile Leu Gly Ile Val Ile Gly Arg
    450                 455                 460
Leu Val Gln Asn Phe Glu Leu Leu Pro Pro Gly Gln Ser Lys Ile
465                 470                 475                 480
Asp Thr Ala Glu Lys Gly Gly Gln Phe Ser Leu Gln Ile Leu Lys His
                485                 490                 495
Ser Thr Ile Val Cys Lys Pro Arg Ser Leu
                500                 505

<210> SEQ ID NO 5
<211> LENGTH: 570
<212> TYPE: PRT
<213> ORGANISM: Populus deltoids

<400> SEQUENCE: 5

Met Met Ser Val Ala Thr Val Glu Pro Pro Lys Pro Glu Leu Ser Pro
1               5                   10                  15
Pro Gln Asn Gln Asn Ala Pro Ser Ser His Glu Thr Asp His Ile Phe
                20                  25                  30
Arg Ser Lys Leu Pro Asp Ile Thr Ile Ser Asn Asp Leu Pro Leu His
            35                  40                  45
Ala Tyr Cys Phe Glu Asn Leu Ser Asp Phe Ser Asp Arg Pro Cys Leu
        50                  55                  60
Ile Ser Gly Ser Thr Gly Lys Thr Tyr Ser Phe Ala Glu Thr His Leu
65                  70                  75                  80
Ile Ser Arg Lys Val Ala Ala Gly Leu Ser Asn Leu Gly Ile Lys Lys
                85                  90                  95
Gly Asp Val Ile Met Thr Leu Leu Gln Asn Cys Pro Glu Phe Val Phe
                100                 105                 110
Ser Phe Ile Gly Ala Ser Met Ile Gly Ala Val Ile Thr Thr Ala Asn
            115                 120                 125
Pro Phe Tyr Thr Gln Ser Glu Ile Phe Lys Gln Phe Ser Ala Ser Arg
        130                 135                 140
Ala Lys Leu Ile Ile Thr Gln Ser Gln Tyr Val Asn Lys Leu Gly Asp
145                 150                 155                 160
Ser Asp Cys His Glu Asn Asn Gln Lys Pro Gly Glu Asp Phe Ile Val
                165                 170                 175
Ile Thr Ile Asp Asp Pro Pro Glu Asn Cys Leu His Phe Asn Val Leu
            180                 185                 190
Val Glu Ala Ser Glu Ser Glu Met Pro Thr Val Ser Ile Leu Pro Asp
        195                 200                 205
Asp Pro Val Ala Leu Pro Phe Ser Ser Gly Thr Thr Gly Leu Pro Lys
210                 215                 220
Gly Val Ile Leu Thr His Lys Ser Leu Ile Thr Ser Val Ala Gln Gln
225                 230                 235                 240
Val Asp Gly Glu Ile Pro Asn Leu Tyr Leu Lys Gln Asp Asp Val Val
                245                 250                 255
Leu Cys Val Leu Pro Leu Phe His Ile Phe Ser Leu Asn Ser Val Leu
            260                 265                 270
Leu Cys Ser Leu Arg Ala Gly Ser Ala Val Leu Leu Met Gln Lys Phe
        275                 280                 285
Glu Ile Gly Ser Leu Leu Glu Leu Ile Gln Lys His Asn Val Ser Val
    290                 295                 300
```

Ala Ala Val Val Pro Pro Leu Val Leu Ala Leu Ala Lys Asn Pro Leu
305                 310                 315                 320

Glu Ala Asn Phe Asp Leu Ser Ser Ile Arg Val Val Leu Ser Gly Ala
            325                 330                 335

Ala Pro Leu Gly Lys Glu Leu Glu Asp Ala Leu Arg Ser Arg Val Pro
            340                 345                 350

Gln Ala Ile Leu Gly Gln Gly Tyr Gly Met Thr Glu Ala Gly Pro Val
        355                 360                 365

Leu Ser Met Cys Leu Ala Phe Ser Lys Gln Pro Phe Pro Thr Lys Ser
370                 375                 380

Gly Ser Cys Gly Thr Val Val Arg Asn Ala Glu Leu Lys Val Ile Asp
385                 390                 395                 400

Pro Glu Thr Gly Arg Ser Leu Gly Tyr Asn Gln Pro Gly Glu Ile Cys
            405                 410                 415

Ile Arg Gly Ser Gln Ile Met Lys Gly Tyr Leu Asn Asp Ala Glu Ala
            420                 425                 430

Thr Ala Asn Thr Ile Asp Val Glu Gly Trp Leu His Thr Gly Asp Ile
            435                 440                 445

Gly Tyr Val Asp Asp Asp Glu Ile Phe Ile Val Asp Arg Val Lys
        450                 455                 460

Glu Ile Ile Lys Phe Lys Gly Phe Gln Val Pro Pro Ala Glu Leu Glu
465                 470                 475                 480

Ala Leu Leu Val Asn His Pro Ser Ile Ala Asp Ala Val Val Pro
            485                 490                 495

Gln Lys Asp Glu Val Ala Gly Glu Val Pro Val Ala Phe Val Val Arg
        500                 505                 510

Ser Asp Asp Leu Asp Leu Ser Glu Glu Ala Val Lys Glu Tyr Ile Ala
        515                 520                 525

Lys Gln Val Val Phe Tyr Lys Lys Leu His Lys Val Phe Phe Val His
530                 535                 540

Ser Ile Pro Lys Ser Ala Ser Gly Lys Ile Leu Arg Lys Asp Leu Arg
545                 550                 555                 560

Ala Lys Leu Ala Thr Ala Thr Thr Met Ser
            565                 570

<210> SEQ ID NO 6
<211> LENGTH: 276
<212> TYPE: PRT
<213> ORGANISM: Pseudomonas fluorescens

<400> SEQUENCE: 6

Met Ser Asn Tyr Glu Gly Arg Trp Thr Thr Val Lys Val Glu Ile Glu
1               5                   10                  15

Asp Gly Ile Ala Trp Val Ile Leu Asn Arg Pro Glu Lys Arg Asn Ala
            20                  25                  30

Met Ser Pro Thr Leu Asn Arg Glu Met Ile Asp Val Leu Glu Thr Leu
        35                  40                  45

Glu Gln Asp Pro Ala Ala Gly Val Leu Val Leu Thr Gly Ala Gly Glu
    50                  55                  60

Ala Trp Thr Ala Gly Met Asp Leu Lys Glu Tyr Phe Arg Glu Val Asp
65                  70                  75                  80

Ala Gly Pro Glu Ile Leu Gln Glu Lys Ile Arg Arg Glu Ala Ser Gln
                85                  90                  95

Trp Gln Trp Lys Leu Leu Arg Met Tyr Ala Lys Pro Thr Ile Ala Met
            100                 105                 110

```
Val Asn Gly Trp Cys Phe Gly Gly Phe Ser Pro Leu Val Ala Cys
        115                 120                 125

Asp Leu Ala Ile Cys Ala Asp Glu Ala Thr Phe Gly Leu Ser Glu Ile
130                 135                 140

Asn Trp Gly Ile Pro Pro Gly Asn Leu Val Ser Lys Ala Met Ala Asp
145                 150                 155                 160

Thr Val Gly His Arg Gln Ser Leu Tyr Tyr Ile Met Thr Gly Lys Thr
                165                 170                 175

Phe Gly Gly Gln Lys Ala Ala Glu Met Gly Leu Val Asn Asp Ser Val
            180                 185                 190

Pro Leu Ala Arg Leu Arg Glu Val Thr Ile Glu Leu Ala Arg Asn Leu
                195                 200                 205

Leu Glu Lys Asn Pro Val Val Leu Arg Ala Ala Lys His Gly Phe Lys
        210                 215                 220

Arg Cys Arg Glu Leu Thr Trp Glu Gln Asn Glu Asp Tyr Leu Tyr Ala
225                 230                 235                 240

Lys Leu Asp Gln Ser Arg Leu Leu Asp Thr Glu Gly Gly Arg Glu Gln
                245                 250                 255

Gly Met Lys Gln Phe Leu Asp Asp Lys Ser Ile Lys Pro Gly Leu Gln
            260                 265                 270

Ala Tyr Lys Arg
            275

<210> SEQ ID NO 7
<211> LENGTH: 276
<212> TYPE: PRT
<213> ORGANISM: Azotobacter vinelandii

<400> SEQUENCE: 7

Met Asn Lys Tyr Glu Gly Arg Trp Lys Thr Val Ile Val Glu Ile Glu
1               5                   10                  15

Gly Gly Ile Ala Trp Val Thr Leu Asn Arg Pro Asp Lys Arg Asn Ala
            20                  25                  30

Met Ser Pro Thr Leu Asn Arg Glu Met Arg Asp Val Leu Glu Thr Leu
        35                  40                  45

Glu Gln Asp Pro Ala Ala Arg Val Leu Val Leu Thr Gly Ala Gly Ser
    50                  55                  60

Ala Trp Thr Ala Gly Met Asp Leu Lys Glu Tyr Phe Arg Glu Val Asp
65                  70                  75                  80

Ala Gly Pro Glu Ile Leu Gln Glu Lys Ile Arg Arg Glu Ala Cys Glu
                85                  90                  95

Trp Gln Trp Lys Leu Leu Arg Met Tyr Ala Lys Pro Thr Val Ala Met
            100                 105                 110

Val Asn Gly Trp Cys Phe Gly Gly Phe Ser Pro Leu Val Ala Cys
        115                 120                 125

Asp Leu Ala Ile Cys Ala Asp Glu Ala Thr Phe Gly Leu Ser Glu Ile
130                 135                 140

Asn Trp Gly Ile Pro Pro Gly Asn Leu Val Ser Lys Ala Met Ala Asp
145                 150                 155                 160

Thr Val Gly His Arg Gln Ala Leu Tyr Tyr Ile Met Thr Gly Lys Thr
                165                 170                 175

Phe Asp Gly Arg Gln Ala Ala Glu Met Gly Leu Val Asn Gln Ser Val
            180                 185                 190

Pro Leu Ala Gln Leu Arg Glu Thr Val Ala Thr Leu Cys Gln Asp Leu
```

```
                195                 200                 205
Leu Asp Lys Asn Pro Val Val Leu Arg Ala Ala Lys Asn Gly Phe Lys
    210                 215                 220

Arg Cys Arg Glu Leu Thr Trp Glu Gln Asn Glu Asp Tyr Leu Tyr Ala
225                 230                 235                 240

Lys Leu Asp Gln Ser Arg Leu Leu Asp Glu Glu Gly Arg Glu
                245                 250                 255

Gly Met Arg Gln Phe Leu Asp Glu Lys Ser Ile Lys Pro Gly Leu Gln
            260                 265                 270

Ala Tyr Lys Arg
        275

<210> SEQ ID NO 8
<211> LENGTH: 394
<212> TYPE: PRT
<213> ORGANISM: Pseudomonas aeruginosa

<400> SEQUENCE: 8

Met Lys Thr Gln Val Ala Ile Ile Gly Ala Gly Pro Ser Gly Leu Leu
1               5                   10                  15

Leu Gly Gln Leu Leu His Lys Ala Gly Ile Asp Asn Val Ile Leu Glu
            20                  25                  30

Arg Gln Thr Pro Asp Tyr Val Leu Gly Arg Ile Arg Ala Gly Val Leu
        35                  40                  45

Glu Gln Gly Met Val Asp Leu Leu Arg Glu Ala Gly Val Asp Arg Arg
    50                  55                  60

Met Ala Arg Asp Gly Leu Val His Glu Gly Val Glu Ile Ala Phe Ala
65                  70                  75                  80

Gly Gln Arg Arg Arg Ile Asp Leu Lys Arg Leu Ser Gly Gly Lys Thr
                85                  90                  95

Val Thr Val Tyr Gly Gln Thr Glu Val Thr Arg Asp Leu Met Glu Ala
            100                 105                 110

Arg Glu Ala Cys Gly Ala Thr Thr Val Tyr Gln Ala Ala Glu Val Arg
        115                 120                 125

Leu His Asp Leu Gln Gly Glu Arg Pro Tyr Val Thr Phe Glu Arg Asp
    130                 135                 140

Gly Glu Arg Leu Arg Leu Asp Cys Asp Tyr Ile Ala Gly Cys Asp Gly
145                 150                 155                 160

Phe His Gly Ile Ser Arg Gln Ser Ile Pro Ala Glu Arg Leu Lys Val
                165                 170                 175

Phe Glu Arg Val Tyr Pro Phe Gly Trp Leu Gly Leu Leu Ala Asp Thr
            180                 185                 190

Pro Pro Val Ser His Glu Leu Ile Tyr Ala Asn His Pro Arg Gly Phe
        195                 200                 205

Ala Leu Cys Ser Gln Arg Ser Ala Thr Arg Ser Arg Tyr Tyr Val Gln
    210                 215                 220

Val Pro Leu Thr Glu Lys Val Glu Asp Trp Ser Asp Glu Arg Phe Trp
225                 230                 235                 240

Thr Glu Leu Lys Ala Arg Leu Pro Ala Glu Val Ala Glu Lys Leu Val
                245                 250                 255

Thr Gly Pro Ser Leu Glu Lys Ser Ile Ala Pro Leu Arg Ser Phe Val
            260                 265                 270

Val Glu Pro Met Gln His Gly Arg Leu Phe Leu Ala Gly Asp Ala Ala
        275                 280                 285
```

```
His Ile Val Pro Pro Thr Gly Ala Lys Gly Leu Asn Leu Ala Ala Ser
    290                 295                 300

Asp Val Ser Thr Leu Tyr Arg Leu Leu Leu Lys Ala Tyr Arg Glu Gly
305                 310                 315                 320

Arg Gly Glu Leu Leu Glu Arg Tyr Ser Ala Ile Cys Leu Arg Arg Ile
                325                 330                 335

Trp Lys Ala Glu Arg Phe Ser Trp Trp Met Thr Ser Val Leu His Arg
                340                 345                 350

Phe Pro Asp Thr Asp Ala Phe Ser Gln Arg Ile Gln Gln Thr Glu Leu
                355                 360                 365

Glu Tyr Tyr Leu Gly Ser Glu Ala Gly Leu Ala Thr Ile Ala Glu Asn
370                 375                 380

Tyr Val Gly Leu Pro Tyr Glu Glu Ile Glu
385                 390

<210> SEQ ID NO 9
<211> LENGTH: 394
<212> TYPE: PRT
<213> ORGANISM: Azotobacter vinelandii

<400> SEQUENCE: 9

Met Lys Thr Gln Val Ala Ile Ile Gly Ala Gly Pro Ser Gly Leu Leu
1               5                   10                  15

Leu Gly Gln Leu Leu His Lys Ala Gly Ile Asp Asn Val Ile Leu Glu
                20                  25                  30

Arg His Ser Pro Asp Tyr Val Leu Gly Arg Ile Arg Ala Gly Val Leu
            35                  40                  45

Glu Gln Gly Val Val Asp Leu Leu Arg Glu Ala Gly Val Ala Glu Arg
 50                 55                  60

Met Asp Arg Glu Gly Leu Val His Glu Gly Ile Glu Leu Ala Cys Ser
65                  70                  75                  80

Gly Arg Arg Ile Arg Leu Asp Leu Lys Ala Leu Ser Gly Gly Lys Thr
                85                  90                  95

Val Met Val Tyr Gly Gln Thr Glu Val Thr Arg Asp Leu Met Asp Ala
                100                 105                 110

Arg Arg Ala Ser Gly Ala Pro Ile Val Tyr Glu Ala Gln Asn Val Arg
            115                 120                 125

Leu Ser Gly Leu Lys Asp Gly Met Pro His Val Thr Tyr Glu Lys Asp
130                 135                 140

Gly Gln Thr His Arg Leu Asp Cys Asp Tyr Ile Ala Gly Cys Asp Gly
145                 150                 155                 160

Phe His Gly Val Ser Arg Gln Ser Ile Pro Ala Glu Ala Leu Ser His
                165                 170                 175

Tyr Glu Arg Val Tyr Pro Phe Gly Trp Leu Gly Leu Leu Ser Asp Thr
                180                 185                 190

Pro Pro Val His Glu Glu Leu Ile Tyr Ala His Thr Asp Leu Gly Phe
            195                 200                 205

Val Leu Cys Ser Gln Arg Ser Pro Thr Arg Ser Arg Tyr Tyr Leu Gln
210                 215                 220

Val Pro Leu Ser Asp Arg Val Glu Asp Trp Ser Asp Glu Arg Phe Trp
225                 230                 235                 240

Asn Glu Leu Lys Arg Arg Leu Pro Gly Asp Val Ala Asn Arg Leu Val
                245                 250                 255

Thr Gly Pro Ser Leu Glu Lys Ser Ile Ala Pro Leu Arg Ser Tyr Val
                260                 265                 270
```

```
Val Glu Pro Met Gln Tyr Gly Arg Leu Phe Leu Val Gly Asp Ala Ala
            275                 280                 285

His Ile Val Pro Pro Thr Gly Ala Lys Gly Leu Asn Leu Ala Gly Ser
    290                 295                 300

Asp Val Cys Tyr Leu Tyr Arg Ile Leu Leu Lys Val Tyr Arg Glu Gly
305                 310                 315                 320

Arg Thr Glu Leu Leu Glu Lys Tyr Ser Glu Leu Ala Leu Arg Arg Val
                325                 330                 335

Trp Lys Gly Glu Arg Phe Ser Trp Phe Met Thr Asn Leu Leu His Asp
            340                 345                 350

Phe Glu Gly Ser Asp Ala Phe Asp Arg Arg Met Gln Leu Ala Asp Arg
            355                 360                 365

Asp Tyr Tyr Leu Asp Ser Glu Ala Gly Arg Val Thr Ile Ala Glu Asn
    370                 375                 380

Tyr Val Gly Leu Pro Tyr Glu Glu Ile Ala
385                 390

<210> SEQ ID NO 10
<211> LENGTH: 365
<212> TYPE: PRT
<213> ORGANISM: Medicago sativa

<400> SEQUENCE: 10

Met Gly Ser Thr Gly Glu Thr Gln Ile Thr Pro Thr His Ile Ser Asp
1               5                   10                  15

Glu Glu Ala Asn Leu Phe Ala Met Gln Leu Ala Ser Ala Ser Val Leu
            20                  25                  30

Pro Met Ile Leu Lys Ser Ala Leu Glu Leu Asp Leu Leu Glu Ile Ile
        35                  40                  45

Ala Lys Ala Gly Pro Gly Ala Gln Ile Ser Pro Ile Glu Ile Ala Ser
    50                  55                  60

Gln Leu Pro Thr Thr Asn Pro Asp Ala Pro Val Met Leu Asp Arg Met
65                  70                  75                  80

Leu Arg Leu Leu Ala Cys Tyr Asn Ile Leu Thr Cys Ser Val Arg Thr
                85                  90                  95

Gln Gln Asp Gly Lys Val Gln Arg Leu Tyr Gly Leu Ala Thr Val Ala
            100                 105                 110

Lys Tyr Leu Val Lys Asn Glu Asp Gly Val Ser Ile Ser Ala Leu Asn
        115                 120                 125

Leu Met Asn Gln Asp Lys Val Leu Met Glu Ser Trp Tyr His Leu Lys
    130                 135                 140

Asp Ala Val Leu Asp Gly Gly Ile Pro Phe Asn Lys Ala Tyr Gly Met
145                 150                 155                 160

Thr Ala Phe Glu Tyr His Gly Thr Asp Pro Arg Phe Asn Lys Val Phe
                165                 170                 175

Asn Lys Gly Met Ser Asp His Ser Thr Ile Thr Met Lys Lys Ile Leu
            180                 185                 190

Glu Thr Tyr Thr Gly Phe Glu Gly Leu Lys Ser Leu Val Asp Val Gly
        195                 200                 205

Gly Gly Thr Gly Ala Val Ile Asn Thr Ile Val Ser Lys Tyr Pro Thr
    210                 215                 220

Ile Lys Gly Ile Asn Phe Asp Leu Pro His Val Ile Glu Asp Ala Pro
225                 230                 235                 240

Ser Tyr Pro Gly Val Glu His Val Gly Gly Asp Met Phe Val Ser Ile
```

```
                     245                 250                 255
Pro Lys Ala Asp Ala Val Phe Met Lys Trp Ile Cys His Asp Trp Ser
                 260                 265                 270
Asp Glu His Cys Leu Lys Phe Leu Lys Asn Cys Tyr Glu Ala Leu Pro
             275                 280                 285
Asp Asn Gly Lys Val Ile Val Ala Glu Cys Ile Leu Pro Val Ala Pro
         290                 295                 300
Asp Ser Ser Leu Ala Thr Lys Gly Val Val His Ile Asp Val Ile Met
305                 310                 315                 320
Leu Ala His Asn Pro Gly Gly Lys Glu Arg Thr Gln Lys Glu Phe Glu
                 325                 330                 335
Asp Leu Ala Lys Gly Ala Gly Phe Gln Gly Phe Lys Val His Cys Asn
             340                 345                 350
Ala Phe Asn Thr Tyr Ile Met Glu Phe Leu Lys Lys Val
         355                 360                 365

<210> SEQ ID NO 11
<211> LENGTH: 365
<212> TYPE: PRT
<213> ORGANISM: Vanilla planifolia

<400> SEQUENCE: 11

Met Ala Thr Trp Val Glu His Gln Gln Gln Asn Gly Ser Lys Asp
1               5                   10                  15
Val Asp Glu Glu Ala Cys Met Tyr Ala Met Gln Leu Ser Ser Met Val
                 20                  25                  30
Val Leu Pro Met Thr Leu Arg Val Ala Val Glu Leu Gly Ile Leu Glu
             35                  40                  45
Gln Ile Gln Ala Gly Gly Pro Asp Ser Tyr Leu Thr Ala Glu Asp Leu
         50                  55                  60
Ala Ala Arg Leu Gly Asn Ser Asn Pro Leu Ala Pro Val Met Ile Glu
65                  70                  75                  80
Arg Ile Leu Arg Leu Leu Thr Ser Tyr Ser Ile Leu Asn Phe Thr Asp
                 85                  90                  95
Thr Val Asp Gly Glu Gly Arg Thr Val Arg Ser Tyr Gly Ala Ala His
             100                 105                 110
Val Cys Lys Tyr Leu Thr Pro Asn Gln Asp Gly Val Ser Met Ala Pro
         115                 120                 125
Leu Val Leu Met Asn Thr Asp Lys Val Leu Met Glu Ser Trp Tyr His
130                 135                 140
Met Lys Asp Ala Val Thr Asn Gly Gly Ile Pro Phe Asn Leu Ala Tyr
145                 150                 155                 160
Gly Met Thr Ala Phe Glu Tyr His Gly Lys Asp Leu Arg Phe Asn Lys
                 165                 170                 175
Val Phe Asn Glu Gly Met Lys Asn Ser Ile Ile Ile Thr Lys Lys
             180                 185                 190
Ile Leu Glu Arg Tyr Lys Arg Phe Glu Asp Val Asn Val Leu Ile Asp
         195                 200                 205
Val Gly Gly Gly Ile Gly Thr Ile Ser Met Ile Thr Ala Lys Tyr
210                 215                 220
Pro His Ile His Gly Ile Asn Phe Asp Leu Pro His Val Val Ser Glu
225                 230                 235                 240
Ala Pro Pro Phe Gln Gly Val Glu His Val Gly Gly Asn Met Phe Glu
                 245                 250                 255
```

```
Ser Val Pro Ile Gly Asp Ala Ile Phe Ile Lys Trp Ile Leu His Asp
                260                 265                 270

Trp Ser Asp Glu His Cys Leu Lys Leu Leu Arg Asn Cys Ala Lys Ser
            275                 280                 285

Leu Pro Asp Lys Gly Lys Val Ile Val Glu Cys Ile Leu Pro Asp
290                 295                 300

Ala Pro Leu Val Thr Pro Glu Ala Glu Gly Val Phe His Leu Asp Met
305                 310                 315                 320

Ile Met Leu Ala His Asn Pro Gly Gly Lys Arg Thr Lys Lys Glu
                325                 330                 335

Phe Lys Glu Leu Ala Met Leu Ser Gly Phe Ser Asn Phe Lys Ala Leu
            340                 345                 350

Phe Ser Tyr Ala Asn Val Trp Val Met Glu Phe Asn Lys
            355                 360                 365

<210> SEQ ID NO 12
<211> LENGTH: 524
<212> TYPE: PRT
<213> ORGANISM: Geobacillus thermoleovorans

<400> SEQUENCE: 12

Met Thr Val Lys Gln Lys Asn Gly Val Arg Pro Phe Thr Gly Glu Glu
1               5                   10                  15

Tyr Leu Glu Ser Leu Arg Asp Gly Arg Glu Val Tyr Val Tyr Gly Glu
            20                  25                  30

Arg Val Lys Asp Ile Thr Thr His Pro Ala Tyr Arg Asn Ala Ala Arg
        35                  40                  45

Met Phe Ala Arg Trp Tyr Asp Arg Leu His Gln Leu His Ala Glu Asp
    50                  55                  60

Glu Gln Arg Gly Gly Pro Glu Asn Trp Lys Trp Thr Val Pro Thr Asp
65                  70                  75                  80

Thr Gly Asn Gly Gly Trp Thr His Pro Tyr Phe Ile Gly Ala Arg Cys
                85                  90                  95

Ala Glu Asp Leu Ile Lys Gly Arg Asp Thr Ile Ala Glu Leu Gln Arg
            100                 105                 110

Val Val Tyr Gly Trp Leu Gly Arg Ser Pro Asp Tyr Lys Ala Ala Phe
        115                 120                 125

Val Gly Thr Leu Gly Ala Asn Ser Asn Phe Tyr Ala Pro Tyr Gln Glu
    130                 135                 140

Asn Ala Lys Arg Trp Tyr Asn Glu Thr Gln Glu Arg Leu Leu Phe Trp
145                 150                 155                 160

Asn His Ala Ile Val Asn Pro Pro Val Asp Arg Asn Lys Pro Ile Glu
                165                 170                 175

Glu Val Gly Asp Val Phe Met His Val Glu Lys Glu Thr Asp Ala Gly
            180                 185                 190

Val Val Val Ser Gly Ala Lys Val Val Ala Thr Gly Ser Ala Leu Thr
        195                 200                 205

His Met Asn Phe Ile Gly Gln Tyr Gly Pro Val Pro Val Lys Asp Lys
    210                 215                 220

Lys Phe Ala Leu Ile Phe Thr Val Pro Met Asn Ala Pro Gly Val Lys
225                 230                 235                 240

Leu Ile Ser Arg Ala Ser Tyr Glu Phe Val Ala Ala Thr Gly Ser
                245                 250                 255

Pro Phe Asp Tyr Pro Leu Ser Ser Arg Leu Asp Glu Asn Asp Ala Ile
            260                 265                 270
```

```
Leu Val Phe Asp Lys Val Leu Pro Trp Glu Asn Ile Phe Val Tyr
            275                 280                 285

Glu Asp Val Glu Lys Val Asn Thr Phe Phe Pro Arg Ser Gly Phe Ile
290                 295                 300

Asn Arg Phe Thr Leu His Gly Leu Thr Arg Leu Ala Val Lys Leu Asp
305                 310                 315                 320

Phe Ile Ala Gly Leu Val Leu Lys Ala Thr Glu Ala Thr Gly Val Lys
                325                 330                 335

Asp Phe Arg Gly Val Gln Ala Arg Val Gly Glu Ile Leu Ala Trp Arg
                340                 345                 350

His Leu Phe Trp Ser Leu Ser Glu Ala Gln Val Arg Asn Pro Glu Pro
                355                 360                 365

Trp Val Asp Asp Tyr Val Leu Pro Asn Leu Ser Ala Gly Leu Ala Tyr
                370                 375                 380

Arg Val Phe Ala Ser Glu Ala Tyr Pro Lys Ile Lys Asp Leu Ile Glu
385                 390                 395                 400

Lys Asp Leu Ala Ser Ser Leu Ile Tyr Leu Pro Ser Asn Ala Ala Asp
                405                 410                 415

Phe Leu Glu Pro Glu Ile Arg Pro Tyr Leu Glu Lys Tyr Val Arg Gly
                420                 425                 430

Ser Asn Gly Tyr Asp Ala Glu Ser Arg Val Lys Leu Leu Lys Leu Leu
                435                 440                 445

Trp Asp Ala Val Gly Ser Glu Phe Gly Gly Arg His Glu Leu Tyr Glu
                450                 455                 460

Arg Asn Tyr Ala Gly Asn His Glu Asn Ile Arg Leu Glu Val Leu Leu
465                 470                 475                 480

Thr Ala Leu Asn Thr Gly Asp Ala Asp Arg Phe Lys Glu Phe Ala Glu
                485                 490                 495

Gln Cys Met Asp Glu Tyr Asp Leu Asn Gly Trp Lys Val Pro Asp Leu
                500                 505                 510

Ile Asn Pro Asp Asp Val Asn Ile Ile Arg Lys Arg
                515                 520

<210> SEQ ID NO 13
<211> LENGTH: 146
<212> TYPE: PRT
<213> ORGANISM: Geobacillus thermoleovorans

<400> SEQUENCE: 13

Met Gly Lys Phe Ala Thr Gly Val Thr Val Thr Thr Glu Phe Gln
1               5                   10                  15

Gly Glu Ala Lys Gly Met Thr Ala Asn Ala Phe Met Ser Val Ser Leu
                20                  25                  30

Asp Pro Lys Leu Val Val Ser Ile Gly His Lys Ala Arg Met His
            35                  40                  45

Asp Ile Val Lys Gln Thr Gly Lys Phe Ala Val Asn Ile Leu Arg Arg
50                  55                  60

Asp Gln Glu Glu Leu Ser Arg Leu Phe Ala Gly Gln Leu Lys Glu Glu
65                  70                  75                  80

Arg His Val Ser Phe Asp Trp Val Asn Gly His Pro Ile Leu Pro Glu
                85                  90                  95

Ala Leu Ala Asn Ile Leu Cys Asn Val His Ser Thr Tyr Val Ala Gly
                100                 105                 110

Asp His Thr Leu Tyr Phe Gly Glu Val Thr Asp Ile Leu Met Lys Asp
```

```
                    115                 120                 125
Glu Pro Gly Asp Pro Leu Leu Phe Glu Gly Lys Tyr Arg Ser Ile
    130                 135                 140
Gly Gln
145

<210> SEQ ID NO 14
<211> LENGTH: 1174
<212> TYPE: PRT
<213> ORGANISM: Nocardia iowensis

<400> SEQUENCE: 14

Met Ala Val Asp Ser Pro Asp Glu Arg Leu Gln Arg Arg Ile Ala Gln
1               5                   10                  15

Leu Phe Ala Glu Asp Glu Gln Val Lys Ala Ala Arg Pro Leu Glu Ala
                20                  25                  30

Val Ser Ala Ala Val Ser Ala Pro Gly Met Arg Leu Ala Gln Ile Ala
            35                  40                  45

Ala Thr Val Met Ala Gly Tyr Ala Asp Arg Pro Ala Ala Gly Gln Arg
        50                  55                  60

Ala Phe Glu Leu Asn Thr Asp Asp Ala Thr Gly Arg Thr Ser Leu Arg
65                  70                  75                  80

Leu Leu Pro Arg Phe Glu Thr Ile Thr Tyr Arg Glu Leu Trp Gln Arg
                85                  90                  95

Val Gly Glu Val Ala Ala Ala Trp His His Asp Pro Glu Asn Pro Leu
            100                 105                 110

Arg Ala Gly Asp Phe Val Ala Leu Leu Gly Phe Thr Ser Ile Asp Tyr
        115                 120                 125

Ala Thr Leu Asp Leu Ala Asp Ile His Leu Gly Ala Val Thr Val Pro
    130                 135                 140

Leu Gln Ala Ser Ala Ala Val Ser Gln Leu Ile Ala Ile Leu Thr Glu
145                 150                 155                 160

Thr Ser Pro Arg Leu Leu Ala Ser Thr Pro Glu His Leu Asp Ala Ala
                165                 170                 175

Val Glu Cys Leu Leu Ala Gly Thr Thr Pro Glu Arg Leu Val Val Phe
            180                 185                 190

Asp Tyr His Pro Glu Asp Asp Gln Arg Ala Ala Phe Glu Ser Ala
        195                 200                 205

Arg Arg Arg Leu Ala Asp Ala Gly Ser Leu Val Ile Val Glu Thr Leu
    210                 215                 220

Asp Ala Val Arg Ala Arg Gly Arg Asp Leu Pro Ala Ala Pro Leu Phe
225                 230                 235                 240

Val Pro Asp Thr Asp Asp Asp Pro Leu Ala Leu Leu Ile Tyr Thr Ser
                245                 250                 255

Gly Ser Thr Gly Thr Pro Lys Gly Ala Met Tyr Thr Asn Arg Leu Ala
                260                 265                 270

Ala Thr Met Trp Gln Gly Asn Ser Met Leu Gln Gly Asn Ser Gln Arg
        275                 280                 285

Val Gly Ile Asn Leu Asn Tyr Met Pro Met Ser His Ile Ala Gly Arg
    290                 295                 300

Ile Ser Leu Phe Gly Val Leu Ala Arg Gly Gly Thr Ala Tyr Phe Ala
305                 310                 315                 320

Ala Lys Ser Asp Met Ser Thr Leu Phe Glu Asp Ile Gly Leu Val Arg
                325                 330                 335
```

-continued

```
Pro Thr Glu Ile Phe Phe Val Pro Arg Val Cys Asp Met Val Phe Gln
            340                 345                 350

Arg Tyr Gln Ser Glu Leu Asp Arg Arg Ser Val Ala Gly Ala Asp Leu
        355                 360                 365

Asp Thr Leu Asp Arg Glu Val Lys Ala Asp Leu Arg Gln Asn Tyr Leu
    370                 375                 380

Gly Gly Arg Phe Leu Val Ala Val Val Gly Ser Ala Pro Leu Ala Ala
385                 390                 395                 400

Glu Met Lys Thr Phe Met Glu Ser Val Leu Asp Leu Pro Leu His Asp
                405                 410                 415

Gly Tyr Gly Ser Thr Glu Ala Gly Ala Ser Val Leu Leu Asp Asn Gln
            420                 425                 430

Ile Gln Arg Pro Pro Val Leu Asp Tyr Lys Leu Val Asp Val Pro Glu
        435                 440                 445

Leu Gly Tyr Phe Arg Thr Asp Arg Pro His Pro Arg Gly Glu Leu Leu
    450                 455                 460

Leu Lys Ala Glu Thr Thr Ile Pro Gly Tyr Tyr Lys Arg Pro Glu Val
465                 470                 475                 480

Thr Ala Glu Ile Phe Asp Glu Asp Gly Phe Tyr Lys Thr Gly Asp Ile
                485                 490                 495

Val Ala Glu Leu Glu His Asp Arg Leu Val Tyr Val Asp Arg Arg Asn
            500                 505                 510

Asn Val Leu Lys Leu Ser Gln Gly Glu Phe Val Thr Val Ala His Leu
        515                 520                 525

Glu Ala Val Phe Ala Ser Ser Pro Leu Ile Arg Gln Ile Phe Ile Tyr
    530                 535                 540

Gly Ser Ser Glu Arg Ser Tyr Leu Leu Ala Val Ile Val Pro Thr Asp
545                 550                 555                 560

Asp Ala Leu Arg Gly Arg Asp Thr Ala Thr Leu Lys Ser Ala Leu Ala
                565                 570                 575

Glu Ser Ile Gln Arg Ile Ala Lys Asp Ala Asn Leu Gln Pro Tyr Glu
            580                 585                 590

Ile Pro Arg Asp Phe Leu Ile Glu Thr Glu Pro Phe Thr Ile Ala Asn
        595                 600                 605

Gly Leu Leu Ser Gly Ile Ala Lys Leu Leu Arg Pro Asn Leu Lys Glu
    610                 615                 620

Arg Tyr Gly Ala Gln Leu Glu Gln Met Tyr Thr Asp Leu Ala Thr Gly
625                 630                 635                 640

Gln Ala Asp Glu Leu Leu Ala Leu Arg Arg Glu Ala Ala Asp Leu Pro
                645                 650                 655

Val Leu Glu Thr Val Ser Arg Ala Ala Lys Ala Met Leu Gly Val Ala
            660                 665                 670

Ser Ala Asp Met Arg Pro Asp Ala His Phe Thr Asp Leu Gly Gly Asp
        675                 680                 685

Ser Leu Ser Ala Leu Ser Phe Ser Asn Leu Leu His Glu Ile Phe Gly
    690                 695                 700

Val Glu Val Pro Val Gly Val Val Ser Pro Ala Asn Glu Leu Arg
705                 710                 715                 720

Asp Leu Ala Asn Tyr Ile Glu Ala Glu Arg Asn Ser Gly Ala Lys Arg
                725                 730                 735

Pro Thr Phe Thr Ser Val His Gly Gly Gly Ser Glu Ile Arg Ala Ala
            740                 745                 750

Asp Leu Thr Leu Asp Lys Phe Ile Asp Ala Arg Thr Leu Ala Ala Ala
```

```
              755                760                765
Asp Ser Ile Pro His Ala Pro Val Pro Ala Gln Thr Val Leu Leu Thr
770                775                780

Gly Ala Asn Gly Tyr Leu Gly Arg Phe Leu Cys Leu Glu Trp Leu Glu
785                790                795                800

Arg Leu Asp Lys Thr Gly Gly Thr Leu Ile Cys Val Val Arg Gly Ser
                   805                810                815

Asp Ala Ala Ala Ala Arg Lys Arg Leu Asp Ser Ala Phe Asp Ser Gly
                   820                825                830

Asp Pro Gly Leu Leu Glu His Tyr Gln Gln Leu Ala Ala Arg Thr Leu
                   835                840                845

Glu Val Leu Ala Gly Asp Ile Gly Asp Pro Asn Leu Gly Leu Asp Asp
850                855                860

Ala Thr Trp Gln Arg Leu Ala Glu Thr Val Asp Leu Ile Val His Pro
865                870                875                880

Ala Ala Leu Val Asn His Val Leu Pro Tyr Thr Gln Leu Phe Gly Pro
                   885                890                895

Asn Val Val Gly Thr Ala Glu Ile Val Arg Leu Ala Ile Thr Ala Arg
                   900                905                910

Arg Lys Pro Val Thr Tyr Leu Ser Thr Val Gly Val Ala Asp Gln Val
                   915                920                925

Asp Pro Ala Glu Tyr Gln Glu Asp Ser Asp Val Arg Glu Met Ser Ala
930                935                940

Val Arg Val Val Arg Glu Ser Tyr Ala Asn Gly Tyr Gly Asn Ser Lys
945                950                955                960

Trp Ala Gly Glu Val Leu Leu Arg Glu Ala His Asp Leu Cys Gly Leu
                   965                970                975

Pro Val Ala Val Phe Arg Ser Asp Met Ile Leu Ala His Ser Arg Tyr
                   980                985                990

Ala Gly Gln Leu Asn Val Gln Asp Val Phe Thr Arg Leu Ile Leu Ser
                   995                1000               1005

Leu Val Ala Thr Gly Ile Ala Pro Tyr Ser Phe Tyr Arg Thr Asp
         1010               1015               1020

Ala Asp Gly Asn Arg Gln Arg Ala His Tyr Asp Gly Leu Pro Ala
         1025               1030               1035

Asp Phe Thr Ala Ala Ala Ile Thr Ala Leu Gly Ile Gln Ala Thr
         1040               1045               1050

Glu Gly Phe Arg Thr Tyr Asp Val Leu Asn Pro Tyr Asp Asp Gly
         1055               1060               1065

Ile Ser Leu Asp Glu Phe Val Asp Trp Leu Val Glu Ser Gly His
         1070               1075               1080

Pro Ile Gln Arg Ile Thr Asp Tyr Ser Asp Trp Phe His Arg Phe
         1085               1090               1095

Glu Thr Ala Ile Arg Ala Leu Pro Glu Lys Gln Arg Gln Ala Ser
         1100               1105               1110

Val Leu Pro Leu Leu Asp Ala Tyr Arg Asn Pro Cys Pro Ala Val
         1115               1120               1125

Arg Gly Ala Ile Leu Pro Ala Lys Glu Phe Gln Ala Ala Val Gln
         1130               1135               1140

Thr Ala Lys Ile Gly Pro Glu Gln Asp Ile Pro His Leu Ser Ala
         1145               1150               1155

Pro Leu Ile Asp Lys Tyr Val Ser Asp Leu Glu Leu Leu Gln Leu
         1160               1165               1170
```

Leu

<210> SEQ ID NO 15
<211> LENGTH: 222
<212> TYPE: PRT
<213> ORGANISM: Nocardia iowensis

<400> SEQUENCE: 15

Met Ile Glu Thr Ile Leu Pro Ala Gly Val Glu Ser Ala Glu Leu Leu
1               5                   10                  15

Glu Tyr Pro Glu Asp Leu Lys Ala His Pro Ala Glu Glu His Leu Ile
            20                  25                  30

Ala Lys Ser Val Glu Lys Arg Arg Asp Phe Ile Gly Ala Arg His
        35                  40                  45

Cys Ala Arg Leu Ala Leu Ala Glu Leu Gly Pro Pro Val Ala Ile
    50                  55                  60

Gly Lys Gly Glu Arg Gly Ala Pro Ile Trp Pro Arg Gly Val Val Gly
65                  70                  75                  80

Ser Leu Thr His Cys Asp Gly Tyr Arg Ala Ala Val Ala His Lys
                85                  90                  95

Met Arg Phe Arg Ser Ile Gly Ile Asp Ala Glu Pro His Ala Thr Leu
                100                 105                 110

Pro Glu Gly Val Leu Asp Ser Val Ser Leu Pro Pro Gly Arg Glu Trp
            115                 120                 125

Leu Lys Thr Thr Asp Ser Ala Leu His Leu Asp Arg Leu Leu Phe Cys
    130                 135                 140

Ala Lys Glu Ala Thr Tyr Lys Ala Trp Trp Pro Leu Thr Ala Arg Trp
145                 150                 155                 160

Leu Gly Phe Glu Glu Ala His Ile Thr Phe Glu Ile Glu Asp Gly Ser
                165                 170                 175

Ala Asp Ser Gly Asn Gly Thr Phe His Ser Glu Leu Leu Val Pro Gly
            180                 185                 190

Gln Thr Asn Asp Gly Gly Thr Pro Leu Leu Ser Phe Asp Gly Arg Trp
        195                 200                 205

Leu Ile Ala Asp Gly Phe Ile Leu Thr Ala Ile Ala Tyr Ala
    210                 215                 220

<210> SEQ ID NO 16
<211> LENGTH: 18
<212> TYPE: DNA
<213> ORGANISM: artificial
<220> FEATURE:
<223> OTHER INFORMATION: Primer

<400> SEQUENCE: 16
ctgtgctgtc tgcgctgc                                             18

<210> SEQ ID NO 17
<211> LENGTH: 26
<212> TYPE: DNA
<213> ORGANISM: artificial
<220> FEATURE:
<223> OTHER INFORMATION: Primer

<400> SEQUENCE: 17
atcgtgcaaa acaactctgt attcag                                    26

<210> SEQ ID NO 18

```
<211> LENGTH: 24
<212> TYPE: DNA
<213> ORGANISM: artificial
<220> FEATURE:
<223> OTHER INFORMATION: Primer

<400> SEQUENCE: 18
ccagaagatg ctccattgga agat                                          24

<210> SEQ ID NO 19
<211> LENGTH: 27
<212> TYPE: DNA
<213> ORGANISM: artificial
<220> FEATURE:
<223> OTHER INFORMATION: Primer

<400> SEQUENCE: 19
ttaagacata gtagtagcag tagccaa                                       27

<210> SEQ ID NO 20
<211> LENGTH: 27
<212> TYPE: DNA
<213> ORGANISM: artificial
<220> FEATURE:
<223> OTHER INFORMATION: Primer

<400> SEQUENCE: 20
atgatgtctg ttgctactgt tgaacca                                       27

<210> SEQ ID NO 21
<211> LENGTH: 28
<212> TYPE: DNA
<213> ORGANISM: artificial
<220> FEATURE:
<223> OTHER INFORMATION: Primer

<400> SEQUENCE: 21
ttaacaaatt ggcaatggag aaccgttc                                      28

<210> SEQ ID NO 22
<211> LENGTH: 26
<212> TYPE: DNA
<213> ORGANISM: artificial
<220> FEATURE:
<223> OTHER INFORMATION: Primer

<400> SEQUENCE: 22
atggaaactg ttactaagaa cggtta                                        26

<210> SEQ ID NO 23
<211> LENGTH: 25
<212> TYPE: DNA
<213> ORGANISM: artificial
<220> FEATURE:
<223> OTHER INFORMATION: Primer

<400> SEQUENCE: 23
ttagaaagat cttggcttag caaca                                         25

<210> SEQ ID NO 24
<211> LENGTH: 28
<212> TYPE: DNA
<213> ORGANISM: artificial
<220> FEATURE:
<223> OTHER INFORMATION: Primer

<400> SEQUENCE: 24
```

```
atggatttgt tgttgttgga aaagactt                                      28

<210> SEQ ID NO 25
<211> LENGTH: 27
<212> TYPE: DNA
<213> ORGANISM: artificial
<220> FEATURE:
<223> OTHER INFORMATION: Primer

<400> SEQUENCE: 25
atgtctaact acgaaggtag atggact                                       27

<210> SEQ ID NO 26
<211> LENGTH: 26
<212> TYPE: DNA
<213> ORGANISM: artificial
<220> FEATURE:
<223> OTHER INFORMATION: Primer

<400> SEQUENCE: 26
tcatctcttg taagcttgca aacctg                                        26

<210> SEQ ID NO 27
<211> LENGTH: 33
<212> TYPE: DNA
<213> ORGANISM: artificial
<220> FEATURE:
<223> OTHER INFORMATION: Primer

<400> SEQUENCE: 27
ttattcaatt tcttcgtatg gcaaaccaac gta                                33

<210> SEQ ID NO 28
<211> LENGTH: 28
<212> TYPE: DNA
<213> ORGANISM: artificial
<220> FEATURE:
<223> OTHER INFORMATION: Primer

<400> SEQUENCE: 28
atgaagactc aagttgctat tattggtg                                      28

<210> SEQ ID NO 29
<211> LENGTH: 41
<212> TYPE: DNA
<213> ORGANISM: artificial
<220> FEATURE:
<223> OTHER INFORMATION: Primer

<400> SEQUENCE: 29
ttaaaccttc ttcaagaatt ccataatgta agtgttgaaa g                       41

<210> SEQ ID NO 30
<211> LENGTH: 24
<212> TYPE: DNA
<213> ORGANISM: artificial
<220> FEATURE:
<223> OTHER INFORMATION: Primer

<400> SEQUENCE: 30
atgggttcta ctggtgaaac tcaa                                          24

<210> SEQ ID NO 31
<211> LENGTH: 20
<212> TYPE: DNA
```

```
<213> ORGANISM: artificial
<220> FEATURE:
<223> OTHER INFORMATION: Primer

<400> SEQUENCE: 31
gcgcatgtgt ccgatctttg                                               20

<210> SEQ ID NO 32
<211> LENGTH: 24
<212> TYPE: DNA
<213> ORGANISM: artificial
<220> FEATURE:
<223> OTHER INFORMATION: Primer

<400> SEQUENCE: 32
atggcttacg ttaacggtac tact                                          24

<210> SEQ ID NO 33
<211> LENGTH: 28
<212> TYPE: DNA
<213> ORGANISM: artificial
<220> FEATURE:
<223> OTHER INFORMATION: Primer

<400> SEQUENCE: 33
ttacaaagat cttggcttac aaacaata                                      28

<210> SEQ ID NO 34
<211> LENGTH: 27
<212> TYPE: DNA
<213> ORGANISM: artificial
<220> FEATURE:
<223> OTHER INFORMATION: Primer

<400> SEQUENCE: 34
ttatctcttg taagcttgca aacctgg                                       27

<210> SEQ ID NO 35
<211> LENGTH: 30
<212> TYPE: DNA
<213> ORGANISM: artificial
<220> FEATURE:
<223> OTHER INFORMATION: Primer

<400> SEQUENCE: 35
ttaagcaatt tcttcgtatg gcaaaccaac                                    30

<210> SEQ ID NO 36
<211> LENGTH: 28
<212> TYPE: DNA
<213> ORGANISM: artificial
<220> FEATURE:
<223> OTHER INFORMATION: Primer

<400> SEQUENCE: 36
atgaagactc aagttgctat tattggtg                                      28

<210> SEQ ID NO 37
<211> LENGTH: 30
<212> TYPE: DNA
<213> ORGANISM: artificial
<220> FEATURE:
<223> OTHER INFORMATION: Primer

<400> SEQUENCE: 37
tcacttgttg aattccataa cccaaacgtt                                    30
```

<210> SEQ ID NO 38
<211> LENGTH: 22
<212> TYPE: DNA
<213> ORGANISM: artificial
<220> FEATURE:
<223> OTHER INFORMATION: Primer

<400> SEQUENCE: 38
cgaaagaggt gaatggttga ag                                    22

<210> SEQ ID NO 39
<211> LENGTH: 27
<212> TYPE: DNA
<213> ORGANISM: artificial
<220> FEATURE:
<223> OTHER INFORMATION: Primer

<400> SEQUENCE: 39
ttaaccttcg ttagatggga aagaagt                               27

<210> SEQ ID NO 40
<211> LENGTH: 28
<212> TYPE: DNA
<213> ORGANISM: artificial
<220> FEATURE:
<223> OTHER INFORMATION: Primer

<400> SEQUENCE: 40
atggatagag gtaagactat gattgaaa                              28

<210> SEQ ID NO 41
<211> LENGTH: 24
<212> TYPE: DNA
<213> ORGANISM: artificial
<220> FEATURE:
<223> OTHER INFORMATION: Primer

<400> SEQUENCE: 41
ttaacaaatt ggcaatggag cacc                                  24

<210> SEQ ID NO 42
<211> LENGTH: 24
<212> TYPE: DNA
<213> ORGANISM: artificial
<220> FEATURE:
<223> OTHER INFORMATION: Primer

<400> SEQUENCE: 42
atggcttacg ttaacggtac tact                                  24

<210> SEQ ID NO 43
<211> LENGTH: 28
<212> TYPE: DNA
<213> ORGANISM: artificial
<220> FEATURE:
<223> OTHER INFORMATION: Primer

<400> SEQUENCE: 43
ttacaaagat cttggcttac aaacaata                              28

<210> SEQ ID NO 44
<211> LENGTH: 25
<212> TYPE: DNA
<213> ORGANISM: artificial
<220> FEATURE:

<223> OTHER INFORMATION: Primer

<400> SEQUENCE: 44
atggatttcg ttttgttgga aaagg                                        25

<210> SEQ ID NO 45
<211> LENGTH: 30
<212> TYPE: DNA
<213> ORGANISM: artificial
<220> FEATURE:
<223> OTHER INFORMATION: Primer

<400> SEQUENCE: 45
tcatctcttt ctaataatgt taacatcatc                                   30

<210> SEQ ID NO 46
<211> LENGTH: 24
<212> TYPE: DNA
<213> ORGANISM: artificial
<220> FEATURE:
<223> OTHER INFORMATION: Primer

<400> SEQUENCE: 46
atgactatta cttctccagc tcca                                         24

<210> SEQ ID NO 47
<211> LENGTH: 26
<212> TYPE: DNA
<213> ORGANISM: artificial
<220> FEATURE:
<223> OTHER INFORMATION: Primer

<400> SEQUENCE: 47
tcacttgttg aattccataa cccaaa                                       26

<210> SEQ ID NO 48
<211> LENGTH: 560
<212> TYPE: PRT
<213> ORGANISM: Penicillium simplicissimum

<400> SEQUENCE: 48

Met Ser Lys Thr Gln Glu Phe Arg Pro Leu Thr Leu Pro Pro Lys Leu
1               5                   10                  15

Ser Leu Ser Asp Phe Asn Glu Phe Ile Gln Asp Ile Ile Arg Ile Val
            20                  25                  30

Gly Ser Glu Asn Val Glu Val Ile Ser Ser Lys Asp Gln Ile Val Asp
        35                  40                  45

Gly Ser Tyr Met Lys Pro Thr His Thr His Asp Pro His His Val Met
    50                  55                  60

Asp Gln Asp Tyr Phe Leu Ala Ser Ala Ile Val Ala Pro Arg Asn Val
65                  70                  75                  80

Ala Asp Val Gln Ser Ile Val Gly Leu Ala Asn Lys Phe Ser Phe Pro
                85                  90                  95

Leu Trp Pro Ile Ser Ile Gly Arg Asn Ser Gly Tyr Gly Gly Ala Ala
            100                 105                 110

Pro Arg Val Ser Gly Ser Val Val Leu Asp Met Gly Lys Asn Met Asn
        115                 120                 125

Arg Val Leu Glu Val Asn Val Glu Gly Ala Tyr Cys Val Val Glu Pro
    130                 135                 140

Gly Val Thr Tyr His Asp Leu His Asn Tyr Leu Glu Ala Asn Asn Leu
145                 150                 155                 160

-continued

Arg Asp Lys Leu Trp Leu Asp Val Pro Asp Leu Gly Gly Ser Val
            165                 170                 175

Leu Gly Asn Ala Val Glu Arg Gly Val Gly Tyr Thr Pro Tyr Gly Asp
            180                 185                 190

His Trp Met Met His Ser Gly Met Glu Val Val Leu Ala Asn Gly Glu
            195                 200                 205

Leu Leu Arg Thr Gly Met Gly Ala Leu Pro Asp Pro Lys Arg Pro Glu
            210                 215                 220

Thr Met Gly Leu Lys Pro Glu Asp Gln Pro Trp Ser Lys Ile Ala His
225                 230                 235                 240

Leu Phe Pro Tyr Gly Phe Gly Pro Tyr Ile Asp Gly Leu Phe Ser Gln
            245                 250                 255

Ser Asn Met Gly Ile Val Thr Lys Ile Gly Ile Trp Leu Met Pro Asn
            260                 265                 270

Pro Arg Gly Tyr Gln Ser Tyr Leu Ile Thr Leu Pro Lys Asp Gly Asp
            275                 280                 285

Leu Lys Gln Ala Val Asp Ile Ile Arg Pro Leu Arg Leu Gly Met Ala
            290                 295                 300

Leu Gln Asn Val Pro Thr Ile Arg His Ile Leu Leu Asp Ala Ala Val
305                 310                 315                 320

Leu Gly Asp Lys Arg Ser Tyr Ser Ser Arg Thr Glu Pro Leu Ser Asp
            325                 330                 335

Glu Glu Leu Asp Lys Ile Ala Lys Gln Leu Asn Leu Gly Arg Trp Asn
            340                 345                 350

Phe Tyr Gly Ala Leu Tyr Gly Pro Glu Pro Ile Arg Arg Val Leu Trp
            355                 360                 365

Glu Thr Ile Lys Asp Ala Phe Ser Ala Ile Pro Gly Val Lys Phe Tyr
            370                 375                 380

Phe Pro Glu Asp Thr Pro Glu Asn Ser Val Leu Arg Val Arg Asp Lys
385                 390                 395                 400

Thr Met Gln Gly Ile Pro Thr Tyr Asp Glu Leu Lys Trp Ile Asp Trp
            405                 410                 415

Leu Pro Asn Gly Ala His Leu Phe Phe Ser Pro Ile Ala Lys Val Ser
            420                 425                 430

Gly Glu Asp Ala Met Met Gln Tyr Ala Val Thr Lys Lys Arg Cys Gln
            435                 440                 445

Glu Ala Gly Leu Asp Phe Ile Gly Thr Phe Thr Val Gly Met Arg Glu
            450                 455                 460

Met His His Ile Val Cys Ile Val Phe Asn Lys Lys Asp Leu Ile Gln
465                 470                 475                 480

Lys Arg Lys Val Gln Trp Leu Met Arg Thr Leu Ile Asp Asp Cys Ala
            485                 490                 495

Ala Asn Gly Trp Gly Glu Tyr Arg Thr His Leu Ala Phe Met Asp Gln
            500                 505                 510

Ile Met Glu Thr Tyr Asn Trp Asn Asn Ser Ser Phe Leu Arg Phe Asn
            515                 520                 525

Glu Val Leu Lys Asn Ala Val Asp Pro Asn Gly Ile Ile Ala Pro Gly
            530                 535                 540

Lys Ser Gly Val Trp Pro Ser Gln Tyr Ser His Val Thr Trp Lys Leu
545                 550                 555                 560

RECOMBINANT HOST CELL FOR BIOSYNTHETIC PRODUCTION

FIELD OF THE INVENTION

The invention refers to a cell comprising heterologous polynucleotides encoding a multienzyme complex involved in the metabolic pathway of phenylpropanoids and its use in the biosynthesis of a vanilloid or a hydroxybenzaldehyde precursor thereof.

BACKGROUND

Vanillin is one of the most important aromatic flavor compounds used in foods, beverages, perfumes, and pharmaceuticals. Natural vanillin which is extracted from orchid *Vanilla planifolia* beans is relatively expensive. The production of vanilla bean is a lengthy process that is highly dependent on suitable soil and climatic conditions. Beans appear after 4-5 years of cultivation and the aroma is developed in fruit after a long process called "curing" that takes 6 months. The consumer demand for natural vanillin highly exceeds the amount of vanillin extracted by plant sources. Less than 5% of worldwide vanillin production comes from natural vanilla. Because of the scarcity and expense of natural vanilla extract, there has long been interest in the synthetic preparation of its predominant component. Vanillin (4-hydroxy-3-methoxybenzal-dehyde) is the major organoleptic component of vanilla flavour.

As the demand for vanillin is higher than can be extracted from orchid *Vanilla planifolia* beans, the remainder is produced by alternative means. Chemical synthesis is the most important source of vanillin. Vanillin was first synthesized from eugenol found in oil of clove and afterward synthesized from lignin containing sulfite liquor, a byproduct of wood pulp processing in paper manufacture. While some vanillin is still made from lignin waste, today most synthetic vanillin is synthesized in a two-step process from the petrochemical precursors: guaiacol and glyoxylic acid. Vanillin can be also produced chemically by molecular breakage of curcumine, eugenol or piperrin.

The large difference between the prices of natural and synthetic vanillin, the increasing customer-led demand for "natural" and "healthy" flavors, and the serving of "natural" marketing claims have been leading to a growing interest of the flavor industry to produce natural vanillin from other natural sources by bioconversion[1,2,3,4,5]. The use of microbial cells and their enzymes as biocatalysts in the synthesis of fine chemicals has attracted much attention in the field green chemistry and white biotechnology. The products of such bioconversion are considered natural since the European Community Legislation (incorporates products that are produced from biological sources by living cells or their enzymes under the term "natural products".

Alternative biotechnology-based approaches for the production are based on bioconversion of lignin, phenolic stilbenes, isoeugenol, eugenol, ferulic acid, or aromatic amino acids, and on de novo biosynthesis, applying fungi, bacteria, plant cells, or genetically engineered microorganisms. Although vanillin production via conversion of isoeugenol has been widely reported in various microorganisms, including *Aspergillus niger*[6]; strains of the genera *Klebsiella*, *Enterobacter*, and *Serratia*[7]; *Rhodococcus rhodochrous*[8]; *Bacillus subtilis* B2[9]; *Bacillus fusiformis*[10]; *B. subtilis* HS8[11]; *Pseudomonas nitroreducens*[12]; *Pseudomonas putida*[13]; *Pseudomonas chlororaphis*[14]; *Bacillus pumilus*[15]; and *Nocardia iowensis*[16]. De novo synthesis from glucose using metabolically engineered yeast strains was recently described[17].

*S. cerevisiae* is a valuable cell factory for production of high-value industrial biotechnological products relies. It is well adapted for bio-refinery processes due to its capacity for cell-recycle fermentation and its remarkable tolerance against various stresses, such as low pH, high temperature, and various inhibitors[18]. Additionally, *S. cerevisiae* is an extremely well characterized model organism, facilitating metabolic engineering[19,20] due to the availability of the complete genome sequence and detailed characterization of metabolic pathways[21].

U.S. Pat. No. 6,372,461B1 describes the synthesis of vanillin from a carbon source, by a microbe-catalyzed conversion step requiring five enzymes which are provided by a recombinant microbe, and an enzyme-catalyzed reduction step to reduce vanillic acid by an aryl-aldehyde dehydrogenase.

EP2388333A2 describes a microbial cell capable of production of vanillin, comprising at least three heterologous enzymatic activities, i.e. 3-dehydroshikimate dehydratase, aromatic carboxylic acid reductase and 3 O-methyl transferase activities.

WO2011124693A1 describes methods of generating gene mosaics by homeologous in vivo recombination, whereby metabolic pathways can be constructed, which do not exist in nature.

US2003/070188 A1 describes a biosynthetic pathway of vanillin that comprises the conversion of p-coumaric acid to p-hydroxybenzaldehyde, and vanillin production in cultured *Vanilla planifolia*, or transgenic cells and plants having improved vanillin production.

Hansen et al. (Appl Environ Microbiol. 2009; 75(9): 2765-2774) describe de novo biosynthesis of vanillin in fission yeast (*Schizosaccharomyces pombe*) and baker's yeast (*Saccharomyces cerevisiae*). The engineered pathways start with dehydroshikimic acid used as a substrate.

Di Gioia et al. (J. Biotechnol. 2011; 156: 309-316) describe metabolic engineering of *Pseudomonas fluorescens* for the production of vanillin from ferulic acid.

Brochado et al. (Microbial Cell Factories 2010; 9: 84) describe improved vanillin production in baker's yeast through in silico design.

Priefert et al. (Appl. Microbiol. Biotechnol. 2001; 56: 296-314) describe the biotechnological production of vanillin and the different biosynthesis routes based on bioconversion of lignin, phenolic stilbenes, isoeugenol, eugenol, ferulic acid, or aromatic amino acids.

Kaur et al. (Appl. Biochem. Microbiol. 2013; 169: 1353-1372) provide a review on biotechnological and molecular approaches for vanillin production.

SUMMARY OF THE INVENTION

It is the objective of the present invention to provide for an enhanced or new capacity for vanillin formation by biosynthesis in a host cell introducing an enzyme or pathway into a host cell.

The object is solved by the subject of the present invention.

According to the invention, there is provided a cell comprising heterologous polynucleotides encoding a multienzyme complex involved in the metabolic pathway of phenylpropanoids and biosynthesis of a vanilloid or a hydroxybenzaldehyde precursor thereof, which multienzyme complex comprises enzymes for the biosynthesis of coumaric acid and a crotonase. Herein coumaric acid is particularly understood as p-coumaric acid.

In particular, the invention provides for a cell comprising heterologous polynucleotides encoding a multienzyme complex involved in the metabolic pathway of phenylpropanoids and biosynthesis of a vanilloid or a hydroxybenzaldehyde precursor thereof, which multienzyme complex comprises enzymes for the biosynthesis of coumaric acid including any of phenylalanine ammonia lyase (PAL), tyrosine ammonia lyase (TAL), or phenylalanine/tyrosine ammonia lyase (PAL/TAL), and optionally one or more further enzymes to convert an aromatic amino acid into coumaric acid, wherein the multienzyme complex further comprises enzymes to convert coumaric acid into vanillin or a hydroxybenzaldehyde precursor thereof, including a crotonase.

The vanilloid or the hydroxyaldehyde precursor may be commercially used as such, i.e. as end-product, or as an intermediate, e.g. to further produce derivatives or end-products using the intermediate as precursor.

According to a specific aspect, the multienzyme complex comprises at least all enzymes as necessary for the biosynthesis of vanillin using coumaric acid as a precursor, or all enzymes as necessary for the biosynthesis of vanillin, or intermediates or metabolites of the vanillin biosynthesis pathway from a carbon source, e.g. those which are necessary for the conversion into vanillin, such as those described herein.

According to further specific aspect, the multienzyme complex comprises at least all enzymes for the biosynthesis of coumaric acid using an aromatic amino acid as a precursor, at least those which are necessary for the conversion into coumaric acid, such as those described herein.

Specifically, the multienzyme complex comprises phenylalanine ammonia lyase (PAL), cinnamic acid hydroxylase (C4H), cytochrome P450 reductase (CPR), a CoA ligase, a crotonase, a 3-monooxygenase and a methyltransferase.

According to a further a specific aspect, the multienzyme complex comprises tyrosine ammonia lyase (TAL), a CoA ligase, a crotonase, a 3-monooxygenase and a methyltransferase.

According to another specific aspect, the multienzyme complex comprises phenylalanine/tyrosine ammonia lyase (PAL/TAL), cinnamic acid hydroxylase (C4H), cytochrome P450 reductase (CPR), a CoA ligase, a crotonase, a 3-monooxygenase and a methyltransferase.

According to a specific embodiment, the multienzyme complex comprises a CoA ligase, preferably 4-coumarate-CoA ligase (4CL).

According to another specific embodiment, the multienzyme complex comprises a 3-monooxygenase, preferably phenolhydroxylase (PheA) and flavinreductase (FLARED), or hydroxybenzoic acid hydroxylase (HBH).

According to another specific embodiment, the multienzyme complex comprises a methyltransferase, preferably an O-methyltransferase, preferably a 3-O-methyltransferase or a 4-O-methyltransferase, preferably caffeic acid O-methyltransferase (COMT).

According to another specific embodiment, the crotonase is enoyl-CoA hydratase (ECH).

According to a specific aspect, the crotonase is an ECH responsible for the chain reduction reaction on p-coumaroylCoA and/or feruloylCoA.

According to a specific aspect, the crotonase is an ECH converting p-coumaroylCoA to 4-hydroxybenzaldehyde.

According to a further specific aspect, the crotonase is an ECH converting feruloylCoA to vanillin.

According to a specific aspect, the cell comprises further
a) a heterologous polynucleotide encoding a carboxyreductase (CAR), optionally together with a polynucleotide encoding a phosphopantetheinyl transferase (PPTase); and/or
b) a heterologous polynucleotide encoding an alcohol oxidase, preferably vanillyl alcohol oxidase (VAO).

According to a specific embodiment, the polynucleotides encode a series of enzymes expressed from a single polycistronic operon, or encode a series of enzymes expressed from separate promoters.

Preferably, the polynucleotides are stably integrated into the cell genome.

The cell may be a eukaryotic or prokaryotic cell, preferably selected from the group consisting of yeast, mammalian, insect, plant and bacterial cells.

In particular, the cell is a DNA repair deficient cell, including any cell deficient in mismatch repair (MMR) or any other deficiency in DNA repair, or a production cell comprising a cluster of polynucleotides assembled in a DNA repair deficient cell.

Specifically, the polynucleotides originate from at least two different species.

According to a specific aspect, at least one of the enzymes is a chimeric enzyme.

According to the invention, there is particularly provided a cell comprising a multienzyme complex comprising heterologous polynucleotides encoding at least five enzymes, preferably at least six enzymes, preferably at least seven enzymes involved in the metabolic pathway of phenylpropanoids and biosynthesis of a vanilloid or a hydroxybenzaldehyde precursor thereof, wherein at least one of the enzymes is a chimeric enzyme.

In a preferred embodiment the chimeric enzyme is preferably
a) encoded by a nucleotide sequence that is composed of fragments of different polynucleotides, which fragments are assembled to a chimeric nucleotide sequence; and/or
b) encoded by a nucleotide sequence that is obtained by insertion, deletion and/or substitution of one or more nucleotides in a parent polynucleotide.

Specifically, the polynucleotide encoding the chimeric enzyme is composed of fragments of different polynucleotides, preferably with a sequence identity of at least 30%, which fragments are assembled to a chimeric nucleotide sequence. In addition, the fragments may be optionally mutagenized to include mutated sequences derived from one or more polynucleotides, e.g. mutated by insertion, deletion and/or substitution of one or more nucleotides.

Alternatively, the polynucleotide encoding the chimeric enzyme is derived from only one parent polynucleotide, and a gene mosaic obtained by e.g. mutagenesis, or by insertion, deletion and/or substitution of one or more nucleotides.

According to the invention, there is further provided a method of engineering a cell of the present invention, by introducing heterologous polynucleotides encoding a multienzyme complex involved in the metabolic pathway of phenylpropanoids and biosynthesis of a vanilloid or a hydroxybenzaldehyde precursor thereof, into the cell genome, comprising
a) providing the polynucleotides encoding the individual enzymes optionally wherein at least one of the polynucleotides is composed of fragments of different polynucleotides, which fragments are assembled to a chimeric nucleotide sequence;
b) assembling the polynucleotides into a cluster and integrating said cluster into the cell genome, preferably by in vivo recombination; and c) optionally engineering a production cell, wherein said cluster is stably integrated in the production cell genome.

Specifically, at least two different polynucleotides encoding an individual enzyme are provided as full-length polynucleotides or fragments thereof, preferably with a sequence identity of at least 30%, and the polynucleotides are assembled and recombined by homeologous in vivo recombination, thereby generating a chimeric nucleotide sequence with at least one cross-over, preferably a gene mosaic.

According to a specific embodiment, in a single step procedure
- a) the cell is transformed with a mixture of said full-length polynucleotides or fragments; and
- b) the chimeric nucleotide sequence is recombined at an integration site of the cell genome, wherein
- i) the 5'-terminal sequence of said polynucleotide has a flanking target sequence that is anchoring to the 3'-end of said integration site, and
- ii) the 3'-terminal sequence of said polynucleotide has a flanking target sequence that is anchoring to the 5'-end of said integration site, and
- c) clones comprising a gene mosaic are selected.

Specifically, there is provided a method wherein at least one of the polynucleotides is composed of fragments of different polynucleotides, which fragments are assembled to a chimeric nucleotide sequence in a single step procedure, wherein
- a) the cell is transformed with said polynucleotides; and
- b) the chimeric nucleotide sequence is recombined at an integration site of the cell genome, wherein
- i) the 5'-terminal sequence of said polynucleotide has a flanking target sequence that is anchoring to the 3'-end of said integration site; and
- ii) the 3'-terminal sequence of said polynucleotide has a flanking target sequence that is anchoring to the 5'-end of said integration site;

and
- c) clones comprising a gene mosaic are selected.

Specifically, polynucleotides encoding a series of at least two enzymes are provided as full-length polynucleotides or fragments of different origin, wherein the 5'-terminal sequence is of the polynucleotide encoding the first enzyme in the series; and the 3'-terminal sequence is of the polynucleotide encoding the last enzyme in the series.

Specifically, the polynucleotides encode a series of enzymes and at least one of the full-length polynucleotides or fragments is a recombined molecule comprising
- a) a 5'-part, which comprises a nucleotide sequence of the first enzyme in the series;
- b) a 3'-part, which comprises a nucleotide sequence of the second enzyme in the series; and
- c) a terminator sequence and a promoter sequence between the 5'-part and the 3'-part.

Specifically, at least two recombined molecules are provided, wherein the 3'-part of the first recombined molecule has a sequence homology of at least 30% with the 5'-part of the second recombined molecule.

According to the invention there is further provided a recombined molecule comprising
- a) a 5'-part, which comprises a nucleotide sequence of a first enzyme in a series of enzymes of a multienzyme complex;
- b) a 3'-part, which comprises a nucleotide sequence of a second enzyme in the series; and
- c) a terminator sequence and a promoter sequence between the 5'-part and the 3'-part.

The first and second enzymes may be in the order of consecutive enzymatic reactions, or not, e.g. in a different order.

According to a specific aspect, the method further comprises producing a repertoire of cells, which differ from each other in the gene mosaic encoding a chimeric enzyme.

According to the invention, there is further provided a library of cells comprising a repertoire obtainable by a method of the invention, preferably a library comprising at least different 100 clones, preferably at least 200, 300, 400, 500, 1.000, 2.000, 3.000, 4.000, 5.000, or at least 10.000 clones.

According to the invention, there is further provided a method of the invention, which further comprises producing a repertoire of aromatic compounds comprising phenylpropanoids, hydroxybenzaldehydes, vanilloids and/or intermediates of vanillin biosynthesis.

According to the invention, there is further provided a method of producing an aromatic compound library comprising phenylpropanoids, hydroxybenzaldehydes, vanilloids and/or hydroxyaldehyde precursor thereof and/or intermediates of vanillin biosynthesis, comprising providing a library of the invention, specifically a library of clones and/or a library of aromatic compounds, cultivating said library in the presence of an initial precursor compound or one or more intermediate precursor compounds to produce a variety of aromatic compounds as metabolites.

According to the invention, there is further provided an aromatic compound library comprising a variety of metabolites obtainable by a method of the invention, wherein at least one metabolite is an artificial metabolite or not naturally-occurring metabolite.

According to the invention, there is further provided the use of a cell of the invention, for heterologous biosynthesis of a metabolite product. Specifically the product is a vanilloid or a hydroxybenzaldehyde precursor thereof, preferably wherein said vanilloid is selected from the group consisting of vanillin, vanillic acid, ethyl-vanillin, vanillyl alcohol and vanillin-glycoside; and/or wherein said hydroxybenzaldehyde precursor is selected from the group consisting of protocatechuic aldehyde, protocatechuic acid, protocatechuic alcohol, 4-hydroxyaldehyde, 4-hydroxybenzoic acid, 4-hydroxybenzyl alcohol and caffeic acid.

According to the invention, there is further provided a method of heterologous biosynthesis of a vanilloid or a hydroxybenzaldehyde precursor thereof, by conversion of a precursor compound employing a multienzyme complex involved in the metabolic pathway of phenylpropanoids and biosynthesis of a vanilloid or a hydroxybenzaldehyde precursor thereof, which multienzyme complex comprises enzymes for the biosynthesis of coumaric acid and a crotonase, preferably at least all enzymes for the biosynthesis of vanillin using coumaric acid as a precursor, comprising providing a cell of the invention;

cultivating said cell in a cell culture in the presence of the precursor compound;

accumulating a product of biosynthesis; and separating said product from the cell culture medium.

Specifically, the multienzyme complex comprises
- a) PAL, C4H, CPR, a CoA ligase, a crotonase, a 3-monooxygenase and a methyltransferase; or b) TAL, a CoA ligase, a crotonase, a 3-monooxygenase and a methyltransferase; or c) PAL/TAL, C4H, CPR, a CoA ligase, a crotonase, a 3-monooxygenase and a methyltransferase.

Specifically, the invention further provides for an isolated multienzyme complex as defined herein, in particular a multienzyme complex comprising a) PAL, C4H, CPR, a CoA ligase, a crotonase, a 3-monooxygenase and a methyltransferase; or b) TAL, a CoA ligase, a crotonase, a 3-monooxygenase and a methyltransferase; or c) PAL/TAL, C4H, CPR, a CoA ligase, a crotonase, a 3-monooxygenase and a methyltransferase.

Specifically, said precursor compound is a natural amino acid, such as phenylalanine, tyrosine or tryptophan, preferably phenylalanine or tyrosine.

Specifically, said precursor compound is monosaccharide, preferably selected from the group consisting of glucose, galactose or arabinose.

Specifically, said product is a vanilloid selected from the group consisting of vanillin, vanillic acid, ethyl-vanillin, vanillyl alcohol and vanillin-glycoside; or a hydroxybenzaldehyde precursor selected from the group consisting of protocatechuic aldehyde, protocatechuic acid, protocatechuic alcohol, 4-hydroxyaldehyde, 4-hydroxybenzoic acid, 4-hydroxybenzyl alcohol, cinnamic acid, coumaric acid, caffeic acid and ferulic acid.

According to a specific aspect, said product is vanillin, or a precursor of vanillin, which is further processed to produce vanillin, preferably by enzymatic methods of biosynthesis (such as by in vivo reactions) or chemical reactions (such as by in vitro reactions), or a derivative of vanillin, preferably vanillic acid, ethyl-vanillin or glycosyl-vanillin.

Specifically, the method of the invention provides for the high-yield production of said product, e.g. with a yield of at least 10 mg/L, preferably at least 20 mg/L, at least 30 mg/L, at least 40 mg/L, at least 50 mg/L, at least 100 mg/L, or at least 200 mg/L of the product, e.g. product concentration obtained in the culture medium.

FIGURES

FIG. 1: The synthesis pathway of vanillin production cell. The figure shows the schematic diagram wherewith phenylalanine is converted into vanillin. Phenylalanine undergoes several reactions: deamination, hydroxylation of 4-position of the phenyl ring, reduction chain reaction and hydroxylation of 3-position of the phenyl ring, and O-methylation of the 3-position of the phenyl ring. The CAR protein catalyzes the reduction of carboxylic acids to their corresponding aldehydes. The role of the PPTase is to transfer the phosphopantetheine from coenzyme A to its acceptor CAR protein. The crotonase designates an enzyme that hydrates the double bond between the second and third carbons on acyl-CoA. The 3-monooxygenase designates an enzyme that incorporates one hydroxyl group into substrates in 3-position of the phenyl ring. The O-methyltransferase designates an enzyme that transfers a methyl group from a donor to a hydroxyl acceptor.

Figure 2:
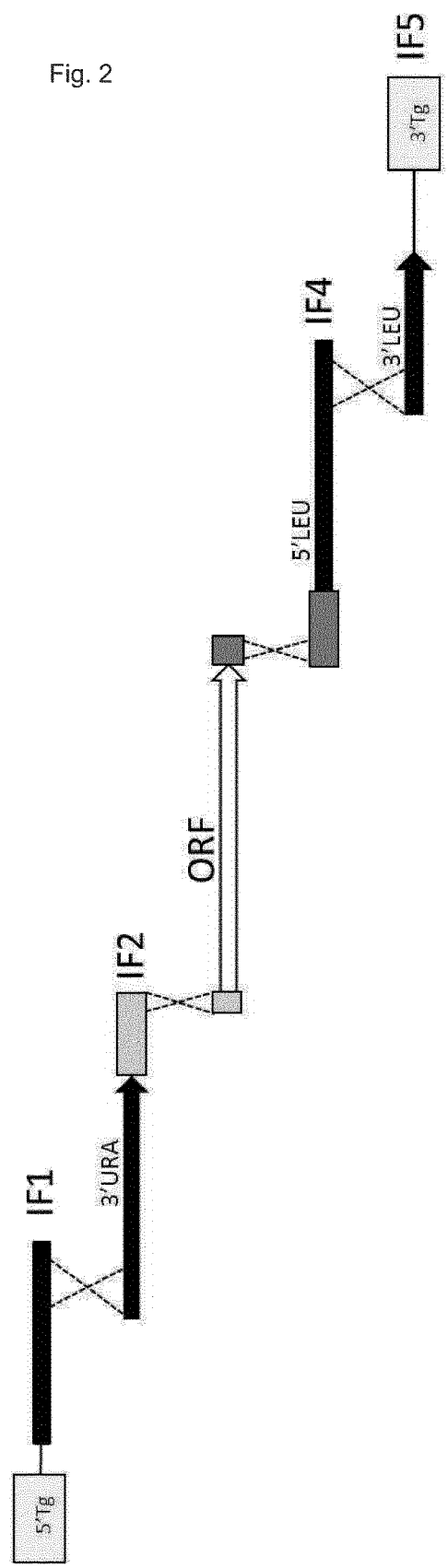

FIG. 2: Strategy for integration of a candidate gene into the yeast genome in order to study its functionality. IF1 contains the 5'-insertion site in the BUD 31 region of the yeast chromosome and 5'-end of URA marker, IF2 contains 3'end URA marker and pGAL promoter. IF4 contains tCYC terminator and 5' end of LEU marker and IF5 contains 3'-end of LEU marker and 3'-insertion site in the BUD 31 region. Synthetized gene was amplified from GeneArt plasmid. The 5'-end of the upstream oligonucleotides used for amplifying the gene of interest contains a sequence of 40 nucleotides homologous with the 3'-end of the pGAL1 promoter. The downstream oligonucleotides contained a 40-nt sequence homologous with the 5'-end of the tCYC terminator. After assembly by homologous recombination in yeast transformant, the double selection permits the recombinant isolation. After recombination, the gene possesses one promoter (pGAL) and one terminator (tCYC) sequence permitting their expression in yeast cells.

Figure 3:
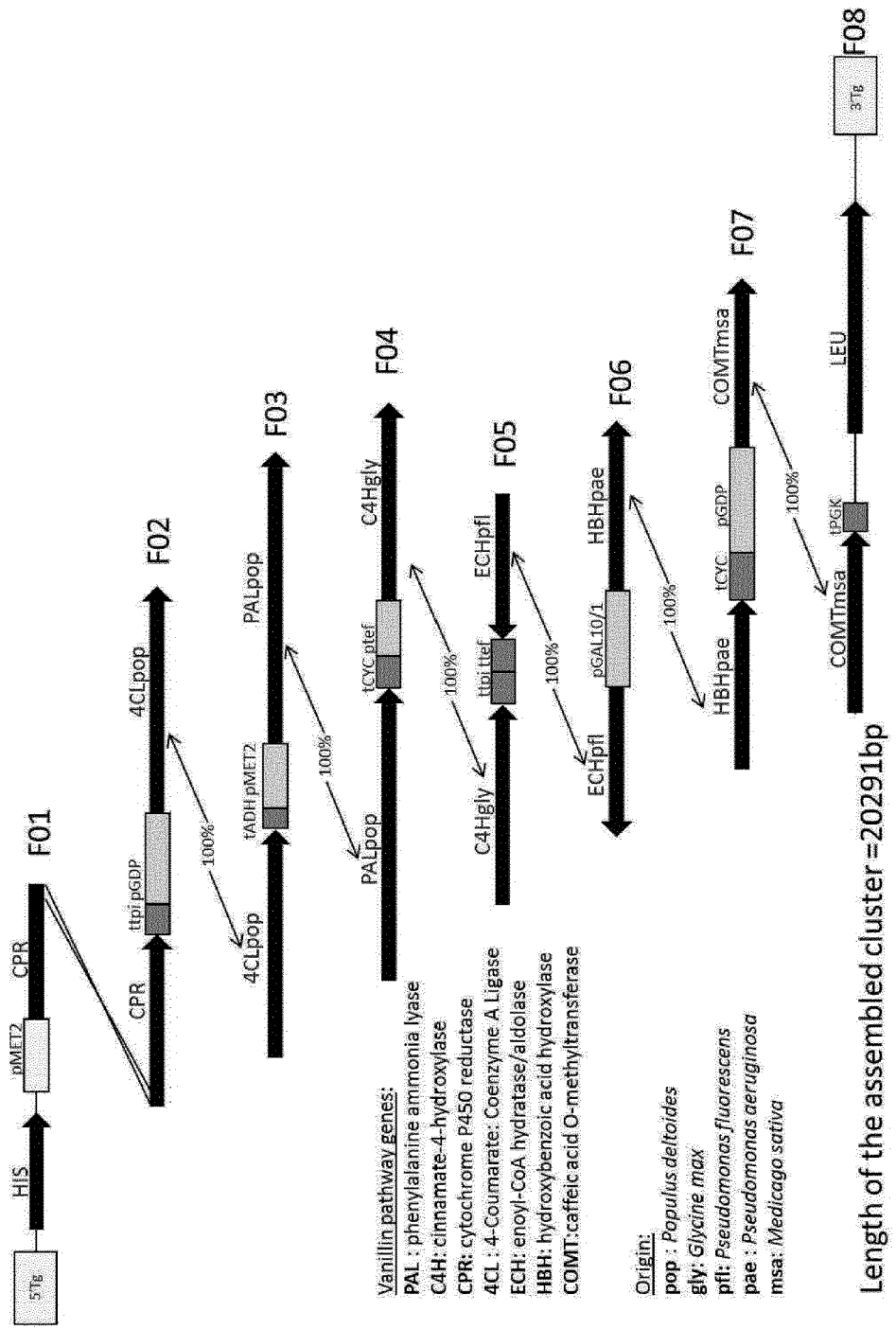

FIG. 3: Assembly of vanillin pathway by fragments containing homologous gene sequences. This figure shows the co-transformation of 8 fragments comprising the 6 genes for vanillin production starting from phenylalanine. URA3 and LEU2 are the flanking markers enabling the double selection of the recombinant pathway. Organism sources of each gene are indicated with three letters following the name of the gene, also shown in three letters. The corresponding organism species are indicated at the left.

Figure 4:
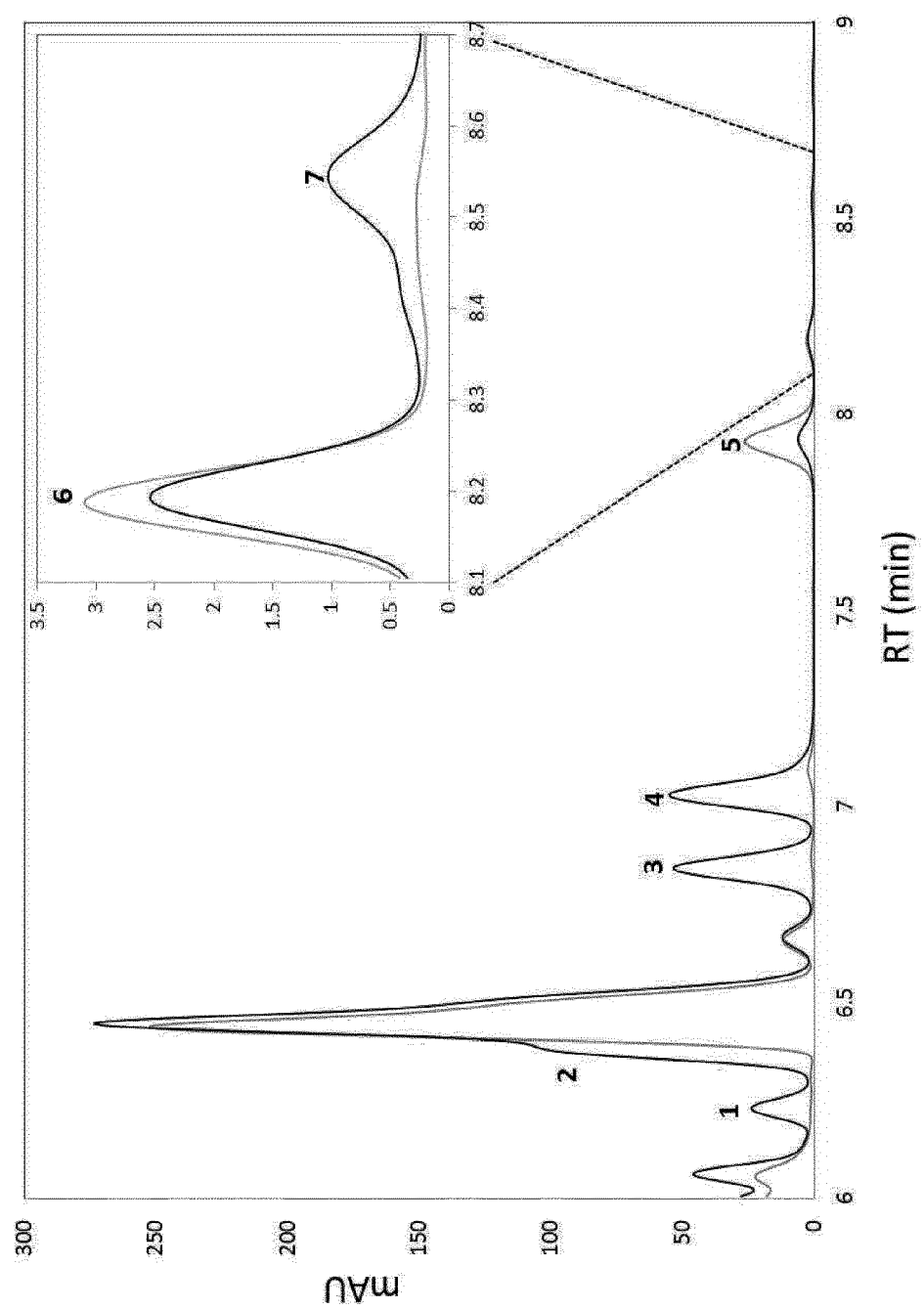

FIG. 4: UV-Visible chromatogram of Y00VAN supernatant (290 nm). Grey line represents negative control strain and black line represents Y00VAN. Peaks were identified by comparing them to our compounds library. 1) 3-4dihydroxybenzoic acid; 2) vanillyl alcohol; 3) 3-4dihydroxybenzaldehyde; 4) vanillic acid; 5) coumaric acid; 6) 4-hydroxybenzaldehyde; 7) vanillin FIG. 5: Accumulation of vanillic acid and 3-4dihydroxybenzoic acid in Y00VAN strain. Culture was performed for 60 hours, then cells were harvested and supernatant was analyzed by HPLC. Concentration of vanillic acid and 3-4dihydroxybenzoic acid were deduced using calibrated standards solutions. The diagram shows accumulation of vanillic acid and 3-4dihydroxybenzoic acid in supernatant depending on the growing conditions.

Figure 6:
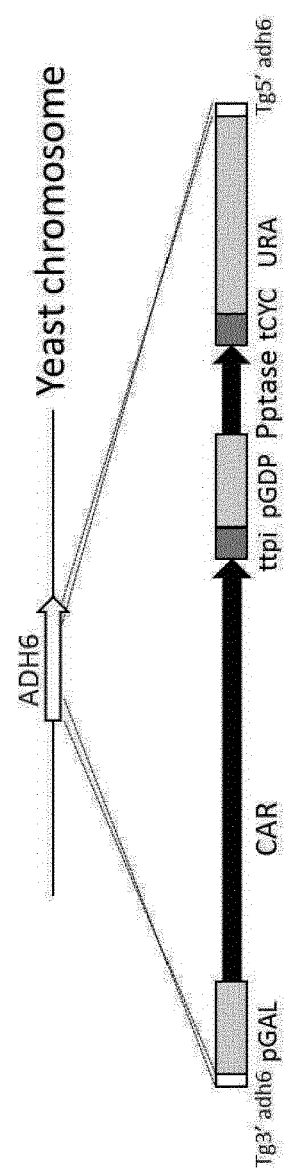

FIG. 6: disruption of ADH6 gene by CAR-PPTase-URA cassette. The figure shows the assembly and integration of the bicistronic construction to the ADH6 locus. The recombinant cell YOCP allows the expression of active CAR protein and endogenous ald6 is inactivated.

Figure 7:
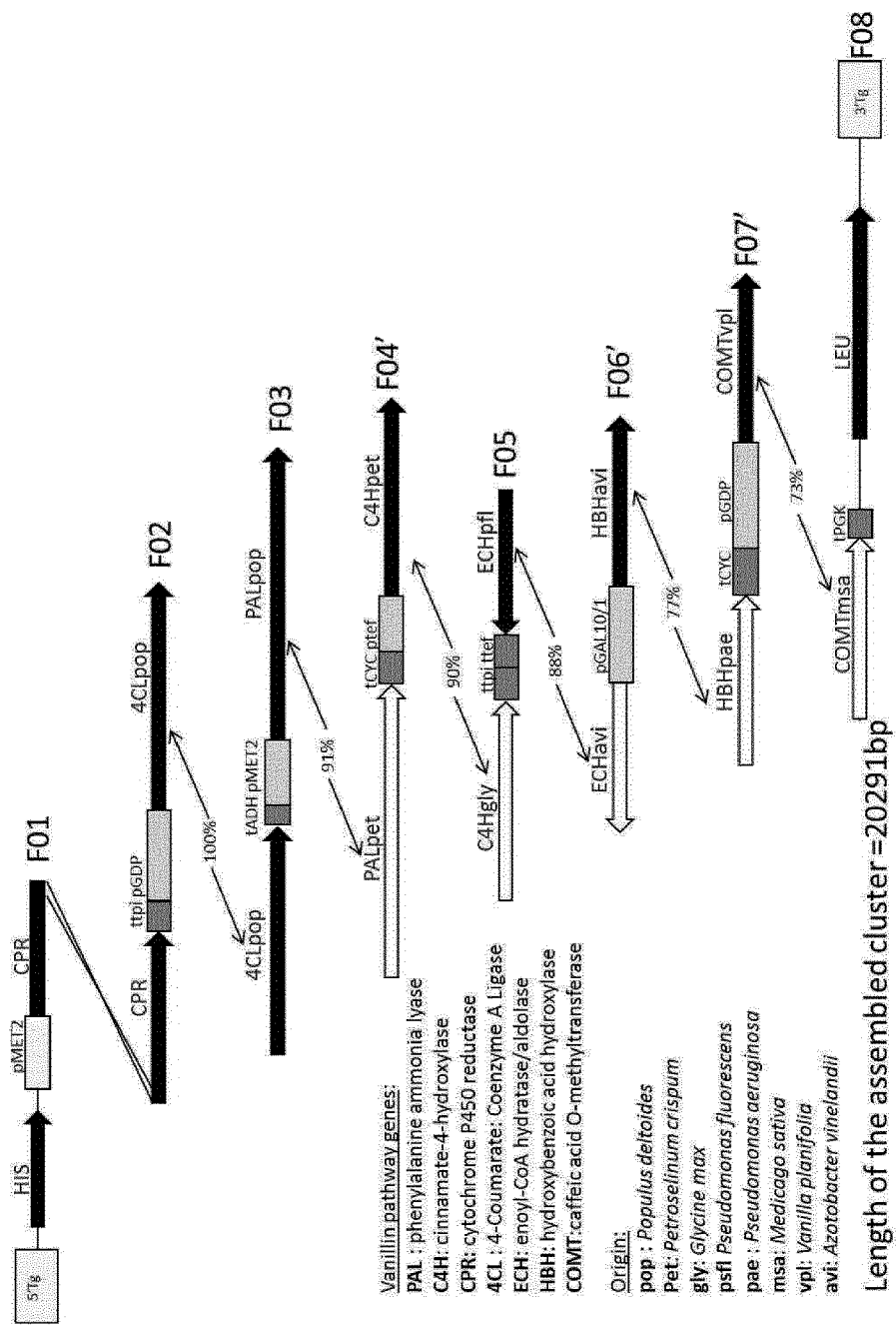

FIG. 7: Assembly of vanillin pathways by fragments containing homeologous gene sequences. This figure shows the co-transformation of 8 fragments comprising the 6 genes for vanillin production starting from phenylalanine. Genes PAL, C4H, ECH, HBH, COMT are related homeologous versions with a given degree of homology (less than 99.5%). HIS3 and LEU2 are the flanking markers enabling the double selection of the recombinant pathway after transformation in a MMR deficient yeast. Organism sources of each gene are indicated with three letters following the name of the gene, also shown in three letters. The corresponding organism species are indicated at the left.

Figure 8:
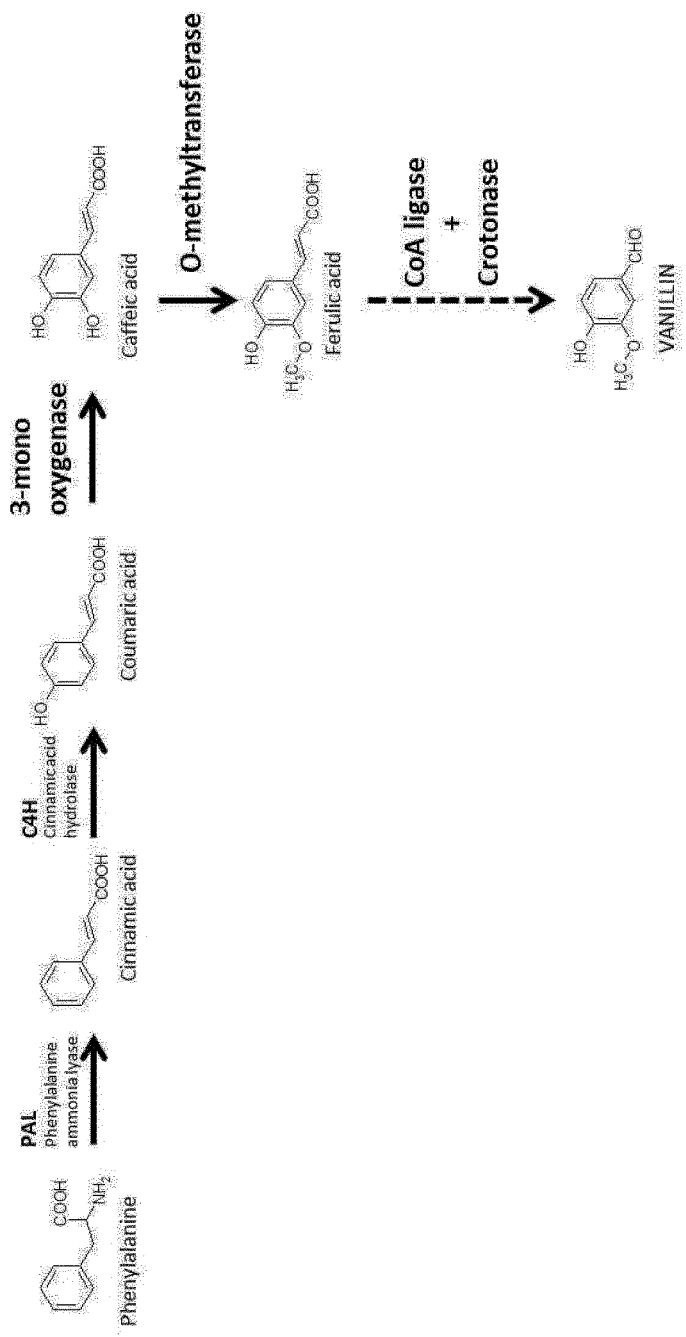

FIG. 8: The synthesis pathway of ferulic acid production cell. The figure shows the schematic diagram wherewith phenylalanine is converted into ferulic acid. Phenylalanine undergoes several reactions: deamination, hydroxylation of 3 and 4 position of the phenyl ring, and O-methylation of the 3 position of the phenyl ring.

Figure 9:
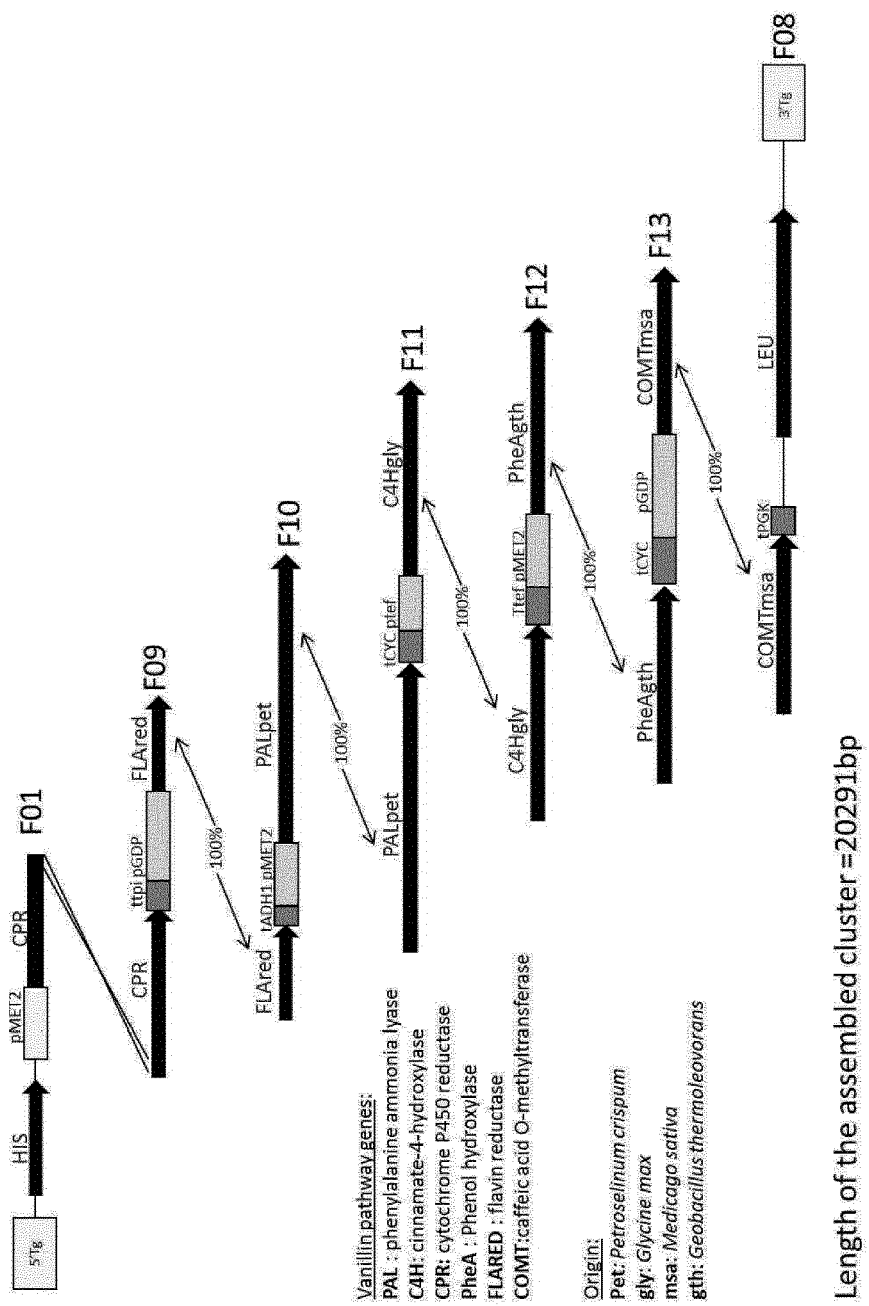

FIG. 9: UV-Visible chromatogram of supernatant of PheA/Flared expressing yeast (290 nm). PheA hydroxylates coumaric acid leading to caffeic acid production. Grey line represents Y00 control strain; black line represents cell expressing PheA/flared and fed with 500 µM coumaric acid.

Figure 10:
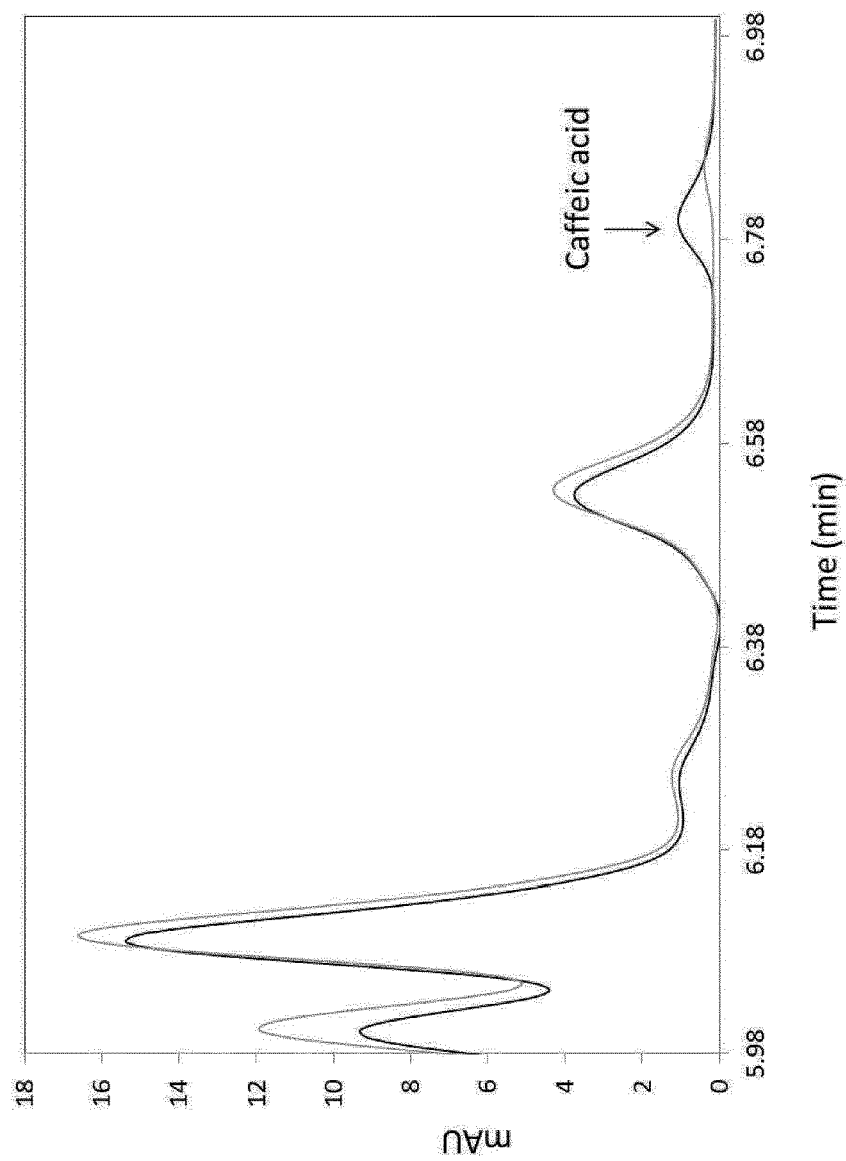

FIG. 10: Assembly of ferulic acid pathway by fragments containing homologous gene sequences. This figure shows the co-transformation of 7 fragments comprising the 5 genes for ferulic acid production starting from phenylalanine.

URA3 and LEU2 are the flanking markers enabling the double selection of the recombinant pathway. Organism sources of each gene are indicated with three letters following the name of the gene, also shown in three letters. The corresponding organism species are indicated at the left.

FIG. 11: Amino acid sequences of exemplary enzymes of a multienzyme complex involved in the metabolic pathway as depicted in FIGS. 3, 6 and 9.

SEQ ID 1: PAL of *Populus deltoids*
SEQ ID 2: PAL of *Petroselinum crispum*
SEQ ID 3: C4H of *Glycine max*
SEQ ID 4: C4H of *Petroselinum crispum*
SEQ ID 5: 4CL of *Populus deltoids*
SEQ ID 6: ECH of *Pseudomonas fluorescens*
SEQ ID 7: ECH of *Azotobacter vinelandii*
SEQ ID 8: HBH of *Pseudomonas aeruginosa*
SEQ ID 9: HBH of *Azotobacter vinelandii*
SEQ ID 10: COMT of *Medicago sativa*
SEQ ID 11: COMT of *Vanilla planifolia*
SEQ ID 12: PheA of *Geobacillus thermoleovorans*
SEQ ID 13: FLARED of *Geobacillus thermoleovorans*
SEQ ID 14: CAR of *Nocardia iowensis*
SEQ ID 15: PPTase of *Nocardia iowensis*
SEQ ID 48: VAO of *Penicillium simplicissimum*, P56216.1 GI:3024813

Figure 12:
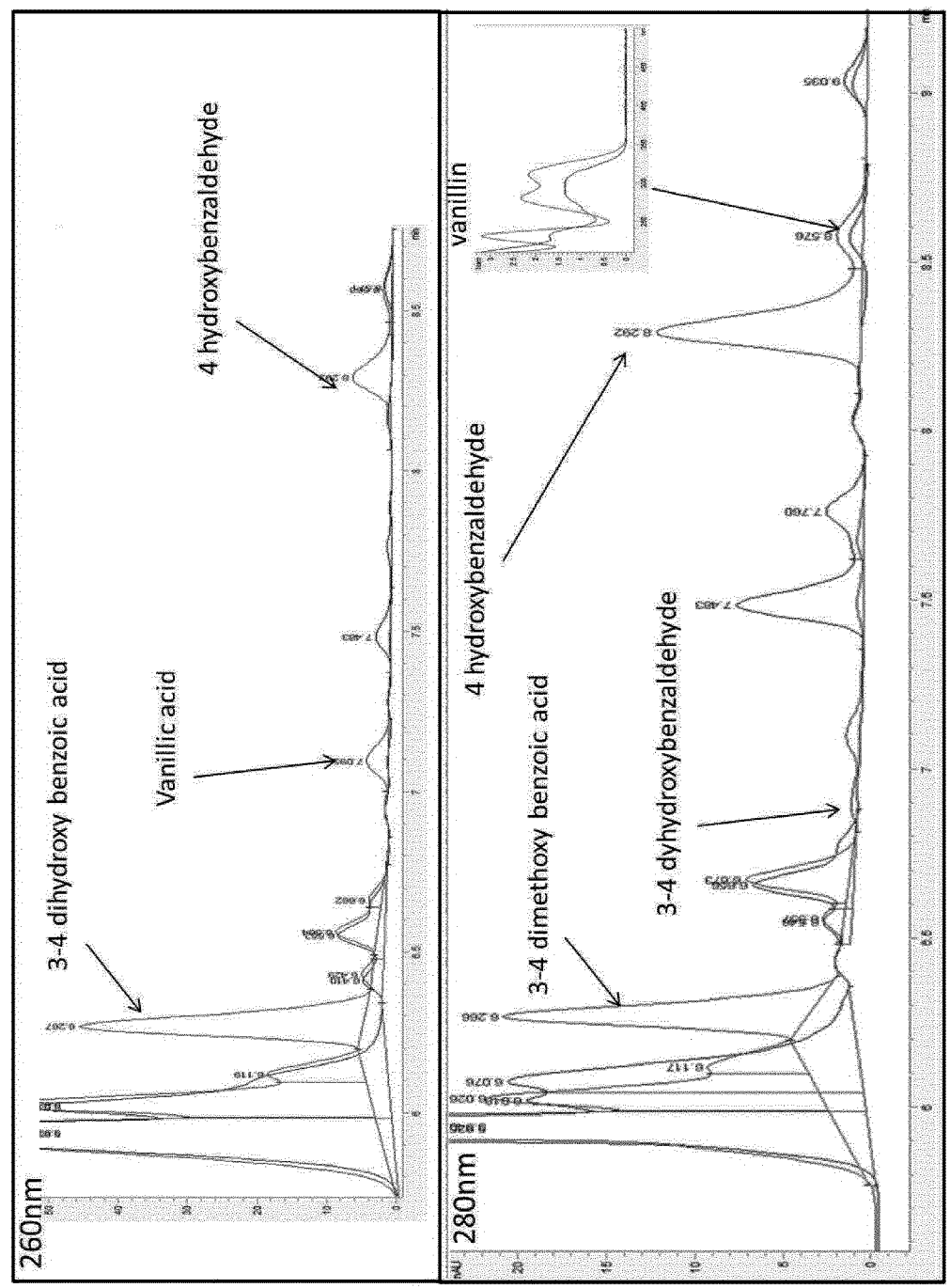

FIG. 12: Accumulation of vanillin, and intermediate metabolites in Y00VANCP strain as to compare to control strain. Culture was performed for 24 hours, then cells were harvested and supernatant was analyzed by HPLC. Concentrations of metabolites were deduced using calibrated standards solutions.

Figure 13:
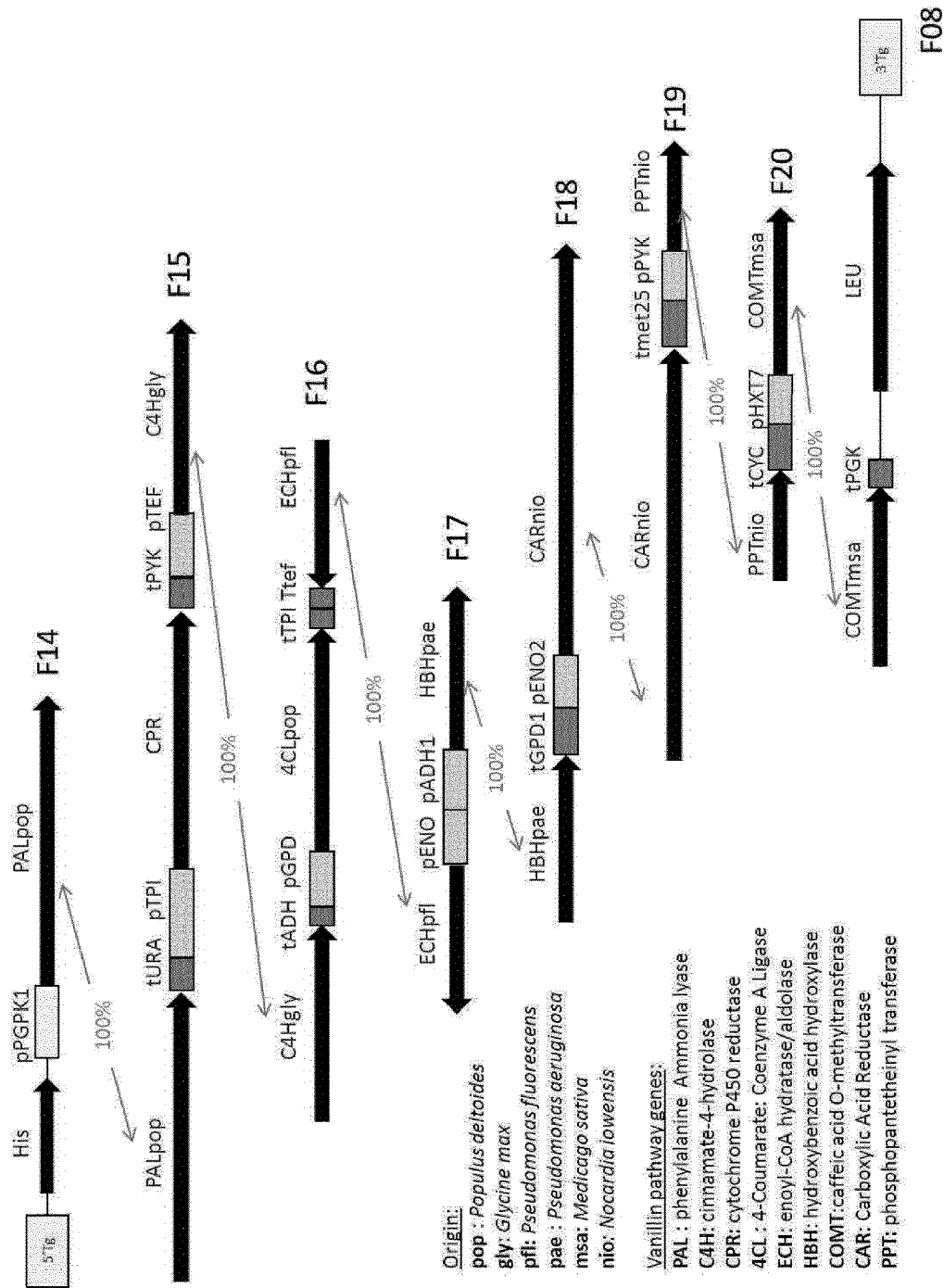

FIG. 13: Assembly of vanillin pathway by fragments containing homologous gene sequences. This figure shows the co-transformation of 8 fragments comprising the 9 genes for vanillin production starting from phenylalanine. HIS3 and LEU2 are the flanking markers enabling the double selection of the recombinant pathway. Organism sources of each gene are indicated with three letters following the name of the gene, also shown in three letters. The corresponding organism species are indicated at the left.

DETAILED DESCRIPTION OF THE INVENTION

The term "assembly" as used herein with respect to polynucleotides, genes or nucleic acids shall refer to the linking or joining of nucleotide sequences, e.g. connecting at least two sequences, such as genes or parts of them, to obtain the gene assembly. In some embodiments, linear synthetic nucleic acid molecules are assembled. Nucleic acid molecules may be provided as linear nucleic acid molecules or may be linearized in vivo or excised from larger nucleic acid molecules.

By an assembly of genes or gene fragments, a composite gene or gene cluster maybe obtained as a single nucleotide sequence. The genes are e.g. stringed together, optionally with an overlap. The assembly as described herein may specifically comprise intragenic and/or intergenic cross over (s) or gene mosaic(s).

An assembled cluster may contain an origin of replication and is capable to replicate in a host cell. In specific embodiments, the assembled cluster is inserted into the host cell genome. Assembly of genetic modules can be achieved by repeated rounds of homologous recombination, or else by in vivo homeologous recombination, such as specifically described herein. In various embodiments, an assembly strategy involves recombination or successive rounds of recombination, and may involve one or more selectable markers. In some embodiments, additional genetic elements can be introduced serially into the host cell by transfection techniques such as electroporation. Yet, in other embodiments, genetic elements can further be introduced into the cluster or host cell genome, e.g. promoter or terminator sequences.

The term "cell" as used herein in particular with reference to engineering and introducing an assembled cluster of genes into a cell, or a production cell is understood to refer to any prokaryotic or eukaryotic cell. Prokaryotic and eukaryotic host cells are both contemplated for use according to the invention, including bacterial host cells like *E. coli* or *Bacillus* sp, yeast host cells, such as *S. cerevisiae*, insect host cells, such as *Spodooptera frugiperda* or human host cells, such as HeLa and Jurkat.

Preferred host cells are haploid cells, such as from *Candida* sp, *Pichia* sp and *Saccharomyces* sp.

The term "cell" shall specifically include a single cell or cells cultivated in a cell culture, such as cell lines.

According to the present invention any wild-type or repair deficient prokaryotic or eukaryotic cells, including those with deficiency in nucleic acid repair, such as DNA or RNA repair may be used to assemble the polynucleotides. In wild-type cells, the suitable integration site is selected, which allows for (homeologous) recombination.

The term "DNA repair deficient cell" as used herein shall refer to a DNA repair deficient prokaryotic or eukaryotic cell, specifically those with a deficiency in nucleic acid repair, e.g. those with mutations or modifications of the mismatch repair (MMR) system, or those with other repair deficient systems, such as completely or temporarily knock-outs of DNA repair genes, e.g. rad1, recQ. In cells not being DNA repair deficient, damaged and mismatched DNA is usually repaired and recombination of homeologous sequences is inhibited. Mutations or modifications of the MMR system or other DNA repair deficient systems would enhance the frequency of recombination in the cells, thereby preferably used to assemble and/or recombine the polynucleotides as described herein, e.g. so to assemble a cluster of polynucleotides and/or to provide for chimeric nucleotide sequences with gene mosaics.

As an example, mismatch repair can be completely or temporarily knocked out, or can be conditional or induced by addition of specific substrates to the cell culture medium, where the cells are cultured during or after targeted recombination is performed. Specifically, MMR deficiency of a cell can be achieved by any strategy that transiently or permanently impairs the mismatch repair, including the mutation of a gene involved in mismatch repair, treatment with UV light, treatment with chemicals, such as 2-aminopurine, inducible expression or repression of a gene involved in the mismatch repair, for example, via regulatable promoters, which would allow for a transient inactivation and activation.

Bacterial mismatch repair systems have been extensively investigated. In other systems, such as yeast, several genes have been identified whose products share homology with the bacterial mismatch repair proteins, e.g. analogs of the MutS protein, i.e. Msh1, Msh2p, Msh3p, Msh4, Msh5, Msh6p, and analogs of the MutL protein, i.e. Mlh1p, Mlh2p, Mlh3p, and Pms1 in *S. cerevisiae*.

Examples for preferred mismatch repair deficient cells are specific yeast cells, such as *S. cerevisiae* strains with defective or (temporarily) inactivated MSH2, e.g. engineered W303, BY, SK1 strains, such as MXY47 (W303 with disrupted MSH2) strain.

Further preferred systems of MMR are a selection of well-known bacterial strains, such as those described in U.S. Pat. No. 5,912,119, like strains defective for the enzymatic MutHLS mismatch repair system, e.g. of the mutS or mutL type, which is defective for the proteins MutS and MutL, which takes part in the recognition of the mismatches. Preferred strains are for example strains of *S. Typhimurium* using F⁻ mutL or recombinant *E. Coli* Hfr/*S. Typhimurium* F⁻ mutL.

Besides, other eukaryotic mismatch repair deficient cells, like HeLa and Jurkat cells are preferably used according to the invention.

The term "production cell" as used herein shall specifically refer to a cell recombinantly engineered to produce a product of a production process or biosynthesis, e.g. a product of a metabolic pathway.

The term "cell line" as used herein refers to an established clone of a particular cell type that has acquired the ability to proliferate over a prolonged period of time. The term "host cell line" refers to a cell line as used for engineering and/or expressing an endogenous or recombinant gene or products of a metabolic pathway to produce polypeptides or cell metabolites mediated by such polypeptides. A "production host cell line" or "production cell line" is commonly understood to be a cell line ready-to-use for cultivation in a bioreactor to obtain the product of a production process or biosynthesis, such as a product of a metabolic pathway.

Once clones are selected that produce the desired products of biosynthesis, the products are typically produced by a production host cell line on the large scale by suitable expression systems and fermentations, e.g. by microbial production in cell culture.

As described herein, a cluster of polynucleotides is typically assembled and eventually recombined to obtain chimeric sequences in a first host cell, e.g. in a DNA repair deficient cell. The cluster may then be transferred to a second host cell which has different properties, such as stability to produce high yields over a prolonged production time. Such second host cell is preferably a production host cell. Therefore, the cluster of polynucleotides may be excised from said first host cell, which served to engineer the cluster, and then integrated into the production host cell genome.

The term "chimeric" as used herein with respect to a polypeptide, such as an enzyme, or a nucleotide sequence, such as a polynucleotide encoding an enzyme, shall refer to those molecules which comprise at least two heterologous parts. In this context, heterologous signifies that the parts are not found in the same position in a single polypeptide or polynucleotide in vivo. Normally, this means that the parts are derived from at least two different polypeptides or polynucleotides, e.g. from different origin, such as analogs derived from different organism or species. The parts may also be obtained by mutagenesis of one source (parent) sequence.

Chimeric polypeptides having different combinations of polypeptide sequences may originate from one or more parent molecules, which may have undergone mutagenesis, thus may comprise mutations, such as insertions, deletions and/or substitutions of one or more amino acids.

Chimeric polynucleotides having different combinations of genes or sequences may originate from one or more parent genes, which may have undergone mutagenesis, thus may comprise mutations, such as insertions, deletions and/or substitutions of one or more nucleotides.

In this context, the term "originating", e.g. with respect to a species of origin, or "different origin" is understood in the following way. A molecule endogenous to a cell of a specific species is herein understood as originating from said species, either in the naturally-occurring form, e.g. as a wild-type molecule and its isomer, or fragments or mutants thereof. A molecule that is characterized by being of a different origin relative to another molecule, is specifically understood to refer to a molecule of different sequence, e.g. obtained or derived from a different species, such as a naturally-occurring molecule, e.g. an analog, or provided as an artificial or recombinant molecule, such as a molecule not occurring as a wild-type molecule in nature.

Exemplary enzymes as described herein are of various prokaryotic or eukaryotic origin, e.g. any of the enzymes with sequences as listed in FIG. 10, or any of the enzymes as described in the Table below:

TABLE 1

Exemplary enzymes as used for assembling a multienzyme complex

| Enzymes | name | organism | Catalyzed reaction |
|---|---|---|---|
| PAL | phenylalanine ammonia lyase | *Petunia* sp and *Populus* sp | Phenylalanine deamination |
| C4H | Cinnamate-4-hydroxylase | *Petunia* sp and *Glycin* sp | Cinnamate 4 hydroxylation |
| 4CL | 4-Coumarate: Coenzyme A Ligase | *Populus* sp | CoA esterification of coumaric acid or ferulic acid |
| ECH | enoyl-CoA hydratase/aldolase activity | *Pseudomonas fluorescens* and *Azotobacter vinelandii* | chain reduction reaction on feruloyl-coA and coumaroyl-coA |
| HBH | hydroxybenzoic acid hydroxylase | *Pseudomonas fluorescens* and *Azotobacter vinelandii* | 4 hydroxybenzaldehyde 3 hydroxylation |
| COMT | caffeic acid O-methyltransferase | *Medicago sativa* and *Vanilla planifolia* | O-methylation of 3-4dihydroxybenzaldehyde and caffeic acid |
| pheA | phenol hydroxylase | *Geobacillus thermoleovorans* | Coumaric acid 3 hydroxylation |
| FlaRed | flavin reductase | *Geobacillus thermoleovorans* | phenol hydroxylase component 2 |

A chimeric enzyme as described herein specifically may comprise analogous sequences of different origin, e.g. from different species, thus, a partial sequence may be homologous to corresponding sequences in enzymes derived from a particular species, while other parts or segments may be homologous to corresponding sequences in another species. Typically the full-length molecules or parts of such molecules are recombined and optionally assembled to obtain a chimeric molecule.

In a specific embodiment, a chimeric enzyme may also be an enzyme in which the positioning, spacing or function of two endogenous partial sequences has been changed, e.g. by manipulation, with respect to the wild-type enzyme. For example, elements of a sequence may be repositioned by adding, shifting or removing nucleotides or amino acids. Alternatively, the amino acid or nucleotide sequence itself may be mutated, e.g. to introduce desired properties. Typically, such properties include the ability to increase the activity of the enzyme.

The term "crotonase" as used herein shall specifically refer to enzymes in the superfamily that have been shown to display dehalogenase, hydratase, and isomerase activities, while others have been implicated in carbon-carbon bond formation and cleavage as well as the hydrolysis of thioesters. These different enzymes share the need to stabilize an enolate anion intermediate derived from an acyl-CoA substrate. This is accomplished by two structurally conserved peptidic NH groups that provide hydrogen bonds to the carbonyl moieties of the acyl-CoA substrates and form an "oxyanion hole". The CoA thioester derivatives bind in a characteristic hooked shape and a conserved tunnel binds the panteteine group of CoA, which links the 3'-phosphate ADP binding site to the site of reaction. Enzymes in the crotonase superfamily include those catalytically performing a chain reduction reaction on feruloylCoA or coumaroylCoA, e.g. enoyl-CoA hydratase (ECH, crotonase; EC 4.2.1.17), which catalyses the hydratation of 2-trans-enoyl-CoA into 3-hydroxyacyl-CoA.

The term "phenylalanine ammonia lyase" (PAL) as used herein shall specifically refer to an enzyme catalyzing the phenylalanine deamination reaction. In enzymology, a phenylalanine ammonia-lyase (EC 4.3.1.24) is an enzyme that catalyzes the chemical conversion of L-phenylalanine to trans-cinnamate and ammonia. The systematic name of this enzyme class is L-phenylalanine ammonia-lyase (trans-cinnamate-forming). Other names commonly used include tyrase, phenylalanine deaminase, tyrosine ammonia-lyase, L-tyrosine ammonia-lyase, phenylalanine ammonium-lyase, PAL, and L-phenylalanine ammonia-lyase. This enzyme participates in five metabolic pathways: tyrosine metabolism, phenylalanine metabolism, nitrogen metabolism, phenylpropanoid biosynthesis, and alkaloid biosynthesis. The term "cinnamic acid hydroxylase" (C4H) as used herein shall specifically refer to an enzyme catalyzing the cinnamate 4 hydroxylation, which is a P450-dependent enzyme. C4H is also called cinnamate-4-hydroxylase. [EC.1.14.13.11]

The term "cytochrome P450 reductase" (CPR), also known as NADPH:ferrihemoprotein oxidoreductase, NADPH:hemoprotein oxidoreductase, NADPH:P450 oxidoreductase, P450 reductase, POR, CPR or CYPOR, as used herein shall specifically refer to the membrane-bound enzyme required for electron transfer to cytochrome P450 in the endoplasmic reticulum of a eukaryotic cell from a FAD- and FMN-containing enzyme NADPH:cytochrome P450 reductase (POR; EC 1.6.2.4).

The term "tyrosine ammonia lyase" (TAL, L-tyrosine ammonia-lyase, or Tyrase) as used herein shall specifically refer to an enzyme catalyzing the tyrosine deamination reaction (EC 4.3.1.23). It is involved in the natural phenols biosynthesis pathway.

The term "phenylalanine/tyrosine ammonia lyase" (PAL/TAL) as used herein shall specifically refer to an enzyme catalyzing the phenylalanine or tyrosine deamination reaction (EC. EC 4.3.1.25). In enzymology, PAL/TAL catalyzes the non-oxidative deamination of L-phenylalanine and L-tyrosine to form trans-cinnamic acid and p-coumaric acid respectively with similar efficiencies.

The term "CoA ligase" as used herein shall specifically refer to an enzyme catalyzing the CoA esterification of coumaric acid or ferulic acid. Specifically the CoA ligase as described herein is the 4-coumarate-CoA ligase (4CL; EC 6.2.1.12) which catalyzes the chemical reaction of 4-coumarate and CoA to obtain 4-coumaroyl-CoA as a product. This enzyme belongs to the family of ligases, specifically those forming carbon-sulfur bonds as acid-thiol ligases. The systematic name of this enzyme class is 4-coumarate:CoA ligase (AMP-forming). Other names in common use include 4-coumaroyl-CoA synthetase, p-coumaroyl CoA ligase, p-coumaryl coenzyme A synthetase, p-coumaryl-CoA synthetase, p-coumaryl-CoA ligase, feruloyl CoA ligase, hydroxycinnamoyl CoA synthetase, 4-coumarate:coenzyme A ligase, caffeolyl coenzyme A synthetase, p-hydroxycinnamoyl coenzyme A synthetase, feruloyl coenzyme A synthetase, sinapoyl coenzyme A synthetase, 4-coumaryl-CoA synthetase, hydroxycinnamate:CoA ligase, p-coumaryl-CoA ligase, p-hydroxycinnamic acid:CoA ligase, and 4CL. This enzyme participates in phenylpropanoid biosynthesis.

The term "3-monooxygenase" as used herein shall specifically refer to an enzyme catalyzing the hydroxylation of 4-hydroxybenzaldehyde, such as by the hydroxybenzoic acid hydrolase (HBH), or the coumaric acid 3-hydroxylation, such as by the phenolhydroxylase (PheA) and the flavinreductase (FLARED).

HBH, also known as 4-hydroxybenzoate 3-monooxygenase (EC 1.14.13.2) is an enzyme that catalyzes the chemical conversion of 4-hydroxybenzoate to produce protocatechuate. This enzyme belongs to the family of oxidoreductases, specifically those acting on paired donors, with $O_2$ as oxidant and incorporation or reduction of oxygen. The oxygen incorporated need not be derived from $O_2$ with NADH or NADPH as one donor, and incorporation of one atom oxygen into the other donor. The systematic name of this enzyme class is 4-hydroxybenzoate, NADPH:oxygen oxidoreductase (3-hydroxylating). Other names in common use include p-hydroxybenzoate hydrolyase, p-hydroxybenzoate hydroxylase, 4-hydroxybenzoate 3-hydroxylase, 4-hydroxybenzoate monooxygenase, 4-hydroxybenzoic hydroxylase, p-hydroxybenzoate-3-hydroxylase, p-hydroxybenzoic acid hydrolase, p-hydroxybenzoic acid hydroxylase, and p-hydroxybenzoic hydroxylase. This enzyme participates in benzoate degradation via hydroxylation and 2,4-dichlorobenzoate degradation. It employs one cofactor, FAD.

PheA also named phenol hydroxylase (EC 1.14.13.7) is a two-component flavin adenine dinucleotide (FAD)-dependent monooxygenase that converts phenolic compounds. This enzyme belongs to the family of oxidoreductases. PheA is able to use FADH2 and O2 for the oxidation of phenol leading to catechol, as the first step of phenol degradation. PheA requires a flavin reductase.

FLARED or flavin reductase component (EC 1.5.1.36) is an enzyme component of the phenol hydroxylase, which catalyzes the reduction of free flavins by NADH. The enzyme has similar affinity to FAD, FMN and riboflavin. The flared component uses NADH to catalyze the reduction of a flavin that diffuses to the PheA component for oxidation of the substrate by molecular oxygen.

The term "methyltransferase" as used herein shall specifically refer to a methylase which is a type of transferase enzyme that transfers a methyl group from a donor to an acceptor. The term shall specifically refer to an O-methyltransferase, preferably a 3-O-methyltransferase or a 4-O-methyltransferase, preferably caffeate O-methyltransferase or caffeic acid O-methyltransferase (COMT) (EC 2.1.1.68), which is an enzyme that catalyzes the chemical conversion of 3,4-dihydroxy-trans-cinnamate (caffeic acid) to 3-methoxy-4-hydroxy-trans-cinnamate (ferulic acid). This enzyme is also capable of converting protocatechuic aldehyde to vanillin. This enzyme belongs to the family of transferases, specifically those transferring one-carbon group methyltransferases. The systematic name of this enzyme class is S-adenosyl-L-methionine:3,4-dihydroxy-trans-cinnamate 3-O-methyltransferase. Other names in common use include caffeate methyltransferase, caffeate 3-O-methyltransferase, and S-adenosyl-L-methionine:caffeic acid-O-methyltransferase. This enzyme participates in phenylpropanoid biosynthesis.

The term "alcohol oxidase" as used herein shall refer to an enzyme that catalyzes the chemical reaction of a primary alcohol to an aldehyde (EC 1.1.3.38). This enzyme belongs to the family of oxidoreductases, specifically those acting on the CH—OH group of donor with oxygen as acceptor. The systematic name of this enzyme class is alcohol:oxygen oxidoreductase. A specifically preferred alcohol oxidase as used herein is a vanillyl alcohol oxidase, e.g. as described in U.S. Pat. No. 5,721,125, that will convert vanillyl alcohol into vanillin.

The term "gene" as used herein shall specifically refer to genes or DNA fragments of a gene, in particular those that are partial genes. A fragment can also contain several open reading frames, either repeats of the same ORF or different ORF's. The term shall specifically refer to coding nucleotide sequences, but shall also include nucleotide sequences which are non-coding, e.g. untranscribed or untranslated sequences, or encoding polypeptides, in whole or in part.

The term shall particularly apply to the polynucleotide(s) as used herein, e.g. as full-length nucleotide sequence or fragments or parts thereof, which encodes a polypeptide with enzymatic activity, e.g. an enzyme of a metabolic pathway, or fragments or parts thereof, respectively.

The genes as used herein, e.g. for assembly, diversification or recombination can be non-coding sequences or sequences encoding polypeptides or protein encoding sequences or parts or fragments thereof having sufficient sequence length for successful recombination events. More specifically, said genes have a minimum length of 3 bp, preferably at least 100 bp, more preferred at least 300 bp.

The term "gene mosaic" according to the invention means the combination of at least two different genes or partial genes with at least one cross-over event, preferably at least two, at least three, at least four, at least five, at least six, at least seven or even more cross-overs within a single polynucleotide encoding the same type of enzyme ("intragenic") or within a single molecule or nucleic acid strand, e.g. a cross-over at the nucleic acid section joining polynucleotides encoding different types of enzymes to obtain an assembly of the polynucleotides ("intergenic"). Specifically such a cross-over provides for the combination or mixing of DNA sequences. A gene mosaic may be created by intragenic mixing of gene(s), an intragenic gene mosaic, and/or gene assembly, e.g. with intergenic cross-over, with or without an overlapping section, or composite genes stringed together, optionally with an overlap, further optionally assembly of genes with both, intragenic and intergenic cross-over(s) or gene mosaic(s).

The gene mosaics specifically described herein are of at least 3, preferably up to 30.000 base pairs, a preferred range would be 300-25.000 bp; particularly preferred are large DNA sequences of at least 500 bp or at least 1.000 bp.

Specifically preferred are gene mosaics that are characterized by at least 3 cross-over events per 700 base pairs, preferably at least 4 cross-overs per 700 base pairs, more preferred at least 5, 6 or 7 cross-overs per 700 base pairs or per 500 base pairs, which include the crossing of single nucleotides, or segments of at least 1, preferably at least 2, 3, 4, 5, 10, 20 up to larger nucleotide sequences.

According to the preferred method of mitotic or somatic in vivo recombination as described herein, not only odd but also an even number of recombination events can be obtained in one single recombined gene. This is a specific advantage over meiotic in vivo recombination.

Complex patterns of recombinant mosaicism can be obtained by the present method, reaching out high numbers of recombined sequence blocks of different length within one single molecule. Moreover, point-like replacement of nucleotides corresponding to one of the strand templates can be obtained as an important source of diversity respecting the frame of the open reading frames. Mosaicism and point-like exchange are not necessarily conservative at the protein level. Indeed, new amino acids with different polar properties can be generated after recombination, giving novel potential and enzymatic protein properties to the recombinant proteins derived by this method.

The term "cross-over" refers to recombination between genes at a site where two DNA strands can exchange genetic information, i.e. at least one nucleotide. The cross-over process leads to offspring mosaic genes having different combinations of genes or sequences originating from one or more parent genes, which may have undergone mutagenesis, thus may comprise mutations, such as insertions, deletions and/or substitutions of one or more nucleotides Alternatively, other repair mechanisms may be provided, which are not based on cross-over, e.g. nucleotide excision repair or non-homologous end joining mechanisms comprising the recognition of incorrect nucleotides, excision and/or replacement after junction of strands.

The term "heterologous polynucleotide," as used herein, refers to a nucleic acid which is either foreign, i.e. "exogenous", such as not found in nature, to a given host microorganism or host cell; or that is naturally found in a given host microorganismor host cell, e.g., is "endogenous", however, in the context of a heterologous nucleic acid. The heterologous nucleotide sequence as found endogenously may also be produced in an unnatural, e.g. greater than expected or greater than naturally found, amount in the cell. The heterologous nucleotide sequence, or a nucleic acid comprising the heterologous nucleotide sequence, possibly differs in sequence from the endogenous nucleotide sequence but encodes the same protein as found endogenously. Specifically, heterologous nucleotide sequences are those not found in the same relationship to a host cell in nature. Any recombinant or artificial nucleotide sequence is understood to be heterologous. An example of a heterologous polynucleotide is a nucleotide sequence encoding an enzyme sequence as described herein, which originates from a species other than the host cell species. A further example is a chimeric polynucleotide. A further example is a nucleotide sequence encoding an enzyme sequence operably linked to a transcriptional control element, e.g., a promoter, to which an endogenous, naturally-occurring enzyme coding sequence is not normally operably linked.

The term "heterologous biosynthesis" as used herein specifically refers to the biosynthesis of products by recombinant host cells, which comprise at least one heterologous element, such as a heterologous polynucleotide, which e.g. enables the biosynthesis of exogenous products, or endogenous products with improved properties or at an increased yield.

The term "biosynthesis" as used herein shall specifically refer to the cellular production of a product, e.g. by in vivo production in host cells in cell culture, specifically microbial host cells, which cellular production may be optionally combined with further biosynthetic production steps (e.g. in a host cell different from the prior one) and/or with reactions of chemical synthesis, e.g. by in vitro reactions.

The term "homologous" or "homeologous" means that one single-stranded nucleic acid nucleic acid sequence may hybridize to a complementary single-stranded nucleic acid sequence. The degree of hybridization may depend on a number of factors including the amount of identity between the sequences and the hybridization conditions such as temperature and salt concentrations as discussed later. Preferably the region of identity is greater than about 1 bp, more preferably the region of identity is greater than 5 bp or greater than 10 bp.

As used herein, two sequences are "homologous" if they share a region of sequence identity, optionally interrupted by one or more mismatched base pairs, such that they are capable of homologous recombinational exchange with each other. In a preferred embodiment, two homologous double-stranded sequences are completely identical. In another embodiment, the extent of homology is interrupted by not more than 1 mismatched base pair every approximately 10 base pairs of identical nucleotides. In a preferred embodiment, the extent of homology is a continuous stretch of at least 30, 40, 50, 60, 70, 80 90 or 100 base pairs of identical nucleotides. In various embodiments, the extent of homology between homologous sequences is a continuous stretch of at least 6, 8, 10, 15, 20, 25, 30, 35, 40, 50, 60, 75 or 100 base pairs of identical nucleotides. In an alternative embodiment, a stretch of identical nucleotides can be interrupted by 1, 2, 3, 4, 5, 6, 7, 8, 9 or 10 non-identical nucleotides per 100 identical nucleotides. In yet other embodiments, the extent of sequence identity between donor sequences and target sequences (i.e., each pair of first and second sequences) is at least 70%, more preferably at least 75%, more preferably at least 80%, more preferably at least 85%, yet most preferably at least 90% or 95% identity. In certain specific embodiments, the extent of sequence identity between donor and target sequences is at least 92%, 94%, 96%, 98% or 99%. Homologous sequences may be interrupted by one or more non-identical residues, provided they are still efficient substrates for homologous recombination.

The term "homology" indicates that two or more nucleotide sequences have (to a certain degree, up to 100%) the same or conserved base pairs at a corresponding position. A homologous sequence, also called complementary, corresponding or matching sequence, as used according to the invention preferably is hybridising with the homologous counterpart sequence, e.g. has at least 30% sequence identity, up to 100% sequence identity. Preferably, a homologous sequence will have at least about 30% nucleotide sequence identity, preferably at least about 40% identity, more preferably at least about 50% identity, more preferably at least about 60% identity, more preferably at least about 70% identity, more preferably at least about 80% identity, more preferably at least about 90% identity, more preferably at least about 95% identity.

Thus, the term as used herein shall also refer to homeologous sequences, which are understood as sequences with less than 100% sequence identity, e.g. less than 99.5% sequence identity, possibly less than 95%, less than 90%, less than 85% or less than 80%, with a respective complementary sequence, with regard to a full-length native DNA sequence or a segment of a DNA sequence as disclosed herein. Preferred ranges with upper and lower limits as cited above are within the range of 30% and 100% or 99.5% corresponding sequence identity. As used herein, the degree of identity always refers to the complementary sequences as well.

According to the invention, it is even possible to assemble gene(s) or gene fragments by in vivo homeologous recombination, with no homology, i.e. with a sequence identity of less than 30% or less than 20% or even less than 10%. Thus, for the purpose of in vivo homologous recombination, the sequences of gene(s) or gene fragments to be assembled and/or recombined optionally have a sequence identity of at least 5%, preferably at least 10% or at least 20%, or at least 30%.

"Percent (%) identity" with respect to the nucleotide sequence of a gene is defined as the percentage of nucleotides in a candidate DNA sequence that is identical with the nucleotides in the DNA sequence, after aligning the sequence and introducing gaps, if necessary, to achieve the maximum percent sequence identity, and not considering any conservative substitutions as part of the sequence identity. Alignment for purposes of determining percent nucleotide sequence identity can be achieved in various ways that are within the skill in the art, for instance, using publicly available computer software. Those skilled in the art can determine appropriate parameters for measuring alignment, including any algorithms needed to achieve maximal alignment over the full length of the sequences being compared.

The term "vanilloid" as used herein shall specifically refer to compounds which possess a vanillyl group, also known as also known as vanilloyl group, with the following formula (1)

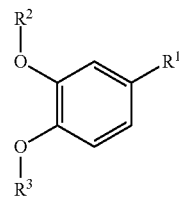

wherein $R^1$ is selected from the group consisting of —COH, —COOH, —CH$_2$OH, —CH$_2$COOH, —C(=O)CH$_3$, —CH(OH)COOH and a glycoside;

$R^2$ is selected from the group consisting of H, —CH$_3$, —CH$_2$CH$_3$ and a glycoside; and $R^3$ is selected from the group consisting of H, —CH$_3$, —CH$_2$CH$_3$ and a glycoside.

The compounds specifically include vanillyl alcohol, vanillin, vanillic acid, ethyl-vanillin, vanillin-glycoside, acetovanillon, vanillylmandelic acid, homovanillic acid, and isomers, such as isovanilloids, and vanilloid derivatives.

The vanilloid compounds as described herein may be specifically produced by biosynthesis, e.g. produced as side-products or intermediates of vanillin biosynthesis, or else produced by another host cell or by chemical reactions, e.g. by in vitro production.

The term "hydroxybenzaldehyde precursor of a vanilloid" as used herein shall specifically refer to a precursor molecule in a chemical reaction or biosynthesis of a vanilloid, e.g. a precursor molecule as used in a metabolic pathway and biosynthesis of a vanilloid, which is a hydroxybenzaldehyde or a respective acid or a respective alcohol, such as a hydroxybenzoic acid, or a respective alcohol, such as an hydroxybenzyl alcohol, e.g. a precursor of biosynthesis through the phenylpropanoid pathway. The term specifically includes protocatechuic aldehyd, 4-hydroxyaldehyde, or a derivative thereof, among them the respective acids, such as protocatechuic acid or 4-hydroxybenzoic acid, or a derivative thereof, among them the respective alcohol, such as protocatechuic alcohol or 4-hydroxybenzyl alcohol. The term shall also include the precursor of vanillin, such as an acid precursor, like cinnamic acid, coumaric acid, caffeic acid or ferulic acid. Therefore, a preferred hydroxybenzaldehyde precursor is selected from the group consisting of protocatechuic aldehyde, protocatechuic acid, protocatechuic alcohol, 4-hydroxyaldehyde, 4-hydroxybenzoic acid, 4-hydroxybenzyl alcohol, cinnamic acid, coumaric acid, caffeic acid and ferulic acid.

The hydroxybenzaldehyde precursor of a vanilloid as described herein may be specifically produced by biosynthesis, e.g. produced as side-products or intermediates of vanillin biosynthesis, or else produced by another metabolic process or by chemical reactions, e.g. by in vitro production.

The term "multienzyme complex" as used herein shall specifically refer to a number or series of enzymes of a metabolic pathway, either in the order of cascadic reactions or else without such order, e.g. by a random sequence. The multienzyme complex produced by a host cell of heterologous biosynthesis typically is encoded by an assembly or at least one cluster of (recombinant) polynucleotides each encoding an enzyme, which assembly or cluster(s) may be e.g. located at one or more different loci on one or more chromosomes, or located on one or more chromosomes in part and additionally located on plasmid(s). The multienzyme complex as described herein does not need to be provided as a complex of proteins, wherein the proteins are linked to each other. The term is rather understood as a multienzyme complex provided as individual enzymes involved in a specific metabolic pathway of a cell.

An exemplary multienzyme complex as described herein comprises enzymes or respective nucleotide sequences of the shikimate pathway, which is a seven step metabolic route used by bacteria, fungi, and plants for the biosynthesis of aromatic amino acids, like phenylalanine, tyrosine and tryptophan.

A further exemplary multienzyme complex as described herein comprises enzymes or respective nucleotide sequences of the cinnamic and p-coumaric acids biosynthesis. Typically, biosynthesis of all phenylpropanoids begins with the amino acids phenylalanine and tyrosine. Phenylalanine ammonia-lyase (PAL, phenylalanine/TAL, tyrosine ammonia-lyase) is an enzyme responsible for the transformation of L-phenylalanine or tyrosine into trans-cinnamic acid or p-coumaric acid, respectively. Trans-cinnamate 4-monooxygenase (cinnamate 4-hydroxylase) is the enzyme responsible for the transformation of trans-cinnamate into 4-hydroxycinnamate (p-coumaric acid). 4-Coumarate-CoA ligase is the enzyme responsible for the transformation of 4-coumarate (p-coumaric acid) into 4-coumaroyl-CoA.

A further exemplary multienzyme complex as described herein comprises enzymes or respective nucleotide sequences of other hydroxycinnamic acids biosynthesis, e.g. comprising any of cinnamyl-alcohol dehydrogenase (CAD), an enzyme responsible for the transformation of cinnamyl alcohol into cinnamaldehyde; sinapine esterase, an enzyme responsible for the transformation of sinapoylcholine into sinapate (sinapic acid) and choline; trans-cinnamate 2-monooxygenase, an enzyme responsible for the transformation of trans-cinnamate (cinnamic acid) into 2-hydroxycinnamate; caffeate O-methyltransferase, an enzyme responsible for the transformation of caffeic acid into ferulic acid; caffeoyl-CoA O-methyltransferase, an enzyme responsible for the transformation of caffeoyl-CoA into feruloyl-CoA; 5-O-(4-coumaroyl)-D-quinate 3'-monooxygenase, an enzyme responsible for the transformation of trans-5-O-(4-coumaroyl)-D-quinate into trans-5-O-caffeoyl-D-quinate; sinapoylglucose-choline O-sinapoyltransferase, an enzyme responsible for the transformation of 1-O-sinapoyl-beta-D-glucose into sinapoylcholine (sinapine); and sinapoylglucose-malate O-sinapoyltransferase, an enzyme responsible for the transformation of 1-O-sinapoyl-beta-D-glucose into sinapoyl-(S)-malate.

Preferred multienzyme complexes comprise a series of enzymes, e.g. a mixture of enzymes. The polynucleotides encoding the enzymes of a multienzyme complex may be assembled and procided as cluster, wherein the nucleic acid encodes the enzymes, e.g. in the order of the enzymatic (catalyzed) reactions or irrespective of the order.

The term "metabolic pathway" refers to a series of two or more enzymatic reactions in which the product of one enzymatic reaction becomes the substrate for the next enzymatic reaction. At each step of a metabolic pathway, intermediate compounds are formed and utilized as substrates for a subsequent step. These compounds may be called "metabolic intermediates." The products of each step are also called "metabolites."

Enzymes of a metabolic pathway as described herein typically play an integral role in primary and/or secondary metabolism. In primary metabolism an enzyme is essential for viability, e.g. directly involved in the normal growth, development, or reproduction of an organism. In secondary metabolism an enzyme serves to produce secondary metabolites, which are understood as organic compounds that are—unlike primary metabolites—not essential for viability in the first instance. Absence of secondary metabolites does not result in immediate death, but rather in long-term impairment of the organism's survivability, fecundity, or aesthetics, or perhaps in no significant change at all. Vanilloids or benzaldehyde precursors thereof are specifically understood as secondary metabolites, which may find use as aroma, medicines, flavorings, fragrance agents or as food ingredient.

The term "metabolic pathway of phenylpropanoids" as described herein specifically refers to a metabolic pathway comprising the enzymatic reactions catalyzed by the enzymes involved in the biosynthesis of phenylpropanoids including the biosynthesis of precursors of aromatic amino acids the biosynthesis of products resulting from subsequent metabolic processing, e.g. the phenylpropanoid pathway The enzymes involved in the metabolic pathway of phenylpropanoids and biosynthesis of a vanilloid or a hydroxybenzaldehyde precursor thereof, particularly encompass a set of enzymes that converts aromatic amino acids into coumaric acid, and further a crotonase. FIGS. 1 and 7 illustrate different embodiments of such pathway. The metabolic pathway may further encompass enzymes that convert precursor carbon sources, like monosaccharides or disaccharides, such as glucose, to aromatic amino acids. The metabolic pathway specifically may include all enzymes necessary for the biosynthesis of a vanilloid such as vanillin, or derivatives of vanillin.

The metabolic pathway as described herein may particularly comprise at least two enzymes, preferably at least three, at least four, at least five, at least six, at least seven or even more enzymes, to obtain a product of biosynthesis. At least one, two, three, four, five, six or seven or even more of the enzymes may be provided as chimeric enzymes, e.g. encoded by a chimeric polynucleotide or nucleic sequence. Specifically the metabolic pathway as described herein comprises coumaric acid as a precursor or intermediate substance. In the process of biosynthesis of a vanilloid of the invention, the coumaric acid is particularly used as a universal intermediate because all vanilloid compounds are derived therefrom according to the new pathway.

The term "polynucleotides" as used herein shall specifically refer to a single or double-stranded deoxyribonucleotide or ribonucleotide polymer of any length, and include as non-limiting examples, coding and non-coding sequences of a gene, recombinant polynucleotides, isolated and purified naturally occurring DNA or RNA sequences, synthetic RNA and DNA sequences, nucleic acid probes, primers, fragments, genetic constructs, vectors and modified polynucleotides. Reference to nucleic acids, nucleic acid molecules, nucleotide sequences and polynucleotide sequences is to be similarly understood.

The term "cluster" as used herein specifically with respect to polynucleotides shall refer to a group of polynucleotides located closely together on the same chromosome whose products play a coordinated role in a specific aspect of cellular primary or secondary metabolism. A cluster as described herein particularly shall refer to a (secondary) metabolite biosynthesis cluster.

The term "precursor" as used herein shall specifically refer to a substrate molecule that is subject to enzymatical reaction and conversion to a product, e.g. a product of biosynthesis or chemical reaction. The term shall specifically apply to a hydroxybenzaldehyde precursor of a vanilloid, e.g. an initial precursor of a metabolic pathway, such as a monosaccharide, in particular glucose, or an initial precursor that is added to a metabolizing cell, such as a natural aromatic amino acid, in particular phenylalanine, tyrosine or tryptophane; or an intermediate of a metabolic pathway, i.e. a molecule obtained by a cell as a metabolite of a cell, which may be further used as a substrate for further enzymatical processing.

A cell metabolizing a precursor as described herein, may specifically produce cell metabolites or desired products by enzymatic reaction in one or more serial steps. For example, a precursor compound may be processed employing a multienzyme complex, e.g. a multienzyme complex which is fully heterologous or in part heterologous, comprising at least two enzymes, preferably at least three, at least four, at least five, at least six, at least seven or even more enzymes, to obtain a product of biosynthesis. Thus, a metabolizing cell comprising the (heterologous) multienzyme complex may be cultivated in a cell culture in the presence of the precursor compound, to obtain the product. Preferably at least one of the heterologous enzymes in the multienzyme complex is a chimeric enzyme.

A specific precursor as described herein is coumaric acid, e.g. for the biosynthesis of a vanilloid or a benzaldehyd precursor thereof. The coumaric acid itself may be produced by biosynthesis by a metabolizing cell, e.g. using an aromatic amino acid as a precursor.

The term "product" as used herein specifically with respect to biosynthesis shall refer to any product of primary and/or secondary metabolism, in particular a compound that may be used as a precursor, intermediate, side-product or end-product of a metabolic pathway.

The term "single step procedure" specifically with respect to an assembly and/or recombination method, means that several process steps of engineering recombinants, like transformation of cells with a gene, the recombination of genes, generation of a mosaic gene and integration of a gene into the target genome, are technically performed in one method step. Thus, there would be no need of in vitro recombination of DNA carriers prior to in vivo recombination, or any repeating cycles of process steps, including those that employ meiosis. Advantageously, the use of meiotic yeast cells can be avoided.

The single step procedure of the invention may even include the expression of such engineered recombinants by a host at the same time. Thereby no further manipulation would be necessary to obtain an expression product.

The term "anchoring" as used herein specifically with respect to a nucleotide acid hybridizing to an element of a genomic integration site, so to insert heterologous sequences into the host cell genome, shall mean the binding of a gene or gene mosaic to an integration sequence through a segment called "anchoring sequence" with partial or complete sequence homology, to enable the integration of such gene or gene mosaic into the integration site of a genome. Specifically the anchoring sequence can be a flanking target region homologous or at least partially homologous to an integration site of a genomic sequence. The preferred anchoring sequence has preferably at least about 70% sequence homology to a target integration site, more preferably at least 80%, 90%, 95% up to 99.5% or complete match with the hybridizing section of the genome.

The term "flanking target sequence" as used herein specifically with respect to a terminal part of a nucleic acid sequence, e.g. a heterologous sequence, that is hybridizing, thereby anchoring, with an element of a genomic integration site, so to insert heterologous sequences into the host cell genome, refers to regions of a nucleotide sequence that are complementary to the target of interest, such as a genomic target integration site, including a site of the gene(s) to be assembled and/or recombined, linear polynucleotides, linear or circular plasmids YAC's and the like. Due to a specific degree of complementation or homology, the flanking target sequence may hybridize with and integrate gene(s) into the target integration site.

As described herein, the length of the flanking target sequence specifically is at least 5 bp, preferably at least 10 bp, more preferably at least 20 bp, 50 bp, 100 bp up to 5,000 bp length. Specifically the flanking target sequence is linked to said gene or is an integral, terminal part of said gene. It is preferred that said the flanking target sequence has homology in the range of 30% to 99.5%, preferably less than 95%, less than 90%, less than 80%, hybridising with the anchoring sequence of said integration site.

Preferably, the flanking target sequence as used herein for in vivo recombination techniques is a single one, e.g. on only one side of a specific nucleotide sequence, e.g. prolonging the 5'-terminal sequence or the 3'terminalk sequence of the specific nucleotide sequence, not on both sides. This provides for an increased chance of generating gene mosaics.

When at least two different flanking target sequences anchoring to the target integration site of the genome are used according to the invention, it is preferred that they do not recombine with each other, preferably they share less than 30% homology.

The integration site as referred to herein may suitably be a defined locus on the host genome, where a high frequency of recombination events would occur. A preferred locus is, for example, the BUD31-HCM1 locus on chromosome III of *S. cerevisiae*. In general, any further loci on the host cell chromosome, e.g. the yeast chromosomes that show recombination at high frequencies but no change of cellular viability is preferred.

The term "genome" of a cell refers to the entirety of an organism's hereditary information, represented by genes and non-coding sequences of DNA, either chromosomal or non-chromosomal genetic elements such as, linear polynucleotides, e.g. including the gene(s) to be assembled and/or recombined, viruses, self-replicating carriers and vectors, plasmids, and transposable elements, including artificial chromosomes and the like.

A preferred method of assembly and/or recombination as described herein may employ selection by direct selection, i.e. determining the desired intermediate or product of successful biosynthesis in the cell culture medium, or else production marker assisted selection of a successful recombination product. The use of tools such as molecular markers or DNA fingerprinting can map the genes of interest. This allows screening of a large repertoire of cells to obtain a selection of cells that possess the trait of interest. The screening is based on the presence or absence of a certain gene.

The term "selection marker" as used according to the invention refers to protein-encoding or non-coding DNA sequences with provides for a mark upon successful integration. Specifically, the protein-encoding marker sequences are selected from the group of nutritional markers, pigment markers, antibiotic resistance markers, antibiotic sensitivity markers, fluorescent markers, knock-in markers, activator/binding domain markers and dominant recessive markers, colorimetric markers, and sequences encoding different subunits of an enzyme, which functions only if two or more subunits are expressed in the same cell. The term shall also refer to a traceable gene to be recombined that provides for the direct determination of the gene mosaic, without the need to use separate marker sequences.

A "nutritional marker" is a marker sequence that encodes a gene product which can compensate an auxotrophy of the cell and thus confer prototrophy on that auxotrophic cell. According to the present invention the term "auxotrophy" means that the cell must be grown in medium containing an essential nutrient that cannot be produced by the auxotrophic cell itself. The gene product of the nutritional marker gene promotes the synthesis of this essential nutrient missing in the auxotrophic cell. By successfully expressing the nutritional marker gene it is then not necessary to add this essential nutrient to the cultivation medium in which the cell is grown.

Preferred marker sequences are URA3, LEU2, HIS3, CAN1, CYH2, TRP1, ADE1 and MET5.

A gene coding for a "pigment marker" is encoding a gene product, which is involved in the synthesis of a pigment which upon expression can stain the cell. Thereby rapid phenotypical detection of cells successfully expressing pigment markers is provided.

An "antibiotic resistance marker" is a gene encoding a gene product, which allows the cell to grow in the presence of antibiotics at a concentration where cells not expressing said product cannot grow.

An "antibiotic sensitivity marker" is a marker gene, wherein the gene product inhibits the growth of cells expressing said marker in the presence of an antibiotic.

A "knock-in" marker is understood as a nucleotide sequence that represents a missing link to a knock-out cell, thus causing the cell to grow upon successful recombination and operation. A knock-out cell is a genetically engineered cell, in which one or more genes have been turned off through a targeted mutation. Such missing genes may be suitably used as knock-in markers.

A "fluorescence marker" shall mean a nucleotide sequence encoding a fluorophore that is detectable by emitting the respective fluorescence signal. Cells may easily be sorted by well-known techniques of flow cytometry on the basis of differential fluorescent labeling.

"Recombinant," as used herein, means that a particular nucleic acid (DNA or RNA) is the product of various combinations of cloning, restriction, ligation, and/or in vitro DNA synthesis steps resulting in a construct having a structural coding or non-coding sequence distinguishable from endogenous nucleic acids found in natural systems. Generally, DNA sequences encoding the structural coding sequence can be assembled from cDNA fragments and short oligonucleotide linkers, or from a series of synthetic oligonucleotides, to provide a synthetic nucleic acid which is capable of being expressed from a recombinant transcriptional unit contained in a cell or in a cell-free transcription and translation system. Such sequences can be provided in the form of an open reading frame uninterrupted by internal non-translated sequences, or introns, which are typically present in eukaryotic genes. Genomic DNA comprising the relevant sequences can also be used in the formation of a recombinant gene or transcriptional unit. Sequences of non-translated DNA may be present 5' or 3' from the open reading frame, where such sequences do not interfere with manipulation or expression of the coding regions, and may indeed act to modulate production of a desired product by various mechanisms.

Thus, e.g., the term "recombinant" polynucleotide or nucleic acid refers to one which is not naturally occurring, e.g., is made by the artificial combination of two otherwise separated segments of sequence through human intervention. This artificial combination is often accomplished by the artificial manipulation of isolated segments of nucleic acids, e.g., by genetic engineering techniques. For example, it is performed to join together nucleic acid segments of desired functions to generate a desired combination of functions. The term "recombination" shall specifically apply to assembly of polynucleotides, joining together such polynucleotides or parts thereof, with or without recombination to achieve a cross-over or a gene mosaic.

The term "recombinant" as used herein, specifically with respect to nucleic acid sequences shall refer to nucleic acids or polynucleotides produced by recombinant DNA techniques, e.g. a DNA construct comprising a polynucleotide heterologous to a host cell, which is optionally incorporated into the host cell. A chimeric nucleotide sequence may specifically be produced as recombinant molecule.

The term "recombinant" as used herein, specifically with respect to enzymes shall refer to enzymes produced by recombinant DNA techniques, i.e., produced from cells transformed by an exogenous DNA construct encoding the desired enzyme. "Synthetic" enzymes are those prepared by chemical synthesis. A chimeric enzyme may specifically be produced as recombinant molecule.

The term "recombinant host", also referred to as a "genetically modified host cell" denotes a host cell that comprises a heterologous nucleic acid.

The term "repertoire" specifically with respect to a variety of recombinant elements, such as recombinant metabolic pathways or recombinant cells, is herein understood as a population of diverse variants, for example nucleic acid variants which differ in nucleotide sequence or polypeptide variants which differ in amino acid sequence, or host cells or clones of recombinant host cells, e.g. comprising a variety of heterologous enzymes or a variety of metabolic pathways. A library of the invention will encompass a repertoire of cells or a repertoire of aromatic compounds produced as metabolites by such cells. According to the present invention, a repertoire of clones is designed to possess a metabolic pathway, wherein a multienzyme complex is employed comprising at least one chimeric enzyme, particularly wherein said cells differ from each other in the number and/or type of gene mosaic, so to comprise a different cluster of polynucleotides or a nucleic acid sequence with different gene mosaic(s), e.g. such that the enzymatic activity of said multienzyme complex or said products of biosynthesis or the product yield will differ.

The invention particularly provides for a library obtainable by a method of engineering a metabolic pathway by in vivo recombination, e.g. by homeologous recombination, so to obtain a variety of cells with different polynucleotides involved in the metabolic pathway. Preferred libraries comprising at least 100 different clones, preferably at least 1,000 different clones or even more, which clones produce the desired product of biosynthesis, each of the clones is considered a library member. The variants specifically may contain at least 1%, more preferred at least 10%, more preferred at least 20%, more preferred at least 40%, more preferred at least 60%, more preferred at least 80%, even more preferred at least 90%, more preferably at least 95% functional ORF's. The preferred library obtainable according to the present invention specifically comprises a high percentage of gene mosaics within a functional open reading frame (ORF), preferably at least 80%.

It is preferred to characterize the variant clones, e.g. through genomic analysis or by determining the structure and function of secondary metabolites produced by the variant. The variant producing a desired product of biosynthesis, e.g. a vanilloid, at high levels, may be selected to further engineer a recombinant production cell line for industrial production purposes.

Therefore, the invention is particularly based on the finding of a new metabolic pathway or variants of such new metabolic pathway, which may be used in the production of vanilloids and related compounds by recombinant host cells. Key elements of such new pathway are coumaric acid and further enzymes among them a crotonase, to provide for the biosynthesis of vanilloids or benzaldehyde precursors of such vanilloids. The preferred host cells comprise a heterologous cluster of polynucleotides encoding enzymes or enzyme variants, such as at least one chimeric enzyme comprising a gene mosaic.

In a specific embodiment enzyme variants are obtained by such gene mosaics, e.g. directly by recombination and eventual assembly of the gene mosaics, or as a consequence of such gene mosaic, e.g. through a sequence of enzymatic processes. An exemplary method refers to cinnamate-4-hydrolase (C4H) and C4H generated genes coding for enzymes having improved or new enzymologic properties, e.g. as determined in a functional assay.

A specifically preferred method employs recombination and assembly of enzymes and enzyme pathways, comprising at least 2 enzymes having biological activity, to obtain a multienzyme complex, enzyme variants, pathways or pathway variants having respective wild-type enzymes and/or enzymes with gene mosaics, for processing biological source material or arrays to produce the desired products of biosynthesis at desired levels.

Genetic pathways can be constructed in a combinatorial fashion such that each member in the combinatorial library has a different combination of gene variants. For example, a combinatorial library of variants can be constructed from individual DNA elements, where different fragments are recombined and assembled and wherein each of the different fragments has several variants. The recombination and assembly of a metabolic pathway may not need the presence of a marker sequence to prove the successful engineering. The expression of a metabolite in a desired way would already be indicative for the working example. The successful recombination and assembly of the metabolic pathway may, for example, be determined by the detection of the secondary metabolite in the cell culture medium.

It may be desirable simply to assemble, e.g. to string together and optionally mix naturally-occurring polynucleotides of different origin, wherein at least one is heterologous to the host cell, which polynucleotides encode specific wild-type enzymes. It may also be desirable to provide for variants of such polynucleotides, e.g. by diversification through mutation techniques, e.g. to create variants (multiplicities) of metabolic pathways. Metabolic pathways, which do not exist in nature, can be constructed in this manner. Thus, enzymes which are present in one organism that operate on a desired substrate produced by a different organism lacking such a downstream enzyme, can be encoded in the same organism by virtue of constructing the assembly of genes or partial genes to obtain recombined enzymes. Multiple enzymes can be included to construct complex metabolic pathways. This is advantageous, if a cluster of polypeptides or partial polypeptides shall be arranged according to their biochemical function within the pathway.

Preferably the library is a yeast library and the yeast host cell preferably exhibits the metabolic pathway with the desired biosynthesis activities. In specific embodiments, the products are staying within the cell or are secreted out of the cell. The yeast host cell is preferably selected from the genera *Saccharomyces, Pichia, Hansenula, Schizosaccharomyces, Kluyveromyces, Yarrowia* and *Candida*. Most preferred, the host cell used for engineering the heterologous metabolic pathway by assembly and/or recombination is *Saccharomyces cerevisiae*.

Any recombination competent eukaryotic or prokaryotic host cell can be used for generating a cluster of polynucleotides and/or a gene mosaic by somatic in vivo recombination according to the present invention. According to a preferred embodiment of the invention, the cell is a repair deficient cell, e.g. a nucleic acid repair deficient cell, such as with DNA repair deficiency, i.e. a DNA repair deficient cell, or an MMR deficient cell.

Specifically, the cell is a eukaryotic cell, preferably a fungal, mammalian or plant cell, or prokaryotic cell.

Preferably the cell is an *Aspergillus* sp or a fungal cell, preferably, it can be selected from the group consisting of the genera *Saccharomyces, Candida, Kluyveromyces, Hansenula, Schizosaccaromyces, Yarrowia, Pichia* and *Aspergillus*.

Preferably haploid strains, such as haploid yeast strains are employed.

Alternatively, prokaryotes, such as *E. coli, Bacillus, Streptomyces*, or mammalian cells, like HeLa cells or Jurkat cells, or plant cells, like *Arabidopsis*, may be used.

Upon engineering the appropriate metabolic pathway by in vivo recombination techniques, it may be advantageous to excise the cluster of polynucleotides and incorporate the cluster into a production host cell. Once synthesized as metabolites or intermediates of such metabolites by selected clones comprising the new heterologous cluster and optionally the gene mosaic, they are typically produced on the large scale by suitable expression systems, e.g. by microbial production, and/or by (further) in vitro synthesis process steps.

Preferably the production host cell is a yeast cell.

In accordance with the present invention there may be conventional molecular biology, microbiology, and recombinant DNA techniques employed which are within the skill of the art.

For in vivo recombination, the gene to be recombined with the genome or other genes is used to transfect the host using standard transfection techniques. In a suitable embodiment DNA providing an origin of replication is included in the construct. The origin of replication may be suitably selected by the skilled person. Depending on the nature of the genes, a supplemental origin of replication may not be required if sequences are already present with the genes or genome that are operable as origins of replication themselves.

Synthetic nucleic acid sequences or cassettes and subsets may be produced in the form of linear polynucleotides, plasmids, megaplasmids, synthetic or artificial chromosomes, such as plant, bacterial, mammalian or yeast artificial chromosomes.

A cell may be transformed by exogenous or heterologous DNA when such DNA has been introduced inside the cell. The transforming DNA may or may not be integrated, i.e. covalently linked into the genome of the cell. In prokaryotes, yeast, and mammalian cells for example, the transforming DNA may be maintained on an episomal element such as a plasmid. With respect to eukaryotic cells, a stably transformed cell is one in which the transforming DNA has become integrated into a chromosome so that it is inherited by daughter cells through chromosome replication. This stability is demonstrated by the ability of the eukaryotic cell to establish cell lines or clones comprised of a population of daughter cells containing the transforming DNA.

The diverse genes substrates may be incorporated into plasmids. The plasmids are often standard cloning vectors, e.g., bacterial multicopy plasmids. The substrates can be incorporated into the same or different plasmids. Often at least two different types of plasmid having different types of selectable markers are used to allow selection for cells containing at least two types of vector.

Plasmids containing diverse gene substrates are initially introduced into cells by any method (e.g., chemical transformation, natural competence, electroporation, biolistics, packaging into phage or viral systems). Often, the plasmids are present at or near saturating concentration (with respect to maximum transfection capacity) to increase the probability of more than one plasmid entering the same cell. The plasmids containing the various substrates can be transfected simultaneously or in multiple rounds. For example, in the latter approach cells can be transfected with a first aliquot of plasmid, transfectants selected and propagated, and then infected with a second aliquot of plasmid. Preferred plasmids are, for example, pUC and pBluscribe derivatives as pMXY9, pMXY12 and pMIX-LAM or YAC derivatives as YCp50.

The rate of evolution can be increased by allowing all gene substrates to participate in recombination. Such can be achieved by subjecting transfected cells to electroporation. The conditions for electroporation are the same as those conventionally used for introducing exogenous DNA into cells. The rate of evolution can also be increased by fusing cells to induce exchange of plasmids or chromosomes. Fusion can be induced by chemical agents, such as PEG, or viral proteins, such as influenza virus hemagglutinin, HSV-1 gB and gD. The rate of evolution can also be increased by use of mutator host cells (e.g., Mut L, S, D, T, H in bacteria, analogous mutants in yeast, and Ataxia telangiectasia human cell lines).

In a preferred embodiment of the invention the assembly of a mosaic gene, its recombination with a host genome, and further the expression of the mosaic gene to produce a recombinant polypeptide of interest or a metabolite of said host cell, is performed in a single step procedure.

Cells bearing the recombined genes may be subject to screening or selection for a desired function. For example, if the substrate being evolved contains a drug resistance gene, one would select for drug resistance.

Specifically metabolites of aromatic amino acids, such as phenylalanine, tyrosine or and tryptophan, such as those produced by plants or yeast by enzyme activity, or any intermediates or derivatives may be produced in a novel way. The repertoire of enzyme variants thus leads to diverse metabolites formation, which is then screened for the desired structure and function.

Phe and Tyr are closely related. They contain a benzene ring which is additionally hydroxylated in tyrosine. Tyrosine is synthesized directly from the essential amino acid phenylalanine. Tryptophan contains a conjugated indole ring. These metabolic relations give rise to an intricate nutritional dependence.

In plants, the shikimate pathway produces the compound phenylalanine for the biosynthesis of phenylpropanoids. The hydroxycinnamates and esters produced by a combination of reductases, oxygenases, and transferases define the specific pattern of metabolites in an organ and depending on their development this profile is characteristic for each plant species. The initial three steps of the phenylpropanoid pathway are e.g. catalyzed by PAL, C4H and 4CL enzymes and provide the basis for all subsequent branches and resulting metabolites e.g.: flavonoids, lignins, phenylpropanoid esters, aurones, isoflavones, stilbenes, proanthocyanins, etc.

For example, PAL is known to catalyze the deamination of Phe to give cinnamic acid, which is the first step in the phenylpropanoid pathway and a regulation point between primary and secondary metabolism. Phenylpropanoid compounds are precursors to a range of phenolic compounds with many functions in nature, including lignin, flavonoids, isoflavonoids, coumarins and stilbenes.

Products of metabolic pathways are typically natural small molecules or variants thereof, e.g. differing in glycosylation, acylation, amination, hydroxylation or methylation with improved or new functions. These metabolites are suitably as fragrants or flavors or as therapeutic molecule (e.g. anti-infective or for the treatment of cancer).

Specific examples relate to a novel yeast cell factory for production of vanillin from sugar source, using somatic in vivo assembly and recombination of artificial metabolic pathway. A novel yeast cell factory for production of vanillin from sugar source, using somatic in vivo assembly and recombination of artificial metabolic pathway is specifically provided. According to a specific example, an artificial pathway for the production of vanillin from a carbon source is provided in microorganism. The exemplary bioconversion scheme requires six steps of enzyme-catalyzed conversion. Gene encoding enzymes may be integrated into yeast genome by somatic in vivo recombination. Prevention of reduction of vanillin to vanillyl alcohol may specifically be achieved by knockout of the host alcohol dehydrogenase ADH6. ADH6 may be disrupted by integrating a carboxylic acid reductase protein with its activating coupling protein phosphopantetheinyl transferase.

The examples described herein are illustrative of the present invention and are not intended to be limitations thereon. Different embodiments of the present invention have been described according to the present invention. Many modifications and variations may be made to the techniques described and illustrated herein without departing from the spirit and scope of the invention. Accordingly, it should be understood that the examples are illustrative only and are not limiting upon the scope of the invention.

EXAMPLES

Example 1: Artificial Vanillin Pathway: Metabolic Pathway to Produce Vanillin Using Phenylalanine as Precursor Compound Since vanillin is not an endogenous metabolite, it is necessary to recreate a synthetic production pathway in yeast. The vanillin synthesis starts as all phenylpropanoids with phenylalanine which is produced endogenously by the cell. Six enzymes are required for the conversion of L-phenylalanine to vanillin (FIG. 1). Phenylalanine is converted to coumarate by the successive action of the enzymes phenylalanine ammonia lyase (PAL), cinnamate-4-hydroxylase (C4H). The following step is the reduction chain reaction of the coumaric acid leading to the 4-hydroxybenzaldehyde. The reaction is initiated by the activation of coumaric acid to coumaroyl-CoA provided by 4CL enzyme (4-Coumarate Coenzyme A Ligase), followed by a β-oxidation performed by ECH enzyme (enoyl-CoA hydratase/aldolase, crotonase family enzyme). The next step is the hydroxylation on 3-position of the phenyl ring carried out by HBH enzyme (hydroxybenzoic acid hydroxylase, 3-monooxygenase enzyme family). The final step is the O-methylation leading to vanillin final product. This step is catalyzed by the COMT enzyme (caffeic acid O-methyltransferase, O-methyltransferase enzyme family). In order to lower endogenous conversion of aldehyde intermediate product, carboxylic acid reductase protein was added.

In S. cerevisiae, the CAR enzyme required activation by phosphopantetheinylation, and this was achieved by co-expression of a phosphopantetheinyl transferase.

a) Vanillin Pathway Assembly in Yeast Host Cell

All of the Saccharomyces cerevisiae strains used in this work were isogenic haploids from BY4741 and were obtained from EUROSCARF (haploid a-mater BY00 or α-mater BY10). Yeast strain BY47 derived from a strain collection that contains knock outs of auxotrophic (-ura3, -leu2, his3) marker genes. The different strains and relevant genotypes are listed in Table 2. Enrichment and propagation of clones were made in YPD liquid cultures (10 g/l Bacto-yeast extract, 20 g/l bacto-peptone and 2% dextrose) at 30° C. Recombinants were selected on dropout agar plates (YNB+CSM) in the absence of uracil or leucine or histidine. The gene defects in uracil, histidine and leucine biosynthetic pathway result in auxotrophy. For homeologous recombination, we used a mismatch deficient strain (haploid a-mater BY00775 or a-mater BY10775, sgs1-, Euroscarf). All ORF used for the pathway were synthesized at GeneArt (Germany) and then amplified by PCR. Amplification was performed using high fidelity PhusionTaq (New England Biolabs). Amplicons were cleaned up by using the Wizard PCR Clean-up System (Promega) and used for transformation assays.

TABLE 2

Genotype of S. cerevisiae strains used in this work (EUROSCARF)

| Defective gene (ORF) | Acc. N° | Strain | Genotype |
|---|---|---|---|
| Wild type strains | Y00000 | BY4741 | MATα: his3Δ1; leu2Δ0; met15Δ0; ura3Δ0 |
|  | Y10000 | BY4741 | MATα: his3Δ1; leu2Δ0; lys1Δ0; ura3Δ0 |
| YMR190c (Δsgs1) | Y00775 | BY4741 | MATa: his3Δ1; leu2Δ0; met15Δ0; ura3Δ0; YMR191c::kanMX4 |
|  | Y10775 | BY4741 | MATa: his3Δ1; leu2Δ0; lys1Δ0; ura3Δ0; YMR191c::kanMX4 |

A Three-step approach was employed to identify heterologous enzymes for the synthetic vanillin pathway. First candidates were individually expressed in yeast to evaluate enzyme activity. Second, once all the enzymes identified, complete pathway was assembled using a somatic in vivo DNA assembly. And third, evolution was performed on vanillin pathway using homeologous in vivo recombination and assembly in yeast.

b) Characterization of Exogenous Proteins Activities Individually Expressed in Yeast.

First, candidate enzymes were individually expressed in S. cerevisiae and tested for activity (see Table 3 for details on the sources of the sequences).

TABLE 3

Reference identities of the genes used in this example

| Gene | Species | Reference (NCBI nucleotide database) | ORF length (bp) |
|---|---|---|---|
| PAL | Petroselinum crispum | X81158.1 GI:534892 | 2157 |
|  | Populus trichocarpa x Populus deltoides | L11747.1 GI:169453 | 2148 |
| C4H | Glycine max | FJ770468.1 GI:225194700 | 1521 |
|  | Petroselinum crispum | Q43033.1 GI:3915088 | 1521 |
| 4CL | Populus tremuloides | AF041049.1 GI:3258634 | 1713 |
| ECH | Pseudomonas fluorescens | AJ536325.1 | 831 |
|  | Azotobacter vinelandii | YP_002798614.1 GI:226943541 | 831 |
| HBH | Pseudomonas aeruginosa | ZP_07797957.1 GI:313112178 | 1185 |
|  | Azotobacter vinelandii | NC_012560.1 GI:226943557 | 1185 |
| COMT | Medicago sativa | ACY06328.1 GI:261889456 | 1098 |
|  | Vanilla planifolia | AAS64572.1 GI:45444737 | 1098 |
| CAR | Nocardia iowensis | AAR91681.1 GI:40796035 | 3525 |
| PPTase | Nocardia iowensis | ABI83656.1 GI:114848891 | 669 |
| URA3 | Kluyveromyces lactis (pJJH726: nt 1 to 2246) | AF298788.1 GI:11344892 | 2146 |
| LEU2 | Saccharomyces cerevisiae | GI:259144874 | 2218 |
| CPR | Populus trichocarpa x Populus deltoides | AF302497.1 GI:13183563 | 2139 |

For each gene, recombinant clones were constructed using in vivo homologous recombination at bud31 locus (FIG. 2). Integration fragments were designed. T 5' and T 3' correspond to the bud31 target sequences on the yeast genome allowing homologous integration onto the chromosome locus. URA and LEU are the flanking markers for the double selection. Overlapping sequences correspond to the 5' part and the 3' part of the marker genes. All integration fragments IF1-IF2-IF4 and IF5 were amplified by PCR and amplicons were purified using the Wizard PCR Clean-up System (Promega). Synthetized ORF was amplified from GeneArt plasmid. The 5' end of the upstream oligonucleotides used for amplifying the gene of interest contains a sequence of 40 nucleotides homologous with the 3'end of the pGAL1 promoter. The downstream oligonucleotides contained a 40-nt sequence homologous with the 5'end of the tCYC terminator. After assembly by homologous recombination in yeast, the double selection allows selection of the recombinants.

For each transformation, five recombinant clones were randomly chosen and the correct integration of the cluster was analyzed by targeted PCRs using gDNA as template. Colony PCR has been done as described below. A minimal amount of cells (edge of a 10 μl tip) was re-suspended in a PCR tube containing 15 μl of lysis mix (100 mM Tris-HCl pH=7.5+5 μL zymolase (10 mg/mL) from Sigma). The tubes were first incubated 20 min at 20° C., then 5 min at 37° C. and finally 5 min at 95° C. 2 μl of each lysate mix were used in 25-100 μl DreamTaq PCR reactions as indicated by the supplier (Fermentas). Amplified DNAs for sequencing were separated from primers using the Wizard PCR Clean-up System (Promega).

Then recombinant clones were cultured in induction medium to allow synthesis of proteins. As in this construction, gene expression is controlled by inducible GAL1 promoters, cells were grown on YPAGAL medium (YEP medium with galactose as the sole carbon source). After growth for 24 hours, cells were fed with 500 μM of appropriate substrate. Supernatants were then analyzed by High performance liquid chromatography (HPLC) to identify the appropriate product. Intermediates in vanillin biosynthesis and vanillin catabolites were analyzed using an Agilent 1200 series HPLC system using an ACE5-C18 column (4.6 by 250 mm, 5-μm particle size). An acetonitrile/water gradient was determined and a diode array detector was used to detect eluted compounds by their UV fluorescence at 260 nm, 280 nm and 320 nm. All standards were obtained from Sigma Aldrich.

c) Assembly of Vanillin Pathway.

Second, once all the enzymes identified, the complete pathway was assembled using a somatic in vivo DNA assembly. 8 fragments containing (F1 to F8) the 6 genes of the vanillin pathway were designed by computational analysis. The fragments, the ORF's as well as the upstream and downstream sequences are shown in FIG. 3 (for the amplification of each fragment, see Table 4 and Table 5, for details on the sources of the sequences, see Table 3).

TABLE 4

Primers used for the amplification of the fragments used in homologous recombination.

| primer | Sequence 5' → 3' | function |
|---|---|---|
| OL01 | SEQ ID 16:<br>CTGTGCTGTCTGCGCTGC | Amplification F1 |
| OL02 | SEQ ID 17:<br>ATCGTGCAAAACAACTCTGTA<br>TTCAG | |
| OL126 | SEQ ID 18:<br>CCAGAAGATGCTCCATTGGAA<br>GAT | Amplification F2 |
| OL127 | SEQ ID 19:<br>TTAAGACATAGTAGTAGCAGT<br>AGCCAA | |
| OL132 | SEQ ID 20:<br>ATGATGTCTGTTGCTACTGTT<br>GAACCA | Amplification F3 |
| OL133 | SEQ ID 21:<br>TTAACAAATTGGCAATGGAGA<br>ACCGTTC | |
| OL09 | SEQ ID 22:<br>ATGGAAACTGTTACTAAGAAC<br>GGTTA | Amplification F4 |
| OL10 | SEQ ID 23:<br>TTAGAAAGATCTTGGCTTAGC<br>AACA | |
| OL140 | SEQ ID 24:<br>ATGGATTGTTGTTGTTGGAA<br>AAGACTT | Amplification F5 |
| OL219 | SEQ ID 25:<br>ATGTCTAACTACGAAGGTAGA<br>TGGACT | |

TABLE 4-continued

Primers used for the amplification of the fragments used in homologous recombination.

| primer | Sequence 5' → 3' | function |
|---|---|---|
| OL222 | SEQ ID 26:<br>TCATCTCTTGTAAGCTTGCAA<br>ACCTG | Amplification F6 |
| OL149 | SEQ ID 27:<br>TTATTCAATTTCTTCGTATGG<br>CAAACCAACGTA | |
| OL156 | SEQ ID 28:<br>ATGAAGACTCAAGTTGCTATT<br>ATTGGTG | Amplification F7 |
| OL157 | SEQ ID 29:<br>TTAAACCTTCTTCAAGAATTC<br>CATAATGTAAGTGTTGAAAG | |
| OL15 | SEQ ID 30:<br>ATGGGTTCTACTGGTGAAACT<br>CAA | Amplification F8 |
| OL16 | SEQ ID 31:<br>GCGCATGTGTCCGATCTTTG | |

TABLE 5

Reference identities of the upstream and downstream sequences for the vanillin genes used in the example 1 and 2.

| | Species | Reference (NCBI nucleotide database) | Length (bp) |
|---|---|---|---|
| Promoter | | | |
| pMET2Ppx | *Saccharomyces paradoxus* (nt 14989 to 15458) | AABY01000028.1 GI:29362583 | 474 |
| pGAL1/ pGAL10 | pESC-URA (nt 2271-2934) | AF063585.2 GI:6446607 | 664 |
| pMET2Sby | *Saccharomyces bayanus* (nt 4779 to 5247) | AACG02000186.1 GI:77693693 | 479 |
| pADH1 | *Saccharomyces cerevisiae* (nt 160595 to 162095 [C]) | NC_001147.5 GI:84626310 | 1501 |
| pGDP | *Saccharomyces cerevisiae* | Part:BBa K124002 | 680 |
| Terminator | | | |
| tTPISce | *Saccharomyces cerevisiae* (nt 1406 to 1649) | J01366.1 GI:173007 | 243 |
| tPGKSce | *Saccharomyces cerevisiae* (nt 1553 to 1839) | J01342.1 GI:172143 | 286 |
| tADH1Sce | *Saccharomyces cerevisiae* (nt 1798 to 1991) | V01292.1 GI:3338 | 194 |
| tCYC1Sce | *Saccharomyces cerevisiae* (nt 559 to 838) | V01298.1 GI:3626 | 279 |

Fragment hybridizes and recombines together in the region of the entire ORF of each couple of gene. By that way, the whole pathway is assembled in the yeast cell, and then integrated into the chromosome. Tg 5' and Tg 3' correspond to the target sequences on the yeast genome that corresponds to the insertion site in the BUD 31 locus of the yeast chromosome triggering the homologous integration into the desired chromosome site. HIS3 and LEU2 are the flanking markers enabling the double selection of the recombinant pathway. Each gene is under the control of one promoter and one terminator sequences allowing its expression in yeast cells. After assembly of the fragments by homologous recombination in yeast, a functional complete pathway of 20291 bp is reconstituted and the double selection permits the isolation of recombinants.

All fragments were amplified by PCR and amplicons were purified using the Wizard PCR Clean-up System (Promega). Transformations of competent yeast cells were performed as described by Gietz and Woods (Transformation of yeast by the LiAc/ss Carrier DNA/PEG method. *Meth. Enzymol.*, 350, 87-96) with some modifications to optimize the volume of DNA input. Cells were precultured in YPD medium and then used to inoculate new rich medium. They were harvested when $OD_{600}$ reach out 0.6, the pellet washed twice and concentrated in 1/50 volume. Competent cells were added to the transformation PEG/LiAC/ssDNA mix with 250 ng of each fragment (F1-F2-F3-F4-F5-F6-F7 and F8). Additionally competent cells were transformed with no DNA (negative control). Selection of recombinant clones was performed on media without His and Leu. After 3 days clones transformed with the various fragments were observed on selection media. 3 clones (Y00VAN) were randomly chosen for sequence and activity analysis. Isolated and genomic DNA (gDNA) was prepared using the Wizard Genomic DNA purification kit (Promega). Then the 7 vanillin genes of each of these clones were amplified with specific primers that also verified the correct assembly of the fragments. Analysis of clones revealed that the genes had assembled resulting in correct ORFs.

d) Expression of Vanillin Pathway in Yeast.

Vanillin Pathway Expression in Wild Type Yeast Strain (Y00VAN).

We first analyzed vanillin pathway in wild type yeast strain without expression of CAR protein. As some vanillin genes are controlled by inducible promoters such as GAL1/10 for ECH and HBH and MET2 for PAL. Yeast cultures were grown under inducing conditions: minimal medium containing galactose as the sole carbon source in absence of methionine and with addition of phenylalanine as precursors (10 mM). Culture was performed for at least 60 hours. They were harvested by centrifugation and supernatants recovered. As controls, we used the Y00 wild type strain (no vanillin gene) cultured under the same conditions as Y00VAN (clone expressing vanillin pathway genes), and the medium without yeast. HPLC was used to measure the production of vanillin and pathway intermediates in *S. cerevisiae* cultures. Analysis showed that chromatograms from cells expressing vanillin pathway genes (Y00VAN) contained additional peaks compared to an Y00 control. These peaks were identified by comparison to our library of molecules. Thus, cinnamic acid, coumaric acid, 4 hydroxybenzoic acid, 3-4 dihydroxybenzoic acid and vanillic acid were identified. No 4 hydroxybenzaldehyde, 3-4 dihydroxybenzaldehyde and vanillin were detected. When Y00VAN cultures are fed with 500 µM of 3-4 dihydroxybenzaldehyde, vanillin, vanillic acid and vanillyl alcohol are detected. The deviation from the acid derivatives takes place immediately after the reduction step of the chain. Finally when cells are fed with 3-4 dihydroxybenzaldehyde in total induction medium, most intermediate precursors as well as final products are detected (FIG. 4).

Figure 5:
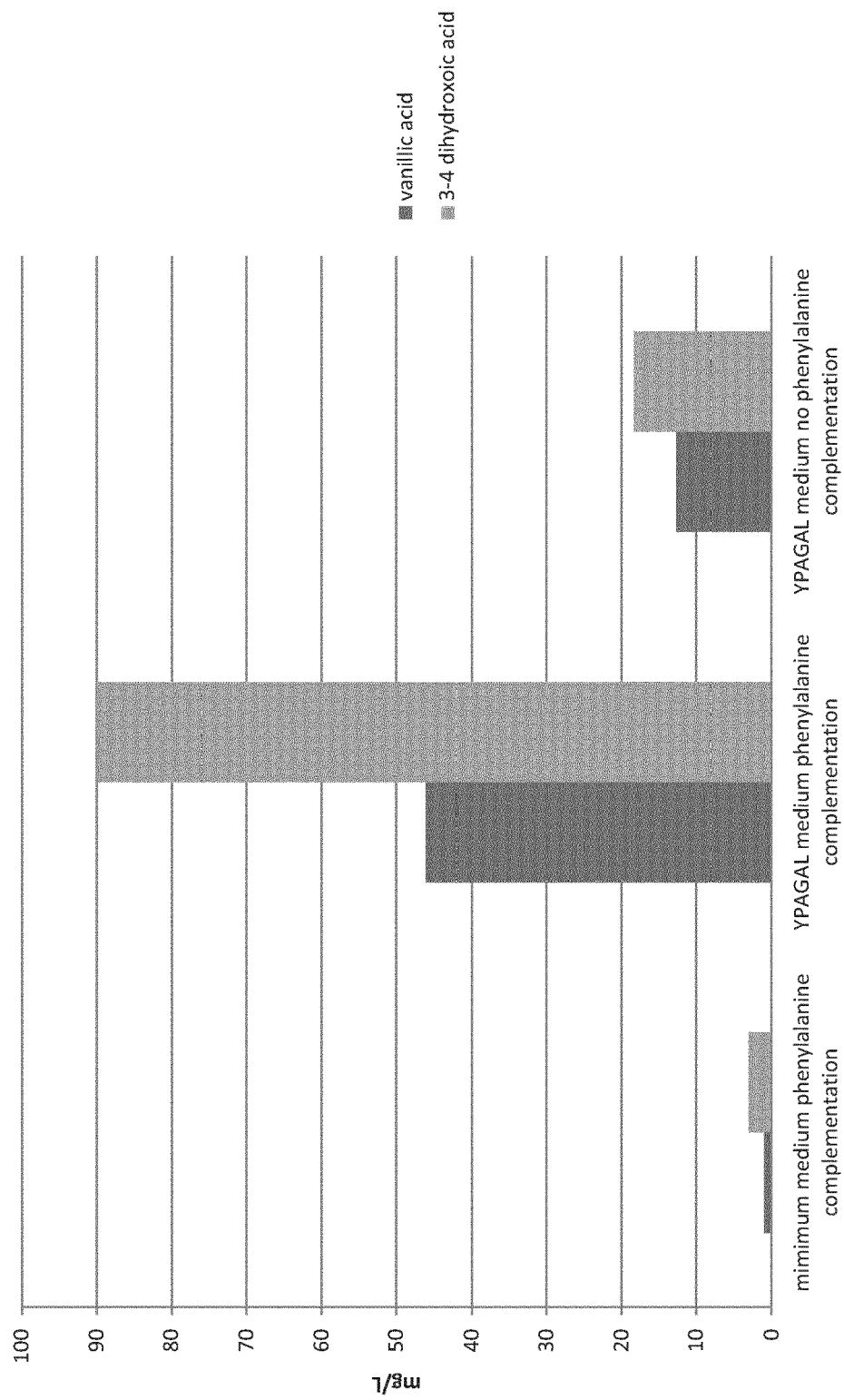

Y00VAN was then grown in rich YPAGAL medium: YEP medium with galactose as the sole carbon source and with phenylalanine as precursor (10 mM). We assume that the amount of methionine contained in the medium is rapidly consumed and the pMET promoter is then induced. Higher cell growth was observed using rich medium. Supernatant was analysed using HPLC and compared with Y00 supernatant composition. After 60 h, large amounts of 3-4 dihydroxybenzoic acid and vanillic acid were detected in supernatant (FIG. 5).

When the culture is not supplemented by exogenous phenylanine, the PAL protein uses endogenous phenylalanine. The pathway is fully functional as 3-4 dihydroxybenzoic acid and vanillic acid were detected but the yield is reduced by 4 times compared with the phenylalanine supplemented medium (FIG. 5). Endogenous biosynthesis of phenylalnine proceeds via a common pathway with other aromatic amino acids to chorismate and feeds vanillin pathway.

Vanillin Pathway Expression in Modified Yeast Strain (Y00CP).

In vanillin pathway, many intermediate precursors are aldehydes. However aldehydes are known to be substrates of many endogenous enzymes leading to relative alcohol or acid derivative. In Y00VAN, aldehydes are oxidized in acid derivatives immediately after reduction chain reaction and no vanillin is detected. In order to lower this conversion a carboxylic acid reductase protein was added with its activating coupling protein phosphopanteteinyl transferase. The bicistronic construction was integrated to yeast genome by homologous recombination using URA as selection marker into ADH6 locus. Prevention of reduction of vanillin to vanillyl alcohol was achieved by knockout of the host alcohol dehydrogenase ADH6. In order to take off selection marker, flanking repeated sequences were added to URA3 gene in order to permit URA3 gene excision. Recombinant cells were selected on—URA selective medium and the right integration was verified by PCR. URA3 encodes an oritidine 5' phosphate decarboxylase that is implied in uracil synthesis. 5FOA (5 fluoroorotic acid) is converted in 5 fluorouracil by URA3. This toxic metabolite is a selective pressure in favor of excision of URA3 with flanking repeated sequences leading to ura3 genotype. Yeast strain was named Y0CP. When Y0CP culture is fed with 500 µM of vanillic acid, vanillin is detected in supernatant indicating that CAR is functional.

The recombinant strain Y0CPVAN comprises the complete vanillin pathway.

e) Evolution Using Homeologous Recombination and Assembly of Genes From Vanillin Pathway.

A library of complex mosaic genes from the vanillin pathway was generated using homeologous recombination and assembly. In this experiment two homologous genes of each enzyme were assembled/recombined. In order to proceed homeologous recombination three fragments were re-designed by introducing related sequences of pathway genes FIG. 7 (for the amplification of F4', F6' and F7' fragment, see Table 6). F04' contains homeologous gene of PAL and C4H that share 91 and 90% homology with other parental sequence respectively. F06' contains homeologous gene of ECH and HBH that share 88 and 77% homology with other parental sequence respectively. F07' contains homeologous COMT that share 73% homology with the other parental sequence.

Each fragment hybridizes and recombines in the region of the entire ORF of each homeologous gene. By that way, the whole mosaic pathway is assembled, recombined and integrated into the chromosome in the mismatch repair deficient yeast cell. After assembly of the fragments by homeologous recombination in yeast, a functional complete pathway of 20291 bp is reconstituted and the double selection permits the isolation of recombinants.

TABLE 6

Primers used for the amplification of the replaced fragments

| primer | Sequence 5' → 3' | function |
|---|---|---|
| OL19 | SEQ ID 32: ATGGCTTACGTTAAC GGTACTACT | Amplification Frag. 4' |
| OL20 | SEQ ID 33: TTA CAA AGA TCT TGG CTT ACA AAC AAT A | |
| OL275 | SEQ ID 34: TTATCTCTTGTAAGC TTGCAAACCTGG | Amplification Frag. 6' |
| OL276 | SEQ ID 35: TTAAGCAATTTCTTC GTATGGCAAACCAAC | |
| OL156 | SEQ ID 36: ATGAAGACTCAAGTT GCTATTATTGGTG | Amplification Frag. 7' |
| OL281 | SEQ ID 37: TCACTTGTTGAATTC CATAACCCAAACGTT | |

Fragments F1-F2-F3-F4'-F5-F6'-F7' and F8 were amplified by PCR and purified amplicons were used to transform mismatch repair yeast. Y10775CP cells were precultured in YPD medium and then used to inoculate new rich medium. They were harvested when OD600 reach out 0.6, the pellet washed twice and concentrated in 1/50 volume. Competent cells were added to the transformation PEG/LiAC/ssDNA mix with 250 ng of each fragment. Additionally competent cells were transformed with no DNA (negative control). Selection of recombinant clones was performed on media without His and Leu. After 3 days clones transformed with the different fragments were observed on selection media. 3 clones (Y00VANev) were randomly chosen for sequence and activity analysis. Isolated and genomic DNA (gDNA) was prepared using the Wizard Genomic DNA purification kit (Promega). Then the 7 vanillin genes of each of these clones were amplified with specific primers that also verified the correct assembly of the fragments. The analysis of clones revealed that the genes had assembled resulting in correct ORFs.

Bioconversion of Vanillin From a Sugar Source

Vanillin pathway was assembled in modified host strain. In order to reduce vanillin acid into vanillin, carboxylic acid reductase was added with its activating coupling protein phosphopantetheinyl transferase. The bicistronic construction was integrated to yeast genome by homologous recombination using URA as selection marker into ADH6 locus. Prevention of reduction of vanillin to vanillyl alcohol was achieved by knockout of the host alcohol dehydrogenase ADH6. Then modified strain was precultured in YPD medium and then used to inoculate new rich medium. They were harvested when $OD_{600}$ reach out 0.6, the pellet washed twice and concentrated in 1/50 volume. Competent cells were added to the transformation PEG/LiAC/ssDNA mix with 250 ng of each fragment (F1-F2-F3-F4-F5-F6-F7 and F8). Selection of recombinant clones was performed on media without His and Leu. After 3 days clones transformed with the various fragments were observed on selection media. Then the 7 vanillin genes of each of these clones were amplified with specific primers that also verified the correct assembly of the fragments. Analysis of clones revealed that the genes had assembled resulting in correct ORFs.

Recombinant strain containing the whole pathway was grown under inducing conditions: minimal medium containing galactose as the sole carbon source. Culture was performed for at least 24 hours. They were harvested by centrifugation and supernatants recovered. HPLC was used to measure the production of vanillin and pathway intermediates in S. cerevisiae cultures. Analysis showed that chromatograms from cells expressing vanillin pathway genes (Y00VAN) contained additional peaks compared to an Y00 control. These peaks were identified by comparison to our library of molecules (FIG. 12). Thus, cinnamic acid and coumaric acid were not detected; however, 4 hydroxybenzaldehyde (8.6 µM), 3-4 dihydroxybenzaldehyde (0.29 µM), 3-4 dihydroxybenzoic acid (22.64), vanillic acid (2 µM) and vanillin (1 µM) were identified. No vanillyl alcohol was present.

Example 2: Artificial Vanillin Pathway: Metabolic Pathway to Produce Ferulic Acid Using Phenylalanine as Precursor Compound a) Artificial Ferulic Acid Pathway Five enzymes are required for the conversion of L-phenylalanine to ferulic acid (FIG. 8). Phenylalanine is converted to coumarate by the successive action of the enzymes PAL and C4H. In the proposed sequence of reaction for the second pathway, coumaric acid is first hydroxylated on 3-position of the phenyl ring by pheA protein (phenol hydroxylase) using flavin reductase coupling protein. The intermediate metabolite is the caffeic acid. Then O-methylation occurs converting the hydroxyl function in methoxy group leading to synthesis of ferulic acid using COMT protein. Most proteins are common to both pathways. They differ in the sequential order of reactions. This order is mainly due to hydroxylation reaction and the specificity of both enzymes selected to perform this reaction (PheA and HBH). PAL, C4H and COMT proteins used in this pathway are the same candidates as vanillin pathway. It is interesting to notice that, the addition of a CoA-ligase and a crotonase to the ferulic pathway leads to the production of vanillin.

b) Ferulic Acid Pathway Assembly in Yeast Host Cell

Similarly to vanillin pathway, 7 fragments containing (F1, F8, F9, F10, F11, F12, F13) the 5 genes of the ferulic pathway were designed by computational analysis. The fragments, the ORF's as well as the upstream and downstream sequences are shown in FIG. 9 (for details on the sources of the sequences see Table 3 and Table 7, for the amplification of each fragment, see Table 8). HIS3 and LEU2 are the flanking markers enabling the double selection of the recombinant pathway. Each gene possesses one promoter and one terminator sequence permitting their expression in yeast cells. After assembly of the fragments by homeologous recombination in yeast, a functional complete pathway of 19068 bp is reconstituted and the double selection permits the isolation of recombinants.

TABLE 7

Reference identities of the supplementary genes used in this example

| Gene | Species | Reference (NCBI nucleotide database) | ORF length (bp) |
|---|---|---|---|
| PheA | Geobacillus thermoleovorans | AAC38324.1 GI:3046914 | 1572 |
| flared | Geobacillus thermoleovorans | AAQ04677.1 GI:33317300 | 441 |

TABLE 8

Primers used for the amplification of the fragments used in Ferulic pathway

| primer | Sequence 5' → 3' | function |
|---|---|---|
| OL01 | SEQ ID 16: CTGTGCTGTCTGCGCTGC | Amplification F1 |
| OL02 | SEQ ID 17: ATCGTGCAAAACAACTCTGTATTCAG | |
| OL03 | SEQ ID 38: CGAAAGAGGTGAATGGTTGAAG | Amplification F9 |
| OL288 | SEQ ID 39: TTAACCTTCGTTAGATGGGAAAGAAGT | |
| OL289 | SEQ ID 40: ATGGATAGAGGTAAGACTATGATTGAAA | Amplification F10 |
| OL8 | SEQ ID 41: TTAACAAATTGGCAATGGAGCACC | |
| OL19 | SEQ ID 42: ATGGCTTACGTTAACGGTACTACT | Amplification F11 |
| OL20 | SEQ ID 43: TTACAAAGATCTTGGCTTACAAACAATA | |
| OL11 | SEQ ID 44: ATGGATTTCGTTTTGTTGGAAAAGG | Amplification F12 |
| OL12 | SEQ ID 45: TCATCTCTTTCTAATAATGTTAACATCATC | |
| OL13 | SEQ ID 46: ATGACTATTACTTCTCCAGCTCCA | Amplification F13 |
| OL14 | SEQ ID 47: TCACTTGTTGAATTCCATAACCCAAA | |
| OL15 | SEQ ID 30: ATGGGTTCTACTGGTGAAACTCAA | Amplification F8 |
| OL16 | SEQ ID 31: GCGCATGTGTCCGATCTTTG | | c) 3-Hydroxylation of Coumaric Acid

As all enzymes are common to vanillin pathway except those implied in 3 hydroxylation of coumaric acid, PheA and Flared were individually or together expressed in yeast and tested for activity using an in vivo enzyme assay. Genome integration strategy was used to clone both sequences. All integration fragments IF1-IF2-IF4 and IF5 were amplified by PCR and amplicons were purified. PheA and flared were amplified from GeneArt plasmid. Haploid a-mater BY00 was used to clone pheA gene and α-mater BY10 was used to clone flared gene. After assembly by homoeologous recombination in yeast transformant, the double selection permits the recombinant isolation. For each transformation, five recombinant clones were randomly chosen and the correct integration of the cluster was analyzed by targeted PCRs from gDNA. Diploids strains were generated by matting Y00-PheA and Y10-flared in order to co-express both proteins. Then recombinant clones expressing pheA, flared or both PheA and flared were cultured in YPAGAL induction medium to allow synthesis of proteins. After growth for 24 hours, cells were fed with 500 μM of coumaric acid. Supernatants were then analyzed by H PLC. Recombinant cell medium was fed with 500 μM coumaric acid and caffeic acid was detected in the supernatant (FIG. 10).

Example 3: Bioconversion of Vanillin From Glucose Carbon Source

In order to adapt cell for fermentation, pathway was modified to convert glucose into vanillin. Inducible promoters pGAL and pMET were removed and changed for constitutive promoters. Moreover, we introduced in a fragment, genes encoding for Carboxylic reductase and its regulatory component phosphopantetheinyl transferase. Similarly to example 1, 8 fragments containing (F14, F15, F16, F17, F18, F19, F20 and F8) the 9 genes of the vanillin pathway were designed by computational analysis. The fragments, the ORF's as well as the upstream and downstream sequences are shown in FIG. 13 (for details on the sources of the sequences see Table 9). HIS3 and LEU2 are the flanking markers enabling the double selection of the recombinant pathway. Each gene possesses one promoter and one terminator sequence permitting their expression in yeast cells. After assembly of the fragments by homeologous recombination in yeast, a functional complete pathway of 28593 bp is reconstituted and the double selection permits the isolation of recombinants.

TABLE 9

Reference identities of the upstream and downstream sequences for the vanillin genes

| | Species | Reference (NCBI nucleotide database) | Length (bp) |
|---|---|---|---|
| Promoter | | | |
| pPGPK1sce | Saccharomyces cerevisiae | FJ415226.1 GI:212656667 | 781 |
| pENO1 | Saccharomyces cerevisiae | D14474.1 GI:218423 | 500 |
| pENO2 | Saccharomyces cerevisiae | M13623.1 GI:171458 | 601 |
| pPYK | Saccharomyces cerevisiae | V01321.1 GI:4179 | 727 |
| pHXT7 | Saccharomyces cerevisiae | Z31692.1 GI:469160 | 395 |
| pADH1 | Saccharomyces cerevisiae (nt 160595 to 162095 [C]) | NC_001147.5 GI:84626310 | 1501 |
| pGDP | Saccharomyces cerevisiae | Part:BBa K124002 | 680 |
| pADH1 | Saccharomyces cerevisiae (nt 160595 to 162095 [C]) | NC_001147.5 GI:84626310 | 1501 |
| pGDP | Saccharomyces cerevisiae | Part:BBa K124002 | 680 |
| pTPISce | Saccharomyces cerevisiae | J01366.1 GI:173007 | 430 |
| Terminator | | | |
| tPYK | Saccharomyces cerevisiae | V01321.1 GI:4179 | 401 |
| tURA | Kluyveromyces lactis | D00431.1 GI:218526 | 223 |
| tTPISce | Saccharomyces cerevisiae (nt 1406 to 1649) | J01366.1 GI:173007 | 243 |
| tPGKSce | Saccharomyces cerevisiae (nt 1553 to 1839) | J01342.1 GI:172143 | 286 |

TABLE 9-continued

Reference identities of the upstream and downstream sequences for the vanillin genes

| | Species | Reference (NCBI nucleotide database) | Length (bp) |
|---|---|---|---|
| tADH1Sce | Saccharomyces cerevisiae (nt 1798 to 1991) | V01292.1 GI:3338 | 194 |
| tCYC1Sce | Saccharomyces cerevisiae (nt 559 to 838) | V01298.1 GI:3626 | 279 |

All fragments were amplified by PCR and amplicons were purified using the Wizard PCR Clean-up System (Promega). Transformations of competent yeast cells were performed with equimolar mix of 8 DNA fragments. Additionally competent cells were transformed with equimolar mix of fragments lacking one (8 negative controls). Selection of recombinant clones was performed on media without His and Leu. After 3 days clones transformed with the various fragments were observed on selection media only for transformation that contain all 8 fragments. All negative controls were negative.

REFERENCES

[1] Cheetham. (1994) The use of biotransformations for the production of flavours and fragrances. Trends biotechnol. 11:478-488;

[2] Hagedorn and Kaphammer (1994) Microbial biocatalysis in the generation of flavor and fragrance chemicals. Annu Rev. Microbiol., 48:773-800;

[3] Rosazza et al. (1995) biocatalytic transformations of ferulic acid: an abundant aromatic natural product. J. ind Microbio., 15:457-471;

[4] Häusler and Münch (1997) Microbial production of natural flavors. ASM News, 63:551-559;

[5] Krings and Berger (1998) Biotechnological production of flavours and fragrances. Appl. Microbiol. Biotechnol. 49: 1-8

[6] Abraham, W. R., Arfmann, H. A., Stumpf, S., Washausen, P., & Kieslich, K. (1988). Microbial transformations of some terpenoids and natural compounds. In P. Schreier (Ed.), Bioflavour 87, Analysis, Biochemistry, Biotechnology. Proceedings of an International Conference (pp. 399-414). Berlin: deGruyter.

[7] Rabenhorst, J., & Hopp, R. (1991). Process for the preparation of vanillin. Patent application, EPO405197.

[8] Chatterjee, T., De, B. K., & Bhattacharyya, D. K. (1999). Microbial conversion of isoeugenol to vanillin by Rhodococcus rhodochrous. Indian Journal of Chemistry B, 38, 538-541.

[9] Shimoni, E., Ravid, U., & Shoham, Y. (2000). Isolation of a Bacillus sp. capable of transforming isoeugenol to vanillin. Journal of Biotechnology, 78,1-9.

[10] Zhao, L. Q., Sun, Z. H., Zheng, P., & Zhu, L. L. (2005). Biotransformation of isoeugenol to vanillin by a novel strain of Bacillus fusiformis. Biotechnology Letters, 27, 1505-1509.

[11] Zhang, M., Xu, P., Han, S., Yan, H. Q., & Ma, C. Q. (2006). Metabolism of isoeugenol via isoeugenoldiol by a newly isolated strain of Bacillus subtilis HS8. Applied Microbiology and Biotechnology, 73, 771-779.

[12] Unno, T., Kim, S. J., Kanaly, R. A., Ahn, J. H., Kang, S. I., & Hur, H. G. (2007). Metabolic characterization of newly isolated Pseudomonas nitroreducens Jin1 growing on eugenol and isoeugenol. Journal of Agricultural and Food Chemistry, 55, 8556-8561.

[13] Yamada, M., Okada, Y., Yoshida, T., & Nagasawa,T. (2007). Biotransformation of isoeugenolto vanillin by Pseudomonas putida IE27 cells. Applied Microbiology and Biotechnology, 73, 1025-1030.

[14] Kasana, R. C., Sharma, U. K., Sharma, N., & Sinha, A. K. (2007). Isolation and identification of a novel strain of Pseudomonas chlororaphis capable of transforming isoeugenol to vanillin. Current Microbiology, 54, 457-461.

[15] Hua, D., Ma, C., Lin, S., Song, L., Deng, Z., Maomy, Z., et al. (2007). Biotransformation of isoeugenol to vanillin by a newly isolated Bacillus pumilus strain: identification of major metabolites. Journal of Biotechnology, 130, 463-470.

[16] Seshadri, R., Lamm, A. S., Khare, A., & Rosazza, J. P. N. (2008). Oxidation of isoeugenol by Nocardia iowensis. Enzyme and Microbial Technology, 43, 486-494.

[17] Esben H. Hansen, Birger Lindberg Moller, Gertrud R. Kock, Camilla M. Bünner, Charlotte Kristensen, Ole R. Jensen, Finn T. Okkels, Carl E. Olsen, Mohammed S. Motawia, and Jorgen Hansen De Novo Biosynthesis of Vanillin in Fission Yeast (Schizosaccharomyces pombe) and Baker's Yeast (Saccharomyces cerevisiae) Appl Environ Microbiol. 2009 May; 75(9): 2765-2774.

[18] Akihiko Kondo, Jun Ishii, Kiyotaka Y. Hara, Tomohisa Hasunuma, Fumio Matsuda Development of microbial cell factories for bio-refinery through synthetic bioengineering Journal of Biotechnology, Available online Jun. 19, 2012

[19] J. M. Cherry, E. L. Hong, C. Amundsen, R. Balakrishnan, G. Binkley, E. T. Chan, K. R. Christie, M. C. Costanzo, S. S. Dwight, S. R. Engel, D. G. Fisk, J. E. Hirschman, B. C. Hitz, K. Karra, C. J. Krieger, S. R. Miyasato, R. S. Nash, J. Park, M. S. Skrzypek, M. Simison, S. Weng, E. D. Wong. Saccharomyces Genome Database: the genomics resource of budding yeast. Nucleic Acids Research, 40 (2012), pp. D700-D705

[20] J. Nielsen, M. C. Jewett. Impact of systems biology on metabolic engineering of Saccharomyces cerevisiae. FEMS Yeast Research, 8 (2008), pp. 122-131

[21] J. M. Otero, W. Vongsangnak, M. A. Asadollahi, R. Olivares-Hernandes, J. Maury, L. Farinelli, L. Barlocher, M. Osteras, M. Schalk, A. Clark, J. Nielsen. Whole genome sequencing of Saccharomyces cerevisiae: from genotype to phenotype for improved metabolic engineering applications. BMC Genomics, 11 (2010), p. 723

The invention claimed is:

1. A yeast cell comprising heterologous polynucleotides encoding a multienzyme complex, wherein the multienzyme complex is involved in the metabolic pathway of phenylpropanoids and biosynthesis of a vanilloid or a hydroxybenzaldehyde precursor thereof, and wherein the multienzyme complex comprises: a) a crotonase, b) a CoA ligase, c) a 3-monooxygenase; and d) a methyltransferase; wherein a) is enoyl-CoA hydratase (ECH), b) is 4-coumarate-CoA ligase (4CL), c) is hydroxybenzoic acid hydroxylase (HBH), or phenolhydroxylase (PheA) and flavinreductase (FLARED); and d) is O-methyltransferase.

2. The yeast cell according to claim 1, which multienzyme complex comprises
   a) phenylalanine ammonia lyase (PAL), cinnamic acid hydroxylase (C4H), cytochrome P450 reductase (CPR), 4 coumarate-CoA ligase (4CL), enoyl-CoA hydratase (ECH), hydroxybenzoic acid hydroxylase (HBH), or phenolhydroxylase (PheA) and flavinreductase (FLARED), and a O-methyltransferase;
   b) tyrosine ammonia lyase (TAL), 4-coumarate-CoA ligase (4CL), enoyl-CoA hydratase (ECH), hydroxybenzoic acid hydroxylase (HBH), or phenolhydroxylase (PheA) and flavinreductase (FLARED), and a O-methyltransferase; or
   c) phenylalanine/tyrosine ammonia lyase (PAL TAL), cinnamic acid hydroxylase (C4H), cytochrome P450 reductase (CPR), 4-coumarate-CoA ligase (4CL), enoyl-CoA hydratase (ECH), hydroxybenzoic acid hydroxylase (HBH), or phenolhydroxylase (PheA) and flavinreductase (FLARED), and a O-methyltransferase.

3. The yeast cell according to claim 1, wherein enoyl-CoA hydratase (ECH) is any of
   a) an ECH responsible for the chain reduction reaction on p-coumaroylCoA and/or feruloylCoA;
   b) an ECH converting p-coumaroylCoA to 4-hydroxybenzaldehyde; or
   c) an ECH converting feruloylCoA to vanillin.

4. The yeast cell according to claim 1, which further comprises
   a) a heterologous polynucleotide encoding a carboxyreductase (CAR), optionally together with a polynucleotide encoding a phosphopantetheinyl transferase (PPTase); and/or
   b) a heterologous polynucleotide encoding an alcohol oxidase.

5. The yeast cell according to claim 1, wherein the yeast cell is of a genera selected from the group consisting of *Saccharomyces, Pichia, Hansenula, Schizosaccharomyces, Kluyveromyces, Yarrowia* and *Candida*.

6. The yeast cell according to claim 1, wherein the yeast cell is a DNA repair deficient cell or a production cell comprising a cluster of polynucleotides assembled in a DNA repair deficient cell.

7. The yeast cell according to claim 1, wherein polynucleotides encoding a series of enzymes are expressed from a single polycistronic operon, or wherein polynucleotides encoding a series of enzymes are expressed from separate promoters.

8. The yeast cell according to claim 1, wherein the polynucleotides are stably integrated into the cell genome.

9. The yeast cell according to claim 1, wherein the polynucleotides originate from at least two different species.

10. The yeast cell according to claim 1, wherein at least one of the enzymes is a chimeric enzyme.

11. The yeast cell according to claim 10, wherein the chimeric enzyme is
    a) encoded by a nucleotide sequence that is composed of fragments of different polynucleotides, which fragments are assembled to a chimeric nucleotide sequence; and/or
    b) encoded by a nucleotide sequence that is obtained by insertion, deletion and/or substitution of one or more nucleotides in a parent polynucleotide.

12. The yeast cell according to claim 1, wherein the vanilloid is selected from the group consisting of vanillin, vanillic acid, ethyl-vanillin, vanillyl alcohol and vanillin-glycoside.

13. The yeast cell according to claim 1, wherein the hydroxybenzaldehyde precursor is selected from the group consisting of protocatechuic aldehyde, protocatechuic acid, protocatechuic alcohol, 4-hydroxybenzaldehyde, 4-hydroxybenzoic acid, 4-hydroxybenzyl alcohol, cinnamic acid, coumaric acid, caffeic acid and ferulic acid.

14. A method of engineering a yeast cell according to claim 1 by introducing heterologous polynucleotides encoding a multienzyme complex involved in the metabolic pathway of phenylpropanoids and biosynthesis of a vanilloid or a hydroxybenzaldehyde precursor thereof, into the cell genome, comprising
    a) providing the polynucleotides encoding i) a crotonase, ii) a CoA ligase, ii) a-3-monooxygenase; and iv) a methyltransferase, wherein i) is enoyl-CoA hydratase (ECH), ii) is 4-coumarate-CoA ligase (4CL), iii) is hydroxybenzoic acid hydroxylase (HBH), or phenolhydroxylase (PheA) and flavinreductase (FLARED); and iv) is a O-methyltransferase;
    b) assembling the polynucleotides into a cluster and integrating said cluster into the cell genome; and
    c) optionally engineering a yeast production cell, wherein said cluster is stably integrated in the production cell genome.

15. A method, comprising:
    producing a vanilloid or a hydroxybenzaldehyde precursor thereof by heterologous biosynthesis from a yeast cell according to claim 1.

16. A method of heterologous biosynthesis of a vanilloid or a hydroxybenzaldehyde precursor thereof, by conversion of a precursor compound employing a multienzyme complex, comprising
    a) providing a yeast cell according to claim 1;
    b) cultivating said cell in a cell culture in the presence of the precursor compound;
    c) accumulating a vanilloid or a hydroxybenzaldehyde precursor thereof;
    and
    d) separating said vanilloid or hydroxybenzaldehyde precursor thereof from the cell culture medium.

17. The method of claim 16, wherein said product is a
    i. vanilloid selected from the group consisting of vanillin, vanillic acid, ethyl-vanillin, vanillyl alcohol and vanillin-glycoside; or
    ii. a hydroxybenzaldehyde precursor selected from the group consisting of protocatechuic aldehyde, protocatechuic acid, protocatechuic alcohol, 4-hydroxybenzaldehyde, 4-hydroxybenzoic acid, 4-hydroxybenzyl alcohol, cinnamic acid, coumaric acid, caffeic acid and ferulic acid.

18. The yeast cell of claim 1, wherein the enzymes for the biosynthesis of coumaric acid are selected from the group consisting of: a phenylalanine ammonia lyase (PAL), a tyrosine ammonia lyase (TAL), and a phenylalanine/tyrosine ammonia lyase (PAL/TAL).

19. The yeast cell of claim 18, wherein the multienzyme complex further comprises one or more enzymes to convert an aromatic amino acid into coumaric acid.

20. The yeast cell of claim 1, wherein the crotonase is suitable for performing a chain reduction reaction on feruloylCoA or coumaroylCoA.

21. The yeast cell of claim 18, wherein the crotonase is suitable for performing a chain reduction reaction on feruloylCoA or coumaroylCoA.

22. The yeast cell of claim 19, wherein the crotonase is suitable for performing a chain reduction reaction on feruloylCoA or coumaroylCoA.

23. The yeast cell of claim 5, wherein the cell is *Saccharomyces cerevisiae*.

\* \* \* \* \*